US008835459B2

(12) United States Patent
Kottayil et al.

(10) Patent No.: US 8,835,459 B2
(45) Date of Patent: *Sep. 16, 2014

(54) SUBLINGUAL FENTANYL SPRAY

(71) Applicant: Insys Therapeutics, Inc., Phoenix, AZ (US)

(72) Inventors: S. George Kottayil, Long Grove, IL (US); Venkat R. Goskonda, Phoenix, AZ (US); Zhongyuan Zhu, Vernon Hills, IL (US); Linet Kattookaran, Mount Prospect, IL (US); Neha Parikh, Chicago, IL (US)

(73) Assignee: Insys Therapeutics, Inc., Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/895,111

(22) Filed: May 15, 2013

(65) Prior Publication Data

US 2013/0296368 A1 Nov. 7, 2013

Related U.S. Application Data

(63) Continuation of application No. 12/221,333, filed on Aug. 1, 2008, now Pat. No. 8,486,973.

(60) Provisional application No. 60/963,076, filed on Aug. 2, 2007, provisional application No. 60/963,253, filed on Aug. 3, 2007.

(51) Int. Cl.
| | |
|---|---|
| *A01N 43/40* | (2006.01) |
| *A61K 31/445* | (2006.01) |
| *A61M 11/00* | (2006.01) |
| *A61K 31/435* | (2006.01) |
| *A61K 31/4468* | (2006.01) |
| *A61K 9/00* | (2006.01) |

(52) U.S. Cl.
CPC ........... *A61K 31/4468* (2013.01); *A61K 31/435* (2013.01); *A61M 11/00* (2013.01); *A61K 31/445* (2013.01); *A61K 9/006* (2013.01); *A61K 9/0056* (2013.01)
USPC ..................................... 514/329; 128/200.14

(58) Field of Classification Search
None
See application file for complete search history.

(56) References Cited

U.S. PATENT DOCUMENTS

| | | | |
|---|---|---|---|
| 4,244,478 A | 1/1981 | Handman | |
| 5,219,083 A | 6/1993 | Liebert et al. | |
| 5,958,379 A | 9/1999 | Regenold et al. | |
| 5,976,504 A | 11/1999 | Russell | |
| 6,759,059 B1 | 7/2004 | Pettersson et al. | |
| 6,946,150 B2 | 9/2005 | Whittle | |
| 8,486,972 B2 | 7/2013 | Kottayil et al. | |
| 2002/0055496 A1 | 5/2002 | McCoy et al. | |
| 2002/0160991 A1 | 10/2002 | Shao | |
| 2003/0039680 A1 | 2/2003 | Dugger, III | |
| 2003/0077228 A1 | 4/2003 | Dugger, III | |
| 2003/0077229 A1 | 4/2003 | Dugger, III | |
| 2003/0082107 A1 | 5/2003 | Dugger, III | |
| 2003/0095925 A1 | 5/2003 | Dugger, III | |
| 2003/0095926 A1 | 5/2003 | Dugger, III | |
| 2003/0095927 A1 | 5/2003 | Dugger, III | |
| 2003/0190286 A1 | 10/2003 | Dugger, III | |
| 2003/0190290 A1* | 10/2003 | Ross ............................... | 424/45 |
| 2004/0092428 A1 | 5/2004 | Chen et al. | |
| 2004/0120895 A1 | 6/2004 | Dugger, III | |
| 2004/0136913 A1 | 7/2004 | Dugger, III et al. | |
| 2004/0136914 A1 | 7/2004 | Dugger, III et al. | |
| 2004/0136915 A1 | 7/2004 | Dugger, III et al. | |
| 2004/0141923 A1 | 7/2004 | Dugger, III et al. | |
| 2004/0265239 A1 | 12/2004 | Dugger, III et al. | |
| 2005/0002867 A1 | 1/2005 | Dugger, III et al. | |
| 2005/0163719 A1 | 7/2005 | Dugger, III et al. | |
| 2005/0180923 A1 | 8/2005 | Dugger, III et al. | |
| 2005/0281752 A1 | 12/2005 | Dugger, III | |
| 2005/0281753 A1 | 12/2005 | Dugger, III | |
| 2005/0287075 A1 | 12/2005 | Dugger, III | |
| 2006/0062812 A1 | 3/2006 | Ross et al. | |
| 2007/0071806 A1* | 3/2007 | McCarty ....................... | 424/451 |
| 2007/0261695 A1 | 11/2007 | Kottayil et al. | |
| 2009/0124554 A1 | 5/2009 | Dugger, III | |
| 2009/0162300 A1 | 6/2009 | Dugger, III | |
| 2012/0035216 A1* | 2/2012 | Palmer et al. .................. | 514/326 |

FOREIGN PATENT DOCUMENTS

| | | |
|---|---|---|
| RU | 2156126 | 9/2000 |
| RU | 2232580 | 7/2004 |
| WO | WO 90/07333 | 7/1990 |
| WO | WO 00/47203 | 8/2000 |
| WO | WO 01/97780 A2 | 12/2001 |
| WO | WO 2004/016243 A2 | 2/2004 |
| WO | WO 2004/080382 | 9/2004 |
| WO | WO 2004/075877 | 10/2004 |
| WO | WO 2007-007059 | 1/2007 |
| WO | WO 2007/087431 | 8/2007 |

OTHER PUBLICATIONS

Int'l Preliminary Report on Patentability from related Int'l Application No. PCTIUS08/09359 dated Feb. 2, 2010.
Lejus, et al., "Fentanyl versus sufentanil: plasma concentrations during continuous epidural postoperative infusion in children," British Journal of Anaesthesia, vol. 85, Issue 4, Oct. 2000, pp. 615-617.
Examination Report for corresponding Australian Patent Application No. 2008282743, mailed on Feb. 9, 2011.
Smyth, et al., 2003, AAPS PharmSciTech 2003; 4 (3):1-11.

(Continued)

*Primary Examiner* — Robert Landsman
(74) *Attorney, Agent, or Firm* — Wood, Phillips, Katz, Clark & Mortimer

(57) ABSTRACT

The present invention is directed to sublingual formulations containing fentanyl, a pharmaceutically acceptable sale thereof, or derivative thereof, suitable for administration to a patient, and methods for treatment with the formulations.

6 Claims, 10 Drawing Sheets

(56) References Cited

OTHER PUBLICATIONS

Examination Report for corresponding Australian Patent Application No. 2008282743, mailed on Nov. 1, 2012.
Examination Report for corresponding European Patent Application No. 07762549.9, mailed on Sep. 30, 2010.
Supplementary European Search Report, 2 pages, for corresponding European Patent Application No. 07762549.9, mailed on Sep. 30, 2010.
Office Action on Chinese Patent Application No. 200780003555.X dated Jul. 9, 2010.
International Search Report and Written Opinion, dated Jul. 11, 2008 from corresponding Int'l Application No. PCT/US07/02163.
Mathar, L.E., et al. "Pulmonary administration of aerosolised fentanyl: pharmacokinetic analysis of systemic delivery" Br. J. Clin. Pharmacol. Jan. 1998, vol. 46, pp. 37-43.
Marier, J-F., et al. "Comparative bioequivalence study between a novel matrix transdermal delivery system of fentanyl and a commercially available reservoir formulation", Br. J. Clin. Pharmacol. Aug. 2006, vol. 63, No. 1, pp. 121-124, esp. p. 123, Figure 1.
International Preliminary Report on Patentability dated Aug. 26, 2008 from corresponding Int'l Application No. PCT/US07/02163.
Examination Report dated Aug. 6, 2009 from corresponding Australian Application No. 2007208229.
Examination Report dated May 5, 2010 from corresponding Canadian Application No. 2,637,672.
Examination Report dated Mar. 18, 2010 from corresponding New Zealand Application No. 569949.
An English translation of the Russian Examination Report dated Aug. 2009 from corresponding Russian Application No. 2008130763.
ISR and Written Opinion from related Int'l Application No. PCT/US08/09359 dated Jan. 9, 2009.

\* cited by examiner

Plasma concentration-time curves after IV & SL doses of Fentanyl
Figure 1: Formula of Example 1, 50 μg IV dose
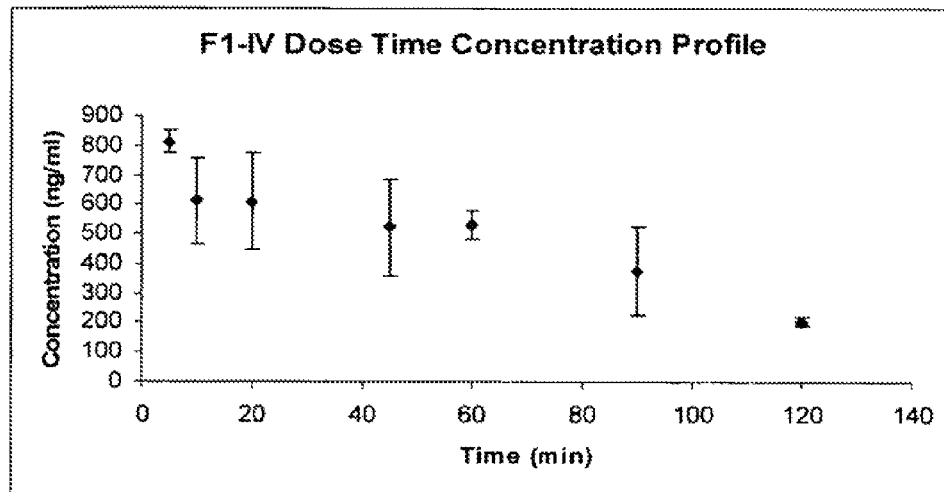
Mean (±S.E.) plasma concentration–time profiles following intravenous administration of Fentanyl ($n=3$).
Figure 2: Formula of Example 1, 50 μg Sublingual dose
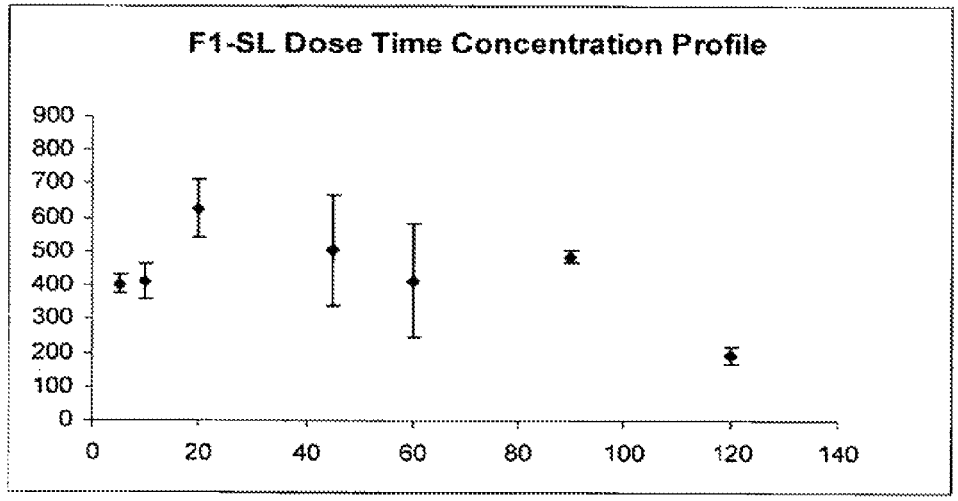
Mean (±S.E.) plasma concentration–time profiles following sublingual administration of Fentanyl ($n=3$)

Figure 3: Formula of Example 2, 80 µg IV dose
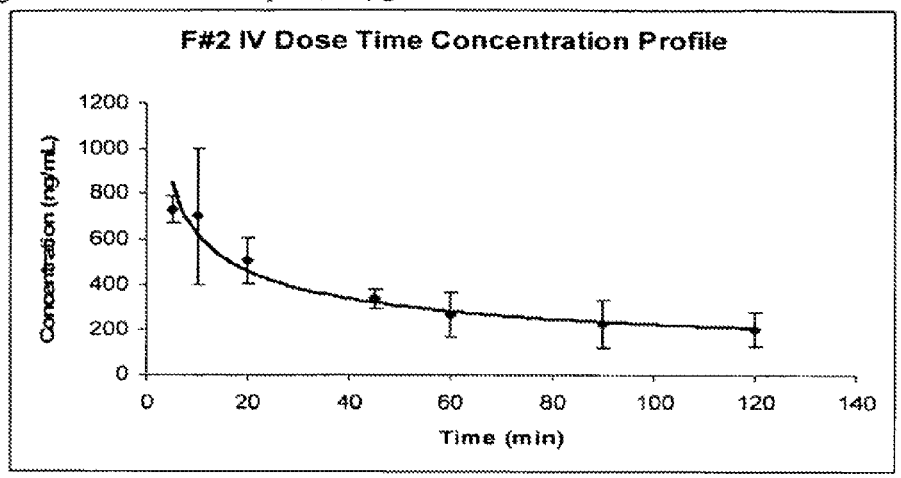
Mean (±S.E.) plasma concentration–time profiles following intravenous administration of Fentanyl ($n=3$).
Figure 4: Formula of Example 2, 80 µg SL dose
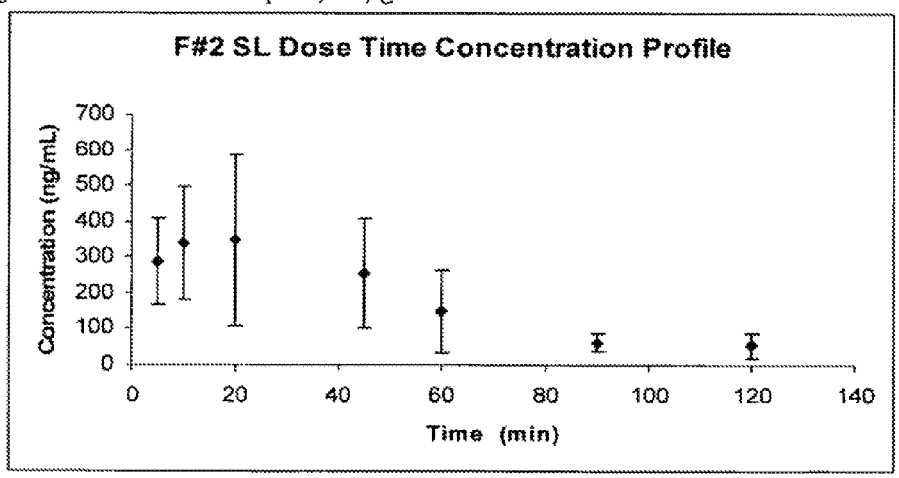
Mean (±S.E.) plasma concentration–time profiles following sublingual administration of Fentanyl ($n=3$)

Figure 5: Formula of Example 3, 50 μg IV dose
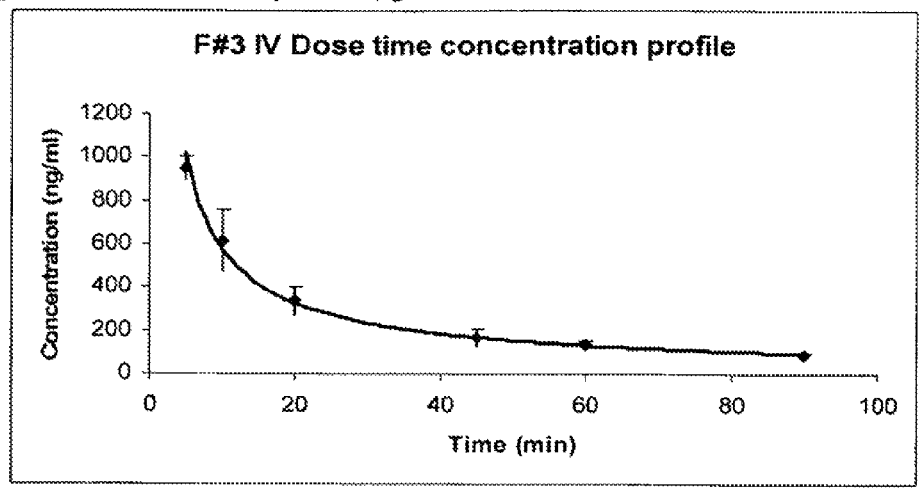
Mean (±S.E.) plasma concentration–time profiles following intravenous administration of Fentanyl ($n=3$)
Figure 6: Formula of Example 3, 50 μg SL dose
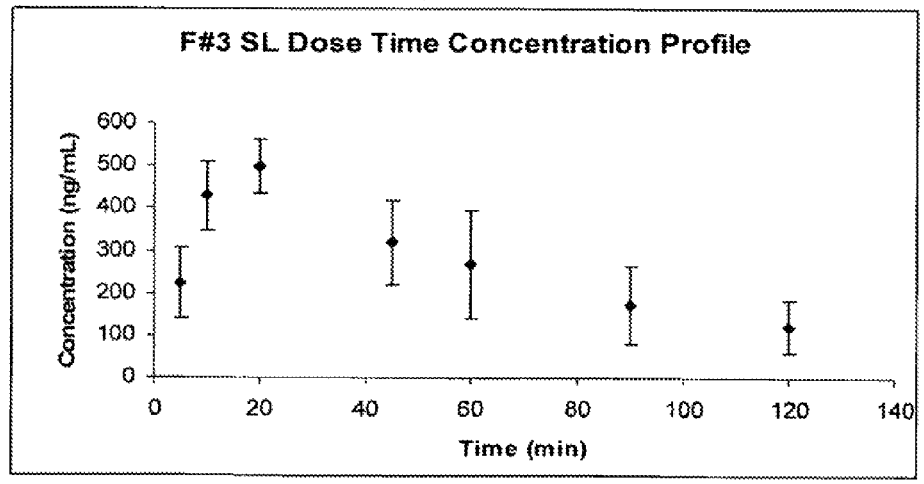
Mean (±S.E.) plasma concentration–time profiles following sublingual administration of Fentanyl ($n=3$)

Figure 7: Formula of Example 4, 50 µg IV dose
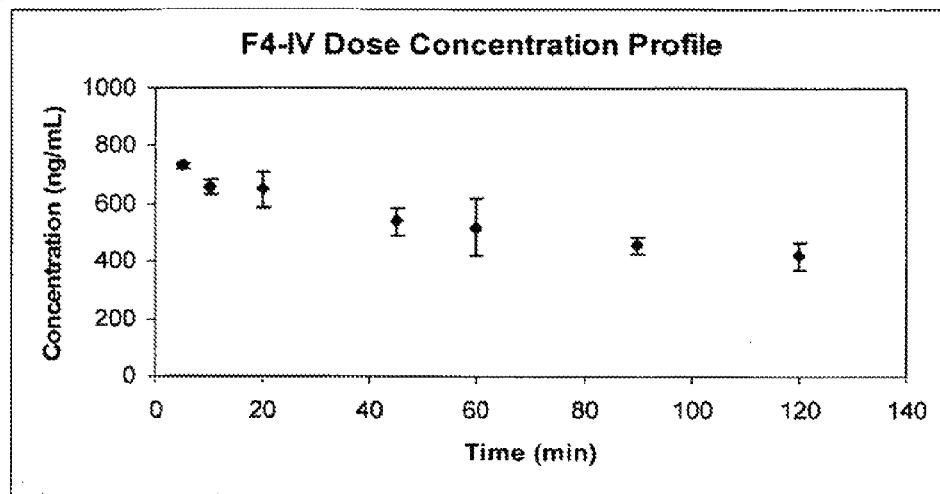
Mean (±S.E.) plasma concentration–time profiles following intravenous administration of Fentanyl (n=3)
Figure 8: Formula of Example 4, 50 µg SL dose
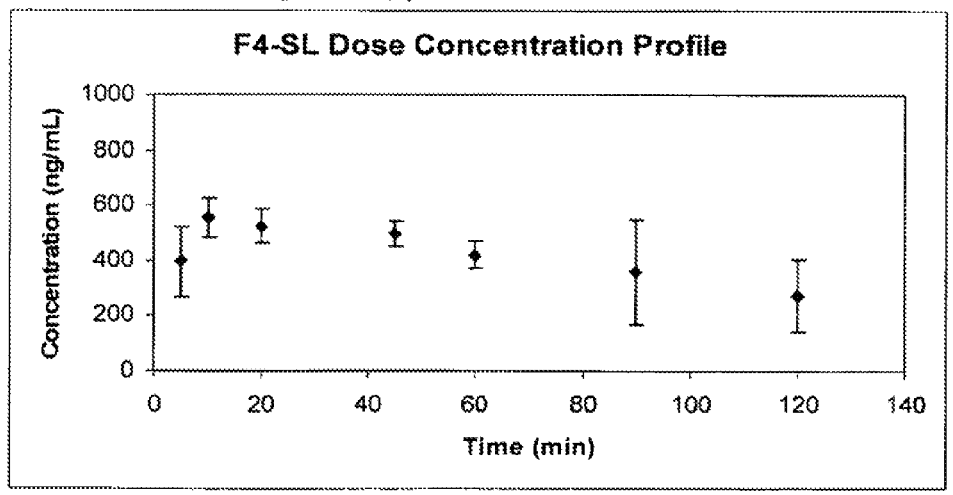
Mean (±S.E.) plasma concentration–time profiles following sublingual administration of Fentanyl (n=3)

Figure 9: Formula of Example 5, 50 μg IV dose
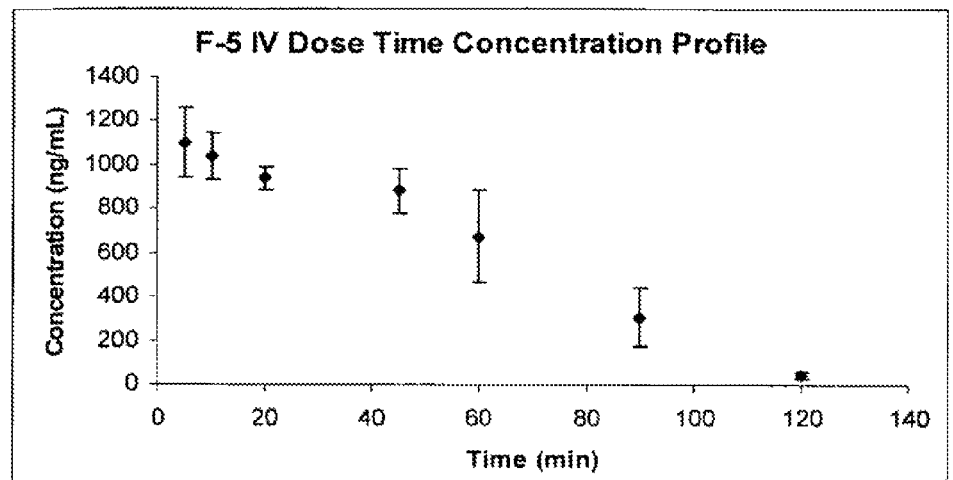
Mean (±S.E.) plasma concentration–time profiles following intravenous administration of Fentanyl ($n=3$)
Figure 10: Formula of Example 5, 50 μg SL dose
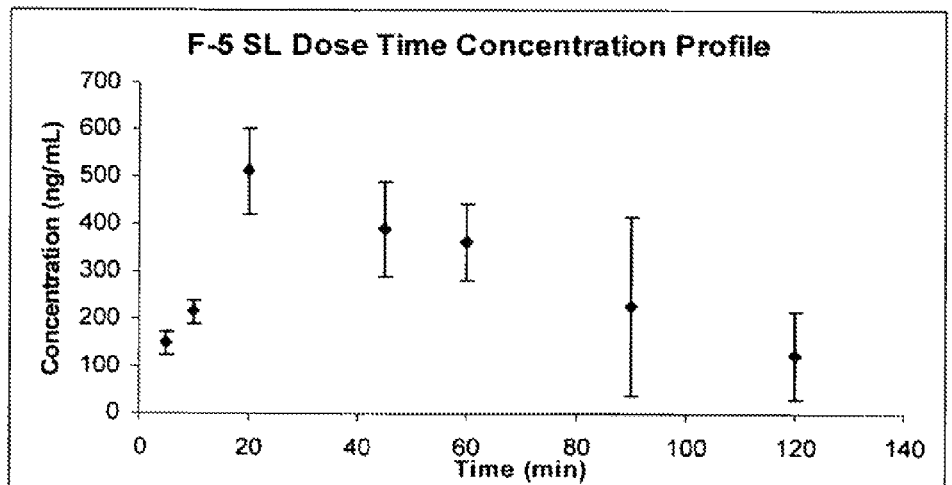
Mean (±S.E.) plasma concentration–time profiles following sublingual administration of Fentanyl ($n=3$)

An expanded X-axis time scale. Notice that concentrations are generally at ~60% of peak by 10 minutes. The peak is approximately 100 minutes broad.

SUBLINGUAL FENTANYL SPRAY

This application is a continuation of U.S. patent application Ser. No. 12/221,333 filed Aug. 1, 2008 (now U.S. Pat. No. 8,486,973 issued Jul. 16, 2013), which claims the benefit of U.S. Provisional Application Nos. 60/963,076, filed on Aug. 2, 2007 and 60/963,253 filed Aug. 3, 2007; the disclosures of which are hereby incorporated by reference in their entireties.

FIELD OF THE INVENTION

The invention is directed to sublingual formulations containing fentanyl, a pharmaceutically acceptable salt thereof, or derivative thereof, suitable for administration to humans, and methods for treatment with the sublingual formulations.

BACKGROUND OF THE INVENTION

Fentanyl is a μ-opioid receptor agonist with analgesic potency approximately 80-100 times that of morphine. In clinical settings, fentanyl exerts its principal pharmacologic effects on the central nervous system. Its primary actions are analgesic and sedation.

The analgesic effects of fentanyl are related to the blood level of the drug. In general, the minimum effective concentration and the concentration at which toxicity occurs rise with increasing tolerance to any and all opioids. The rate of development of tolerance may vary widely among individuals. All opioid mu-receptor agonists, including fentanyl, produce dose dependent respiratory depression. The risk of respiratory depression is typically less in patients receiving chronic opioid therapy who develop tolerance to respiratory depression and other opioid effects. Serious or fatal respiratory depression can occur, even at recommended doses, in vulnerable individuals.

Orally administered fentanyl is subject to first pass effect metabolism as upwards of 50% or more of orally administered fentanyl is not absorbed. Other forms of delivery such a parenteral, buccal, and transdermal have been utilized to decrease or avoid this first pass effect for fentanyl.

Fentanyl is currently available in injectable form, as a lozenge (e.g. Actiq®; fentanyl citrate; Actiq is a registered trademark of Anesta, LLC), and as a transdermal patch (e.g. Duragesic® 25, 50, 75, and 100 μg of fentanyl per hour; Duragesic is a registered trademark of Johnson & Johnson Corporation). Duragesic® provides continuous systemic delivery of fentanyl for approximately 72 hours. Duragesic® is indicated in the management of chronic pain in patients requiring continuous opioid analgesia for pain that is not optimally managed with lesser means such as acetaminophen-opioid combinations, non-steroidal analgesics, or prn (as needed) dosing with short-acting opioids. Duragesic® is typically not suitable for patients experiencing acute pain due to the delay in absorption of the fentanyl through the patch, or postoperative pain because serious or life-threatening hypoventilation could result.

Actiq® is a solid formulation of fentanyl citrate, intended for oral transmucosal administration. Actiq® is a lozenge attached to a handle similar in shape to a lollipop. The handle is purportedly to allow the Actiq® unit to be removed from the mouth if signs of excessive opioid effects appear during administration. Actiq® is indicated for the management for breakthrough cancer pain in patients with malignancies who are already receiving and who are tolerant to opioid therapy for their underlying persistent cancer pain. Actiq® is contraindicated in the management of acute or postoperative pain.

Sublingual tablets and lozenges (e.g., Actiq®) which may be used for acute pain or breakthrough pain have certain disadvantages. A disadvantage, amongst others, is that after intake the active agent in these pharmaceutical agents must first be released and dispersed prior to being available for resorption in dissolved form. In addition, the absorption pharmacokinetics of fentanyl from Actiq® may vary depending on the fraction of the dose that is absorbed through the oral mucosa and the fraction swallowed. Further, certain lozenges may be in the form of a candy which require medical supervision and may be socially questionable.

There exists a need in art for a sublingual formulation including fentanyl, a pharmaceutically acceptable salt thereof, or derivative thereof, which is suitable for effective pain management.

SUMMARY AND OBJECTS OF THE INVENTION

It is an object of the invention to provide a fentanyl formulation suitable for sublingual administration for effective pain management.

It is an object of certain embodiments of the invention to provide methods and compositions capable of rapidly inducing a state of sedation, analgesia, and/or anesthesia.

It is a further object of certain embodiments of the invention to provide methods and compositions for fentanyl administration which minimize the underdosing and/or overdosing of a patient in need of fentanyl therapy.

It is a further object of certain embodiments of the invention to provide methods and compositions suitable for the treatment of breakthrough pain in patients receiving chronic pain treatment.

It is a further object of certain embodiments of the present invention to provide a method for sublingual administration of fentanyl, a pharmaceutically acceptable salt thereof, or derivative thereof, in a controlled amount for the treatment of pain.

It is a further object of certain embodiments of the present invention to provide a dosage form of an opioid analgesic which can be administered sublingually in a manner which will cause substantial sublingual absorption without substantial risk of the dose passing into the lungs of the recipient.

The above-mentioned objects and others are achieved by virtue of the present invention, which is directed in part to a method for sublingually administering fentanyl, a pharmaceutically acceptable salt thereof, or derivative thereof, to provide fast-acting relief in a formulation in which a substantial portion of the fentanyl, a pharmaceutically acceptable salt thereof, or derivative thereof will not be passed into the lungs of the patient.

In certain embodiments the present invention is directed to a sublingual fentanyl formulation comprising discrete liquid droplets comprising an effective amount of fentanyl, a pharmaceutically acceptable salt thereof, or derivative thereof, said droplets having a mean diameter of at least about 10 microns, preferably at least about 20 microns, more preferably a mean diameter of from about 20 to about 200 microns.

In certain embodiments, the present invention is directed to a sublingual fentanyl formulation comprising discrete liquid droplets of fentanyl, a pharmaceutically acceptable salt thereof, or derivative thereof; in a pharmaceutically acceptable liquid carrier; said droplets having a size distribution of from about 5 microns to about 500 microns, preferably from about 10 microns to about 200 microns, preferably from about 20 microns to about 100 microns, more preferably from about 30 microns to about 70 microns.

In certain preferred embodiments, none of the particles have a diameter which would allow the fentanyl, pharmaceutically acceptable salt thereof, or derivative thereof to be delivered to the lung upon sublingual administration.

In certain embodiments, the present invention is directed to a unit dose of a sublingual fentanyl formulation, said unit dose comprising discrete liquid droplets of fentanyl, a pharmaceutically acceptable salt thereof, or derivative thereof; and a pharmaceutically acceptable liquid carrier; said droplets having a mean diameter of at least about 10 microns, preferably at least about 20 microns, more preferably a mean diameter of from about 20 to about 200 microns.

In certain embodiments, the present invention is directed to a unit dose of a sublingual fentanyl formulation, said unit dose comprising discrete liquid droplets of fentanyl, a pharmaceutically acceptable salt thereof, or derivative thereof; and a pharmaceutically acceptable liquid carrier; said droplets having a size distribution of from about 5 microns to about 500 microns, preferably from about 10 microns to about 200 microns, preferably from about 20 microns to about 100 microns, more preferably from about 30 microns to about 70 microns.

In certain embodiments, the present invention is directed to a method of treating pain comprising sublingually administering a liquid spray formulation in the form of discrete liquid droplets having a mean diameter of at least about 10 microns, preferably at least about 20 microns, more preferably a mean diameter of from about 20 to about 200 microns, to a human patient experiencing pain, said liquid spray formulation comprising an effective amount of fentanyl, a pharmaceutically acceptable salt thereof, or derivative thereof, dispersed in a pharmaceutically acceptable liquid carrier.

In certain embodiments, the present invention is directed to a method of treating pain comprising sublingually administering a liquid spray formulation in the form of discrete liquid droplets having a size distribution of from about 5 microns to about 500 microns, preferably from about 10 microns to about 200 microns, preferably from about 20 microns to about 100 microns, more preferably from about 30 microns to about 70 microns to a human patient experiencing pain; said liquid spray formulation comprising an effective amount of fentanyl, a pharmaceutically acceptable salt thereof, or derivative thereof, dispersed in a pharmaceutically acceptable liquid carrier.

In certain embodiments, the present invention is directed to a device which includes a reservoir containing a unit dose of a liquid formulation comprising an effective amount of fentanyl, a pharmaceutically acceptable salt thereof, or derivative thereof in a pharmaceutically acceptable liquid carrier; the device having an actuator which when actuated delivers the unit dose of the liquid formulation in the form of liquid droplets having a mean diameter of at least about 10 microns, preferably at least about 20 microns, more preferably a mean diameter of from about 20 to about 200 microns. Preferably, the device delivers a therapeutically effective dose of the liquid formulation in the form of liquid droplets having a size distribution of from about 5 microns to about 500 microns, preferably from about 10 microns to about 200 microns, preferably from about 20 microns to about 100 microns, more preferably from about 30 microns to about 70 microns.

In certain embodiments, the present invention is directed to a multi-dose device which includes a reservoir containing a liquid formulation comprising fentanyl, a pharmaceutically acceptable salt thereof, or derivative thereof in a pharmaceutically acceptable liquid carrier; the device having an actuator which when actuated delivers a therapeutically effective dose of the liquid formulation in the form of liquid droplets having a mean diameter of at least about 10 microns, preferably at least about 20 microns, more preferably a mean diameter of from about 20 to about 200 microns. Preferably, the device delivers a therapeutically effective dose of the liquid formulation in the form of liquid droplets having a size distribution of from about 5 microns to about 500 microns, preferably from about 10 microns to about 200 microns, preferably from about 20 microns to about 100 microns, more preferably from about 30 microns to about 70 microns.

In certain embodiments, the present invention is directed to a method of treating pain comprising utilizing a spray device which includes a reservoir including a liquid formulation comprising fentanyl, a pharmaceutically acceptable salt thereof, or derivative thereof in a pharmaceutically acceptable liquid carrier; and an actuator which upon actuation delivers a therapeutically effective amount of liquid droplets to be sprayed from the device having a mean diameter of at least about 10 microns, preferably at least about 20 microns, more preferably a mean diameter of from about 20 to about 200 microns.

In certain embodiments, the present invention is directed to a method of treating pain comprising utilizing a spray device which includes a reservoir including a liquid formulation comprising fentanyl, a pharmaceutically acceptable salt thereof, or derivative thereof; and a pharmaceutically acceptable liquid carrier; and an actuator which upon actuation delivers a therapeutically effective amount of liquid droplets having a size distribution of from about 5 microns to about 500 microns, preferably from about 10 microns to about 200 microns, preferably from about 20 microns to about 100 microns, more preferably from about 30 microns to about 70 microns.

In certain embodiments, the present invention is directed to a method of treating breakthrough pain comprising sublingually administering a liquid spray formulation comprising an effective amount of fentanyl, a pharmaceutically acceptable salt thereof, or derivative thereof, dispersed in a pharmaceutically acceptable liquid carrier to a human patient to treat breakthrough pain experienced by said human patient.

In certain embodiments, the present invention is directed to a method of treating breakthrough pain comprising sublingually administering a liquid spray formulation comprising an effective amount of fentanyl, a pharmaceutically acceptable salt thereof, or derivative thereof, dispersed in a pharmaceutically acceptable liquid carrier to a human patient who is receiving chronic pain treatment, and is experiencing breakthrough pain.

In certain embodiments, the present invention is directed to a method of reducing patient to patient variability for the treatment of breakthrough pain, comprising sublingually administering to a human patient experiencing breakthrough pain a dose of fentanyl in a liquid spray formulation comprising fentanyl, a pharmaceutically acceptable salt thereof, or derivative thereof, and a pharmaceutically acceptable liquid carrier said liquid spray formulation being administered as discrete liquid droplets having a mean diameter of at least about 10 microns, preferably at least about 20 microns, more preferably a mean diameter of from about 20 to about 200 microns.

In certain embodiments, the present invention is directed to a method of reducing patient to patient variability for the treatment of breakthrough pain, comprising sublingually administering to a human patient experiencing breakthrough pain a dose of fentanyl in a liquid spray formulation comprising fentanyl, a pharmaceutically acceptable salt thereof, or derivative thereof, and a pharmaceutically acceptable liquid carrier said liquid spray formulation being administered as discrete liquid droplets having a size distribution of from about 5 microns to about 500 microns, preferably from about 10 microns to about 200 microns.

In certain preferred embodiments, the liquid spray formulation further includes a pharmaceutically acceptable solvent. Preferably the pharmaceutically acceptable solvent is an organic solvent which is included in an amount suitable for dissolving the fentanyl, a pharmaceutically acceptable salt thereof, or derivative thereof.

In certain preferred embodiments the formulations of the present invention provide a mean time to maximum plasma concentration ($T_{max}$) of fentanyl at from about 5 minutes to about 120 minutes, after sublingual administration to humans.

In certain preferred embodiments the formulations of the present invention provide a mean maximum plasma concentration ($C_{max}$) of fentanyl of about 127 pg/ml to about 213 pg/ml per 100 μg fentanyl after sublingual administration to humans.

In certain preferred embodiments of the present invention the formulations of the present invention do not include a propellant.

In certain embodiments, the formulations of the present invention are suitable for transmucosal administration, including, for example, buccal administration.

In certain embodiments, the present invention is further directed to a method of transmucosally administering fentanyl, a pharmaceutically acceptable salt thereof, or derivative thereof, to a human to provide fast-acting relief in a formulation in which a substantial portion of the fentanyl, a pharmaceutically acceptable salt thereof, or derivative thereof will not be passed into the lungs of the patient. In certain preferred embodiments, the transmucosal area is the buccal area of a human.

In certain embodiments, the present invention is further directed to the use of a formulation as defined above for the manufacture of a medicament for use as an analgesic, for the treatment of acute pain and/or breakthrough pain, as an anesthetic premedication, for the induction of anesthesia, as a sedative and/or for the treatment of anxiety.

The invention is also directed to a sublingual fentanyl formulation comprising discrete liquid droplets of an effective amount of fentanyl, a pharmaceutically acceptable salt thereof, or derivative thereof; in a pharmaceutically acceptable liquid carrier; said droplets having a mean diameter of at least about 10 microns, and upon administration to a human patient, at least about 90% of the discrete liquid droplets have a mean diameter equal or greater than about 9 μm. In other embodiments, not more than about 5% of the discrete liquid droplets have a mean diameter less than 9 μm. In still other embodiments, the formulation provides a respirable dose of not more than about 5% of the total fentanyl dose contained.

The invention is also directed to a method of treating pain comprising sublingually administering a liquid spray formulation in the form of discrete liquid droplets having a mean diameter of at least about 10 microns to a human patient experiencing pain and at least about 90% of the discrete liquid droplets have a mean diameter equal or greater than about 9 μm upon administration to a human patient, said liquid spray formulation comprising an effective amount of fentanyl, a pharmaceutically acceptable salt thereof, or derivative thereof, dispersed in a pharmaceutically acceptable liquid carrier. In certain other embodiments, not more than about 5% of the discrete liquid droplets have a mean diameter less than 9 μm. In other embodiments, the formulation provides a respirable dose of not more than about 5% of the total fentanyl dose contained.

The invention is also directed to a unit dose or bi-dose device for sublingual administration of a drug comprising:

a reservoir containing a unit dose or a bi-dose of a liquid formulation comprising an effective amount of fentanyl, a pharmaceutically acceptable salt thereof, or derivative thereof in a pharmaceutically acceptable liquid carrier; and the device having an actuator which when actuated delivers the unit dose of the liquid formulation in the form of liquid droplets having a mean diameter of at least about 10 microns, and wherein upon administration to a human patient, at least about 90% of the discrete liquid droplets have a mean diameter equal or greater than about 9 μm.

In other embodiments, not more than about 5% of the discrete liquid droplets have a mean diameter less than 9 μm. In still other embodiments, the formulation provides a respirable dose of not more than about 5% of the total fentanyl dose contained.

In accordance with the above objects, the invention is also directed to a sublingual spray formulation comprising an effective amount of fentanyl and at least one pharmaceutically acceptable excipient, the formulation providing a mean Tmax of about 1.28+/−0.60 hours when a dose is administered sublingually to humans. In certain other embodiments, the sublingual formulation has a concentration of fentanyl from about 1 mg/mL to about 8 mg/mL. In certain preferred embodiments, the concentration of fentanyl is about 1 mg/mL, about 2 mg/mL, about 4 mg/mL, about 6 mg/mL or about 8 mg/mL.

In accordance with certain of the above objections, the invention is also directed to a sublingual formulation exhibiting a mean Cmax of about 0.813 ng/ml+/−0.252 based on a sublingual dose of about 400 mcg fentanyl when administered to humans.

In certain other embodiments, the sublingual formulation provides a dosage amount of fentanyl selected from the group consisting of about 100 mcg, about 200 mcg, about 600 mcg and about 800 mcg, and provides a mean Cmax which is substantially dose proportional to the sublingual formulation containing 400 mcg fentanyl dosage amount, when administered to humans.

In still other embodiments, the sublingual formulation provides a substantially dose proportional mean Cmax based on a mean Cmax of about 0.813 ng/ml+/−0.252 for a 400 mcg fentanyl dose when administered to humans.

The present invention also provides a sublingual formulation which provides a mean Tmax when administered to humans selected from the group consisting of: about 1.12 hours when the formulation provides a 100 mcg dose, about 1.04 hours when the formulation provides a 200 mcg dose, about 0.97 hours when the formulation provides a 400 mcg dose, about 0.987 hours when the formulation provides a 600 mcg dose, and about 1.06 hours when the formulation provides a 800 mcg dose.

In accordance with the above objects, it is a further object of the invention to provide a sublingual fentanyl formulation which provides a plasma concentration after administration to humans selected from the group consisting of: about 60% of the mean Cmax in about 10 minutes, about 86% of the mean Cmax by about 20 minutes and a combination thereof.

In other embodiments, the invention is directed to a sublingual fentanyl formulation that when administered to humans provides a plasma concentration that is greater than about 80% of the mean Cmax for about 2 hours.

In still other embodiments, the sublingual formulation comprises 400 mcg of fentanyl, providing one or more mean pharmacokinetic values selected from the group consisting of: AUClast 4.863+/−1.70821 hr*ng/mL, AUCinf 5.761+/−1.916 hr*ng/mL, and AUCextrap 10.26+/−5.66%, when administered to humans.

In even still further embodiments of the invention, the sublingual fentanyl formulation provides a dosage amount of fentanyl when administered to humans which is substantially dose proportional to the dosage which contains about 400 mcg fentanyl selected from the group consisting of about 100 mcg, about 200 mcg, about 600 mcg, about 800 mcg, and provides one or more pharmacokinetic values selected from the group consisting of: mean $AUC_{last}$, mean $AUC_{inf}$, and mean $AUC_{extrap}$.

In still further embodiments of the invention, the sublingual fentanyl formulation provides a substantially dose proportional mean AUClast based on a mean AUClast of about 4.863+/−1.70821 hr*ng/mL for a 400 mcg fentanyl dose when administered to humans.

It is also an object of the invention to a provide a sublingual formulation comprising a 400 mcg dose of fentanyl, providing a geometric mean ln(Cmax) of about 0.7865 ng/ml when a dose is administered to humans.

In still other embodiments, the sublingual formulation comprises a 400 mcg dose of fentanyl, providing a mean F(AUClast) of about 0.721+/−0.199 ng/mL when a dose is administered to humans.

In other embodiments, the invention is directed to a sublingual formulation comprising a 400 mcg dose of fentanyl that when administered to humans, provides a mean F (bioavailability) selected from the group consisting of: about 71%+/−16%, 0.721+/−0.199 based on AUClast and about 0.756+/−0.212 based on AUCinf, or combinations thereof.

In accordance with the above objects, the invention is further directed to a sublingual fentanyl spray formulation that further comprises water. In other embodiments, the formulations further comprise dehydrated alcohol.

It is also an object of the invention to provide a method of treating pain comprising administering to a patient in need thereof a sublingual spray formulation comprising an effective amount of fentanyl and at least one pharmaceutically acceptable excipient, the formulation providing a mean Tmax of about 1.28+/−0.60 hours when a dose is administered sublingually to humans.

In accordance with the above objects, the invention is also directed to a method of treatment wherein the sublingual formulation provides a substantially dose proportional mean Cmax based on a mean Cmax of about 0.813 ng/ml+/−0.252 for a 400 mcg fentanyl dose when administered to humans.

In yet further embodiments, the invention is also directed to a method of treatment wherein the sublingual formulation provides a substantially dose proportional mean AUClast based on a mean AUClast of about 4.863+/−1.70821 hr*ng/mL for a 400 mcg fentanyl dose when administered to humans.

It is a further object of the invention to provide a method of manufacturing a sublingual spray formulation comprising an effective amount of fentanyl and at least one pharmaceutically acceptable excipient comprising: admixing fentanyl, purified water and dehydrated alcohol and placing the mixture into a sublingual delivery device; wherein the formulation provides a mean Tmax of about 1.28+/−0.60 hours when a dose is administered sublingually to humans and upon delivery provides particles having a mean aerodynamic particle size of at least about 10 microns.

Many patients with e.g., cancer, typically continue to experience moderate to severe pain despite chronic analgesic therapy and this can occur as intermittent breakthrough pain, often due to increases in a patient's activity level. Attempts to counteract this type of pain by increasing the dose of long-acting formulations of analgesics often produce slow onset of analgesia and unwanted side-effects of sedation, constipation or nausea and vomiting. However, in certain embodiments the present invention is directed to a formulation which preferably provides a rapidly acting, potent analgesic which reduces the pain, such as breakthrough pain, for the required time and then preferably wears off fairly quickly thereby minimizing the side-effects of the fentanyl, a pharmaceutically acceptable salt thereof, or derivative thereof.

For purposes of the present invention, derivatives of fentanyl include sufentanil, carfentanil, lofentanil, alfentanil, or the like.

For purposes of the present invention, "breakthrough pain" refers to a pain that exceeds a threshold in a patient which causes cognizable discomfort wherein the pain experienced by the patient is otherwise typically controlled e.g., by chronic analgesic therapy, and tolerated. For example, pain related to medical illnesses, such as cancer, typically fluctuates, and patients often report the experience of cognizable discomfort (e.g., breakthrough pain). Typically breakthrough pain is currently treated with immediate release oral dosage forms which may take up to about 45 minutes or longer for the drug to be absorbed and may result in a delay of the relief of breakthrough pain, as opposed to a liquid spray formulation of the present invention which begins to provide relief of the breakthrough pain almost immediately after administration.

For purposes of the present invention, "chronic pain treatment" refers to a daily or round-the-clock pain treatment. Chronic pain treatment can be oral, parenteral, transdermal, or other suitable means of administration.

For purposes of the present invention, "sublingual" is defined herein as beneath or concerning the area under the tongue.

For purposes of the present invention the term "sublingual administration" is defined herein as the therapeutic administration of a pharmaceutical composition under the tongue.

For purposes of the present invention an "effective amount" of a drug is an amount effective to demonstrate a desired activity of the drug. According to the instant invention, a therapeutically effective amount of fentanyl, pharmaceutically acceptable salt thereof, or derivative thereof, is an amount effective to treat, e.g., noticeably reduce, pain in a patient.

For purposes of the present invention the terms droplets and particles may be used interchangeably.

BRIEF DESCRIPTION OF THE DRAWINGS

FIG. 1 depicts the mean (±S.E.) plasma concentration-time profiles following intravenous administration of Fentanyl of Example 1 (n=3) in the study of Example 6.

FIG. 2 depicts the mean (±S.E.) plasma concentration-time profiles following sublingual administration of Fentanyl of Example 1 (n=3) in the study of Example 6.

FIG. 3 depicts the mean (±S.E.) plasma concentration-time profiles following intravenous administration of Fentanyl of Example 2 (n=3) in the study of Example 6.

FIG. 4 depicts the mean (±S.E.) plasma concentration-time profiles following sublingual administration of Fentanyl of Example 2 (n=3) in the study of Example 6.

FIG. 5 depicts the mean (±S.E.) plasma concentration-time profiles following intravenous administration of Fentanyl of Example 3 (n=3) in the study of Example 6.

FIG. 6 depicts the mean (±S.E.) plasma concentration-time profiles following sublingual administration of Fentanyl of Example 3 (n=3) in the study of Example 6.

FIG. 7 depicts the mean (±S.E.) plasma concentration-time profiles following intravenous administration of Fentanyl of Example 4 (n=3) in the study of Example 6.

FIG. 8 depicts the mean (±S.E.) plasma concentration-time profiles following sublingual administration of Fentanyl of Example 4 (n=3) in the study of Example 6.

FIG. 9 depicts the mean (±S.E.) plasma concentration-time profiles following intravenous administration of Fentanyl of Example 5 (n=3) in the study of Example 6.

FIG. 10 depicts the mean (±S.E.) plasma concentration-time profiles following sublingual administration of Fentanyl of Example 5 (n=3) in the study of Example 6.

DETAILED DESCRIPTION OF THE INVENTION

Figure 11:
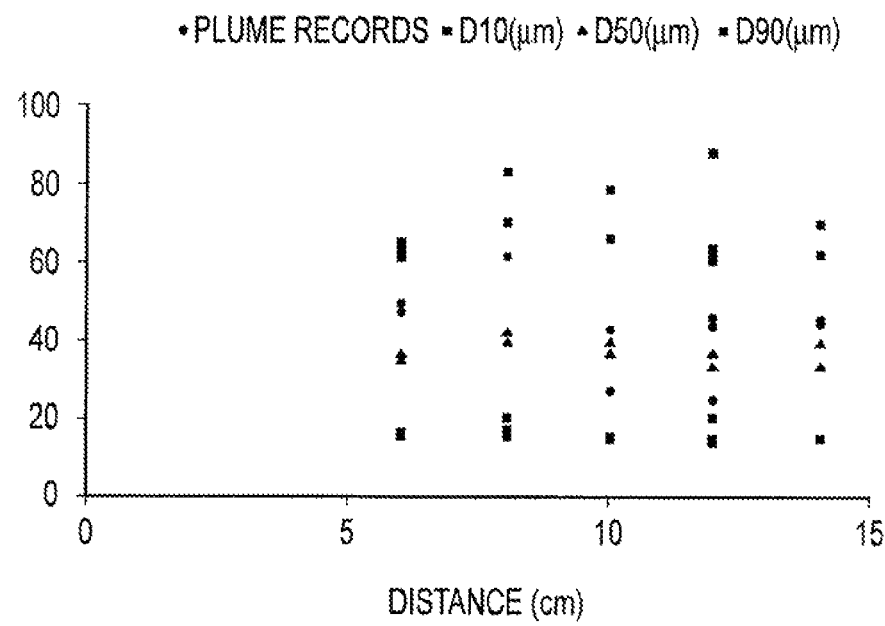
FIG. 11 depicts a graphical summary of the Dv10, Dv50, Dv90, and plume records values versus placement distance for vignetting results.

The simplest and most prevalent administration route for pharmacologic agents is by mouth. To use this method, a pharmacological agent is typically incorporated into a tablet, a capsule, or into a liquid base. Oral administration of a drug is extremely convenient, and for many drugs, it will continue to be the method of choice.

Absorption of a drug into the bloodstream after swallowing a tablet may vary from patient to patient. The absorption of the drug is typically dependent upon the movement from the stomach to the small and large intestines and the effects of secretions from these organs. Further, with the oral administration of a drug such as fentanyl to a patient, as the fentanyl enters the patient's bloodstream through the intestines and passes through the patient's liver before distribution throughout the body, upwards of fifty percent or more of the fentanyl may be removed from the patient's bloodstream. This "first pass effect" results in the oral route of administration being impractical for fentanyl.

Absorption of fentanyl or a pharmaceutically acceptable salt thereof into the bloodstream following oral administration is significantly reduced by the first pass effect. Therefore, the oral route of administration is impractical for fentanyl. Other forms of delivery such a parenteral, buccal, and transdermal delivery have been utilized to decrease or avoid this first pass effect for fentanyl. However, these other forms of delivery have certain disadvantages associated with them. For example, parenteral administration requires injection using a syringe and needle, and may lead to necrosis that can accompany i.m. administration of drugs; Actiq®, a transmucosal fentanyl citrate lozenge formulation requires the patient to constantly suck on the lozenge which is attached to a handle (similar to a lollipop) in order to obtain effective pain relief; and Duragesic®, a transdermal fentanyl delivery device, is suitable for the management of chronic pain, but is not indicated for acute or breakthrough pain.

The oral cavity offers a simple, painless method of opioid analgesic administration. Within the oral cavity, there are three generally recognized routes of administration of an active agent, namely local, buccal and sublingual.

Local delivery is mainly limited to applications regarding disruptions occurring within the oral cavity itself, such as a canker sore.

The buccal mucosa area encompasses the mucosal membranes of the inner lining of the cheeks. The buccal mucosa is however, less permeable than the sublingual area. One of the major disadvantages associated with buccal mucosa delivery of an active agent has been the relatively low passage of active agents across the mucosal epithelium, thereby resulting in low agent bioavailability, which translates into a substantial loss of usable active agent within each dosage.

Sublingual delivery is achieved through the mucosal membranes lining the floor of the mouth. Because of the high permeability and the rich blood supply, transport via the sublingual route results in a rapid onset of action, providing a delivery route appropriate for highly permeable drugs with short delivery period requirements and an infrequent dosing regimen.

The sublingual formulations of the present invention are useful in the treatment of moderate to severe pain. Preferably the sublingual formulations of the present invention are useful for the treatment of breakthrough pain. For example, the formulations of the present invention are preferably suitable for a patient receiving chronic pain therapy who experiences breakthrough pain and is in need of acute pain relief.

The sublingual formulations of the present invention may be used to alleviate pain from many causes, including but not limited to shock, limb amputation, severe chemical or thermal burn injury, sprains, ligament tears, fractures, wounds and other tissue injuries, dental surgery, procedures and maladies, labor and delivery, during physical therapy, post operative pain, radiation poisoning, cancer, acquired immunodeficiency syndrome (AIDS), epidural (or peridural) fibrosis, back surgery and laminectomy, sciatica, painful sickle cell crisis, arthritis, autoimmune disease, intractable bladder pain, and the like. Sublingual administration of the formulations of fentanyl, a pharmaceutically acceptable salt thereof, or derivative thereof, of the present invention is also preferably amenable to hospice use, particularly hospices that specialize in the care of cancer and AIDS patients.

In certain preferred embodiments, the sublingual administration of fentanyl, a pharmaceutically acceptable salt thereof, or derivative thereof, can relieve or alleviate episodes of acute breakthrough pain that can occur in a chronic pain condition. In a further embodiment, sublingual administration of fentanyl, pharmaceutically acceptable salt thereof, or derivative thereof can be used as an adjunct therapy to a conventional treatment regimen for a chronic pain condition to alleviate breakthrough pain. In certain embodiments, the invention also provides a formulation for use as an anesthetic premedication, for the induction of anesthesia, for use as a sedative and/or for the treatment of anxiety.

Sublingual administration of fentanyl, a pharmaceutically acceptable salt thereof, or derivative thereof, in accordance with the present invention may be particularly beneficial in the patient with cancer who is unable to tolerate oral administration because of nausea and vomiting, dysphagia as a result of disease, or parenteral administration because of decreased venous access, emaciation, or coagulation defects. Sublingual administration of fentanyl in accordance with the present invention preferably has potential advantages of even greater ease of use and rapid onset of pain relief action. Furthermore, because sublingual venous drainage is systemic rather than portal, hepatic first-pass elimination may be avoided. The present invention preferably provides therapeutic formulations and methods for solutions of fentanyl, a pharmaceutically acceptable salt thereof, or derivative thereof to be delivered by sublingual spray pumps.

In certain preferred embodiments, the sublingual administration of fentanyl, a pharmaceutically acceptable salt thereof, or derivative thereof, is advantageous over other forms of administration in that it does not require injection using a syringe and needle, it avoids necrosis that can accompany i.m. administration of drugs, and it avoids the need to constantly suck on a lozenge or lollipop. Preferably the sublingual administration of fentanyl, a pharmaceutically acceptable salt thereof, or derivative thereof, in accordance with the present invention is suitable for self administration.

In preferred embodiments certain embodiments, the formulations of the present invention are advantageous in that propellants such as hydrofluorocarbon propellants such as volatile chlorofluocarbons (e.g. propellant 12), volatile hydrofluoroalkanes (e.g. 1,1,1,2-tetrafluoroethane and 1,1,1,2,3,3,3-heptafluoro-n-propane) and volatile alkanes (e.g. propane, butane) are not required to deliver the fentanyl, a pharmaceutically acceptable salt thereof, or derivative thereof, sublingually to the patient.

Preferably the formulations of the present invention are delivered as liquid droplets having a mean diameter of at least about 10 microns, preferably at least about 20 microns, more preferably a mean diameter of from about 20 to about 200 microns. Most preferably the formulations are delivered as liquid droplets have a size distribution of from about 5 microns to about 500 microns, preferably from about 10 microns to about 200 microns, preferably from about 20 microns to about 100 microns, more preferably from about 30 microns to about 70 microns.

Preferably the delivery of the formulation of the present invention to the sublingual mucosa via spray results in a rapid onset of therapeutic effect of the fentanyl, a pharmaceutically acceptable salt thereof, or derivative thereof. For example, in certain embodiments the formulations of the present invention provide a mean time to maximum plasma concentration ($T_{max}$) of fentanyl at from about 5 minutes to about 120 minutes, preferably at from about 10 to about 60 minutes, and more preferably at from about 15 to about 35 minutes after sublingual administration to humans.

In certain further embodiments the formulations of the present invention provide a mean maximum plasma concentration ($C_{max}$) of fentanyl of about 127 pg/ml to about 213 pg/ml per 100 µg fentanyl, preferably about 142 pg/ml to about 195 pg/ml per 100 µg fentanyl, more preferably about 158 pg/ml to about 177 pg/ml per 100 µg fentanyl after sublingual administration to humans.

In certain further embodiments the formulations of the present invention provide a mean maximum plasma concentration ($C_{max}$) of fentanyl of about 137 pg/ml to about 207 pg/ml based on a 100 µg fentanyl dose, preferably about 154 pg/ml to about 190 pg/ml based on a 100 µg fentanyl dose, more preferably about 163 pg/ml to about 181 pg/ml based on a 100 µg fentanyl dose after sublingual administration to humans.

In certain further embodiments the formulations of the present invention provide a mean maximum plasma concentration ($C_{max}$) of fentanyl of about 566 pg/ml to about 850 pg/ml based on a 400 µg fentanyl dose, preferably about 637 pg/ml to about 779 pg/ml based on a 400 µg fentanyl dose, more preferably about 672 pg/ml to about 744 pg/ml based on a 400 µg fentanyl dose after sublingual administration to humans.

In certain further embodiments the formulations of the present invention provide a mean maximum plasma concentration ($C_{max}$) of fentanyl of about 1016 pg/ml to about 1525 pg/ml based on a 800 µg fentanyl dose, preferably about 1143 pg/ml to about 1398 pg/ml based on a 800 µg fentanyl dose, more preferably about 1206 pg/ml to about 1334 pg/ml based on a 800 µg fentanyl dose after sublingual administration to humans.

In certain further embodiments the formulations of the present invention provide an area under the plasma concentration time curve to infinity ($AUC_\infty$) of fentanyl of about 572 pg·h/ml to about 1273 pg·h/ml per 100 µg fentanyl, preferably about 644 pg·h/ml to about 1167 pg·h/ml per 100 µg fentanyl, more preferably about 715 pg·h/ml to about 1061 pg·h/ml per 100 µg fentanyl after sublingual administration to humans.

In certain further embodiments the formulations of the present invention provide an area under the plasma concentration time curve to infinity ($AUC_\infty$) of fentanyl of about 654 pg·h/ml to about 982 pg·h/ml based on a 100 µg fentanyl dose, preferably about 736 pg·h/ml to about 900 pg·h/ml based on a 100 µg fentanyl dose, more preferably about 777 pg·h/ml to about 859 pg·h/ml based on a 100 µg fentanyl dose after sublingual administration to humans.

In certain further embodiments the formulations of the present invention provide an area under the plasma concentration time curve to infinity ($AUC_\infty$) of fentanyl of about 3394 pg·h/ml to about 5092 pg·h/ml based on a 400 µg fentanyl dose, preferably about 3818 pg·h/ml to about 4667 pg·h/ml based on a 400 pg fentanyl dose, more preferably about 4030 pg·h/ml to about 4455 pg·h/ml based on a 400 µg fentanyl dose after sublingual administration to humans.

In certain further embodiments the formulations of the present invention provide an area under the plasma concentration time curve to infinity ($AUC_\infty$) of fentanyl of about 4581 pg·h/ml to about 6873 pg·h/ml based on a 800 µg fentanyl dose, preferably about 5154 pg·h/ml to about 6300 pg·h/ml based on a 800 µg fentanyl dose, more preferably about 5440 pg·h/ml to about 6014 pg·h/ml based on a 800 µg fentanyl dose after sublingual administration to humans.

In certain further embodiments the formulations of the present invention provide an area under the plasma concentration time curve from zero to the time of the last quantifiable plasma concentration ($AUC_T$) of fentanyl of about 378 pg·h/ml to about 1067 pg·h/ml per 100 µg fentanyl, preferably about 425 pg·h/ml to about 978 pg·h/ml per 100 µg fentanyl, more preferably about 472 pg·h/ml to about 889 pg·h/ml per 100 µg fentanyl after sublingual administration to humans.

In certain further embodiments the formulations of the present invention provide an area under the plasma concentration time curve from zero to the time of the last quantifiable plasma concentration ($AUC_T$) of fentanyl of about 378 pg·h/ml to about 568 pg·h/ml based on a 100 µg fentanyl dose, preferably about 425 pg·h/ml to about 520 pg·h/ml based on a 100 µg fentanyl dose, more preferably about 448 pg·h/ml to about 497 pg·h/ml based on a 100 µg fentanyl dose after sublingual administration to humans.

In certain further embodiments the formulations of the present invention provide an area under the plasma concentration time curve from zero to the time of the last quantifiable plasma concentration ($AUC_T$) of fentanyl of about 2844 pg·h/ml to about 4268 pg·h/ml based on a 400 µg fentanyl dose, preferably about 3200 pg·h/ml to about 3912 pg·h/ml based on a 400 μg fentanyl dose, more preferably about 3378 pg·h/ml to about 3734 pg·h/ml based on a 400 μg fentanyl dose after sublingual administration to humans.

In certain embodiments, an increase in pH of the formulations increases absorption.

In certain other embodiments, an increase in temperature increases absorption.

In certain further embodiments the formulations of the present invention provide an area under the plasma concentration time curve from zero to the time of the last quantifiable plasma concentration ($AUC_T$) of fentanyl of about 4333 pg·h/ml to about 6501 pg·h/ml based on a 800 μg fentanyl dose, preferably about 4875 pg·h/ml to about 5960 pg·h/ml based on a 800 μg fentanyl dose, more preferably about 5146 pg·h/ml to about 5689 pg·h/ml based on a 800 μg fentanyl dose after sublingual administration to humans.

Preferably the fentanyl, a pharmaceutically acceptable salt thereof, or derivative thereof, is dissolved in an organic solvent. Examples of organic solvents that may be used to enhance the solubility of fentanyl, or the pharmaceutically acceptable salt thereof in a carrier such as e.g., water, include for example and without limitation: lower alcohols (e.g. $C_{1-4}$ alcohols) such as methanol, ethanol, propyl alcohol, or butyl alcohol; $C_{2-8}$ alcohols having two or three hydroxyl groups, preferably glycerol, propylene glycol or butylene glycol; and polyethylene glycols such as $PEG_{200}$ and $PEG_{400}$ and the like. Mixtures of any of the aforementioned solvents may be used. In certain embodiments, the solvent is a non-polar hydrocarbon, preferably a $C_{7-18}$ hydrocarbon of a linear or branched configuration, its alcohols, fatty acid esters, and triglycerides, such as miglyol. In certain preferred embodiments the organic solvent is ethanol, propylene glycol, polyethylene glycol, or combination thereof.

Preferably the amount of organic solvent for inclusion in the formulation is at least an amount of organic solvent necessary to adequately solubilize the fentanyl, a pharmaceutically acceptable salt thereof, or derivative thereof, such that the fentanyl remains in solution and does not precipitate out.

In certain embodiments, the organic solvent is included in the formulation in an amount of from about 0% to about 99.9% by weight of the formulation, preferably from about 10% to about 80% by weight of the formulation, more preferably from about 20% to about 60% by weight of the formulation.

In certain embodiments, the compositions comprise a $C_{2-8}$ alcohol such as propylene glycol, or a polyethylene glycol and/or polypropylene glycol of an average molar weight of 200 to 4000, or a mixture thereof, in addition to the organic solvent described above. The $C_{2-8}$ alcohol may act as a cosolvent in combination with the organic solvent. Polyethylene glycols commercially available as Carbowax® (Carbowax is a registered trademark of Union Carbide Corporation; e.g., Carbowax® 300 of a molar weight of 300), can be used.

In certain embodiments, the solvent is a cosolvent which includes any of the solvents mentioned herein. In certain preferred embodiments, the cosolvent includes ethanol, propylene glycol, polyethylene glycol, labrosol, labrafil, transcutol, or combination thereof In certain preferred embodiments, the composition according to the invention comprises from about 0.0001% to about 20% by weight of fentanyl, a pharmaceutically acceptable salt thereof, or derivative thereof; from about 1% to about 99% by weight of organic solvent; and from about 0.01% to about 50% by weight of $C_{2-8}$ alcohol.

In certain preferred embodiments, the composition according to the invention comprises from about 0.001% to about 15% by weight of fentanyl, a pharmaceutically acceptable salt thereof, or derivative thereof; from about 5% to 90% by weight of ethanol; and from about 0.1% to 40% by weight of propylene glycol.

In certain preferred embodiments, the composition according to the invention comprises from about 0.01% to about 10% by weight of fentanyl, a pharmaceutically acceptable salt thereof, or derivative thereof; from about 10% to about 80% by weight of ethanol; and from about 1% to about 30% by weight of propylene glycol.

In certain preferred embodiments, the composition according to the invention comprises from about 0.1% to about 0.8% by weight of fentanyl, a pharmaceutically acceptable salt thereof, or derivative thereof; from about 20% to about 60% by weight of ethanol; and from about 4% to about 6% by weight of propylene glycol.

In certain preferred embodiments, the composition according to the invention comprises in a 1 ml volume: from about 100 μg/ml to about 800 μg/ml fentanyl base, about 50% ethanol, about 5.2% propylene glycol, and water qs to 1 ml.

In certain embodiments the fentanyl is employed in the form of a pharmaceutically acceptable salt. Examples of suitable salt forms of fentanyl for use in accordance with the present invention include for example and without limitation, the hydrochloride, chloride, sulphate, tartrate, or citrate salt forms. In certain preferred embodiments, the fentanyl is employed as the free base in the formulations of the present invention.

In certain preferred embodiments, the fentanyl, pharmaceutically acceptable salt thereof, or derivative thereof, will be employed in the formulation at a concentration of from about 0.05 mg/ml to about 15 mg/ml, preferably from about 0.1 mg/ml to about 10 mg/ml, more preferably from about 1 mg/ml to about 8 mg/ml (where weight is expressed as weight of fentanyl free base).

In certain preferred embodiments, the amount of fentanyl, pharmaceutically acceptable salt thereof, or derivative thereof; delivered per unit dose is about 10 μg to about 10 mg, preferably from about 25 μg to about 5 mg, more preferably from about 50 μg to about 1600 μg.

In preferred embodiments of the present invention, the formulation is a solution. In certain alternate embodiments, the formulation is a suspension. When the formulation of the present invention is a suspension, it may be necessary to shake the composition prior to spraying.

In certain preferred embodiments, after the fentanyl, a pharmaceutically acceptable salt thereof, or derivative thereof, is dissolved in the organic solvent, the formulation is preferably included into a liquid carrier for the delivery of the fentanyl, a pharmaceutically acceptable salt thereof, or derivative thereof, via a spray device.

Pharmaceutically acceptable carriers include but are not limited to water, buffer, saline, buffered saline, dextrose solution, propylene glycol, polyethylene glycols, miglyol, and the like. In a specific embodiment, a carrier that may be used in the pharmaceutical formulation of the present invention is phosphate buffered saline, or a buffered saline. In certain preferred embodiments the carrier is water. In certain embodiments, the water in the formulation is present in the form of an aqueous buffer. The buffer is preferably adapted to stabilize the pH of the formulation at pH of about 5 to about 12, preferably at pH of about 6 to about 10, more preferably from about 8 to about 9.5. Buffer systems for use in accordance with the present invention include for example and without limitation sodium acetate/acetic acid, ammonium acetate/disodium edentate, boric acid/sodium hydroxide, orthophosphoric acid/sodium hydroxide, sodium hydrogen carbonate/sodium carbonate, disodium hydrogen orthophosphate/citric acid, and the like.

Other components such as preservatives, antioxidants, surfactants, absorption enhancers, viscosity enhancers or film forming polymers, bulking agents, diluents, coloring agents, flavoring agents, pH modifiers, sweeteners or taste-masking agents may also be incorporated into the composition. Suitable coloring agents include red, black and yellow iron oxides and FD&C dyes such as FD&C Blue No. 2, FD&C Red No. 40, and the like. Suitable flavoring agents include mint, raspberry, licorice, orange, lemon, grapefruit, caramel, vanilla, cherry grape flavors, combinations thereof, and the like. Suitable pH modifiers include citric acid, tartaric acid, phosphoric acid, hydrochloric acid, maleic acid, sodium hydroxide, and the like. Suitable sweeteners include aspartame, acesulfame K, thaumatic, and the like. Suitable taste-masking agents include sodium bicarbonate, ion-exchange resins, cyclodextrin inclusion compounds, adsorbates, and the like.

Absorption enhancers for use in accordance with the present invention include, for example, polysorbates, sorbitan esters, poloxamer block copolymers, PEG-35 castor oil, PEG-40 hydrogenated castor oil, caprylocaproyl macrogol-8 glycerides, PEG-8 caprylic/capric glycerides, sodium lauryl sulfate, dioctyl sulfosuccinate, polyethylene lauryl ether, ethoxydiglycol, propylene glycol mono-di-caprylate, glycerol monocaprylate, glyceryl fatty acids ($C_8$-$C_{18}$) ethoxylated, oleic acid, linoleic acid, glyceryl caprylate/caprate, glyceryl monooleate, glyceryl monolaurate, caprylic/capric triglycerides, ethoxylated nonylphenols, PEG-(8-50) stearates, olive oil PEG-6 esters, triolein PEG-6 esters, lecithin, d-alpha tocopheryl polyethylene glycol 1000 succinate, polycarbonate, sodium glycocholate, sodium taurocholate, cyclodextrins, citric acid, sodium citrate, triacetin, combinations thereof, and the like. In certain preferred embodiments, the absorption enhancer is triacetin. In certain preferred embodiments wherein an absorption enhancer is included in the formulation, the absorption enhancer is included in an amount of from about 0.001% to about 10% by weight of the formulation, preferably in an amount of about 0.01% to about 5% by weight of the formulation.

Bulking agents for use in accordance with the present invention include for example, microcrystalline cellulose, mannitol, xylitol, starches and the like. In certain preferred embodiments, the bulking agent is mannitol. In certain preferred embodiments wherein bulking agent is included in the formulation, the bulking agent is included in an amount of from about 0.001% to about 10% by weight of the formulation, preferably in an amount of about 0.01% to about 5% by weight of the formulation.

Film-forming polymers for use in accordance with the present invention may serve for decreasing the fineness of the spray, the spraying angle and preferably the spreading by increasing the viscosity of the composition. As film-forming polymer, gellan gum, xantham gum, carboxymethyl cellulose, hydroxypropyl cellulose, hydroxyethyl cellulose, hydroxypropyl methylcellulose, methylcellulose, ethylcellulose, gelucire, poloxamers, alginic acid, propyleneglycol ester, polyvinyl alcohol (PVA), polyvinylpyrrolidone (PVP), PVP/PVA copolymer, lubrajel, carboxyvinyl polymer, acrylic acid polymers and copolymers, methacrylic acid, methyl acrylate, ethyl acrylate, methyl methacrylate, ethyl methacrylate, combinations thereof and the like can be used. In certain embodiments, an increase in the viscosity of the solution using film-forming polymers or the like provides an increase in the droplet size when administered from the spray device. The chemistry of the polymer and the molecular weight of the polymer may also influence the diameter of the droplets.

In certain embodiments, the formulations according to the invention are preferably packaged as a bulk solution containing multiple doses in a pump spray system comprising a sealed container fitted with a metering pump.

In certain alternate embodiments the formulations according to the invention are preferably package as a single unit dose solution in a single unit dose pump spray system comprising a sealed container fitted with a pump.

Typically a patient is treated by administration sublingually of 1 to 2 actuations, from the spray pump. Another advantage of sublingual spray delivery is the ability to easily titrate patients by 1 or 2 doses as required by a single actuation. This is typically not the case with other forms of drug delivery (patches, lozenges, tablets, suppositories).

Pump action sprays are characterized in requiring the application of external pressure for actuation, for example, external manual, mechanical or electrically initiated pressure. This is in contrast to pressurized systems, e.g., propellant-driven aerosol sprays, where actuation is typically achieved by controlled release of pressure e.g., by controlled opening of a valve.

In certain embodiments the pump sprays are preferred as the use of a pump spray with the formulation of the present invention allows for the administration of droplets or particles having a mean diameter of at least about 10 microns, preferably at least about 20 microns, more preferably a mean diameter of from about 20 to about 200 microns, and/or preferably having a size distribution of from about 5 microns to about 500 microns, preferably from about 10 microns to about 200 microns, preferably from about 20 microns to about 100 microns, more preferably from about 30 microns to about 70 microns. This is in contrast to a pressurized system which may result in particles less than 5 microns. Liquid droplets or particles having a diameter of less than about 5 microns have the potential to enter into the lungs of a human upon administration. Such entry into the lungs could lead to an increase in patient to patient variability in absorption of the fentanyl. Further, absorption of fentanyl in the lungs could lead to an increased absorption and increased side effects, including respiratory depression which may be fatal.

In certain preferred embodiments, the droplet size of the delivered formulations further provides for an increase in surface area by being sprayed sublingually as opposed to being placed under the tongue with e.g., a dropper.

In certain preferred embodiments, the delivery device is a device such as those described in U.S. Pat. Nos. 6,866,566; 6,877,672; 6,772,915; 6,725,857; 6,705,493; 6,679,248; 6,578,741; 6,527,144; 6,484,715; 6,478,196; 6,461,322; 6,446,839; 6,427,878; 6,367,473; 6,364,166; 6,321,942; 6,234,366; 6,227,413; 6,059,151; 6,059,150; 6,055,979; 5,944,222; 5,901,883; 5,813,570; 4,565,302; 4,532,967; 6,964,381; 6,860,411; 6,824,020; 6,817,490; 6,585,172; 6,443,370; 6,427,680; 6,425,499; 6,401,987; 6,398,074; 6,264,065; 5,950,877; 5,328,099; 5,301,846; and the like which are described in certain embodiments as being suitable for nasal administration.

Other devices suitable for use in accordance with the formulations of the present invention are described in U.S. Pat. Nos. 6,808,085; 6,736,293; 6,732,955; 6,708,846; 6,626,379; 6,626,330; 6,626,328; 6,454,185; 6,427,876; 6,427,684; 6,419,167; 6,405,903; 6,352,181; 6,308,867; 6,257,461; 6,257,454; 6,250,509; 6,227,415; 6,209,760; 6,179,164; 6,109,547; 6,062,430; 6,026,992; 5,992,704; 5,992,703; 5,988,449; 5,967,369; 5,964,417; 5,950,879; 5,938,125;

5,927,559; 5,921,444; 5,893,484; 5,875,938; 5,862,962; 5,860,567; 5,816,504; 5,813,570; 5,803,311; 5,791,518; 5,692,650; 5,655,689; 5,584,417; 5,520,337; 5,519,980; 5,482,193; 5,469,989; 5,443,185; 5,439,177; 5,437,398; 5,427,280; 5,395,032; 5,375,745; 5,368,201; 5,366,122; 5,366,122; 5,335,823; 5,326,000; 5,323,936; 5,316,198; 5,301,841; 5,295,628; 5,289,946; 5,277,334; 5,257,726; 5,228,586; 5,209,375; 5,203,840; 5,147,087; 5,115,980; 5,110,052; 5,011,046; 4,958,752; 4,946,069; 4,944,430; 4,934,568; 4,921,142; 4,871,092; 4,830,284; 4,826,048; 4,823,991; 4,821,923; 4,817,829; 4,776,498; 4,762,475; 4,728,008; 4,726,747; 4,694,977; 4,694,976; 4,566,611; 6,851,583; 6,824,021; 6,779,690; 6,776,312; 6,971,559; 6,948,640; 6,945,473; 6,938,802; 6,933,850; 6,929,156; 6,918,514; 6,913,205; 6,866,168; 6,832,072; 6,830,163; 6,817,490; 6,817,489; 6,811,060; 6,811,057; 6,805,301; 6,805,263; 6,789,750; 6,789,706; 6,786,369; 6,783,035; 6,772,913; 6,769,579; 6,758,371; 6,752,298; 6,742,677; 6,705,062; 6,698,627; 6,698,623; 6,663,019; 6,659,314; 6,659,307; 6,655,550; 6,655,549; 6,651,846; 6,601,735; 6,595,395; 6,592,010; 6,588,629; 6,581,852; 6,571,991; 6,554,160; 6,536,635; 6,527,149; 6,527,148; 6,488,185; 6,471,097; 6,460,781; 6,460,740; 6,460,738; 6,446,841; 6,422,429; 6,409,049; 6,398,079; 6,360,919; 6,349,856; 6,345,737; 6,343,722; 6,662,561; 6,315,169; 6,273,303; 6,273,300; 6,261,274; 6,257,457; 6,234,363; 6,234,168; 6,221,054; 6,209,759; 6,189,741; 6,186,371; 6,155,496; 6,119,897; 6,105,826; 6,021,930; 6,012,615; 5,988,496; 5,950,871; 5,931,386; 5,850,948; 5,803,318; 5,799,810; 5,769,325; RE35,683; 5,692,492; 5,568,884; 5,566,865; 5,511,698; 5,482,188; 5,476,198; 5,366,115; 5,337,923; 5,249,713; 5,237,797; 5,234,135; 5,226,563; 5,190,192; 5,176,296; 5,127,548; 4,966,313; 491,840; 4,245,967; 4,030,667; and the like.

All of the patents recited herein are hereby incorporated by reference in their entireties. Although the delivery devices disclosed in the patents described above may be suitable for nasal or inhalation administration, in accordance with certain embodiments of the present invention the delivery devices are specifically adapted to be suitable for sublingual administration of a liquid formulation. In certain embodiments, the devices utilized to practice the present invention include components made from Pfeiffer of America, Inc., for example, Pfeiffer of America, Inc. sublingual unit dose device article reference number 72772. In other embodiments, the device is Pfeiffer of America, Inc., sublingual unit dose applicator assembly.

Preferably the device in accordance with the present invention is adapted to sublingually deliver the sublingual formulation in a controlled manner preferably such that only droplets having a mean diameter of at least about 10 microns, preferably at least about 20 microns, more preferably a mean diameter of from about 20 to about 200 microns are delivered to the patient. More preferably only droplets having a size distribution in the range of from about 5 microns to about 500 microns, preferably from about 10 microns to about 200 microns, preferably from about 20 microns to about 100 microns, more preferably from about 30 microns to about 70 microns.

Preferably the dispenser is constructed in such a way that it can be carried and simultaneously reliably operated with the fingers, or with three fingers of one hand, and can be used, for example, in the manner of a sublingual spray. The dispenser can be constructed as a disposable dispenser which, following the emptying of the medium chamber, does not have to be refilled and can therefore be constructed as a simple standard component, which receives the pump, the formulation, the channels and optionally, valves or closures within an outer casing, which in side view can be roughly T-shaped or Y-shaped.

If the dispenser is to be emptied in a single pump stroke in successive portions or in one complete pump stroke, and is not to be refilled, then the dispenser can be substantially tightly closed with respect to the outside in the starting position In certain preferred embodiments, the delivery device (e.g., such as a spray pump device) includes a lock-out mechanism. Preferably the lock-out mechanism allows for administration of only one unit dose, and preferably prevents abuse of the fentanyl, a pharmaceutically acceptable salt thereof, or derivative thereof, by only allowing for the administration of one dose and locking out of further administration for a certain and/or predetermined period of time. In certain embodiments, after one or more actuating cycles the actuator can be automatically transferred into the locking position, so that for performing a following actuating cycle randomly or deliberately a release must take place. Locking can take place in the starting position, actuating position and/or an intermediate position and can act both against actuation and against return or against one of these movements alone and several locking positions with the same or different locking action are possible.

In certain embodiments, the device may be premetered or alternatively, the device may be device-metered. Premetered devices preferably contain previously measured doses or a dose fraction in some type of units (e.g., single unit dose amount of solution, single or multiple blisters or other cavities) that may be included in the device during manufacture or by the patient before use. Typical device-metered units have a reservoir containing formulation sufficient for multiple doses that are delivered as metered sprays by the device itself when activated by the patient.

Important factors to consider with manufacture of the device are the reproducibility of the dose, the spray plume, and the particle/droplet size distribution, which can affect the delivery of the fentanyl, a pharmaceutically acceptable salt thereof, or derivative thereof, under the tongue. Maintaining the reproducibility of these parameters through the expiration dating period and ensuring the functionality of the device (e.g., spray mechanism, electronic features, sensors) through its lifetime under patient-use conditions is important as any alteration in these parameters could lead to variability in dosing and absorption, which could lead to potential side effects.

The administered dose of spray drug formulation may be dependent on the design, reproducibility, and performance characteristics of the container closure system. A suitable device which provides the desired droplet/particle size distribution is an important factor for the correct performance of the fentanyl product. Actuation parameters (e.g., force, speed, hold and return times) should also be considered with respect to the device. Moreover, the device should be compatible with formulation components. Further, the device should be designed to prevent partial metering of the fentanyl, a pharmaceutically acceptable salt thereof, or derivative thereof, formulation when used according to the patient instructions for use.

A typical device includes a base unit, a discharge actuator, an orifice for the formulation to be release from the device, and a medium reservoir. Preferably a reservoir is provided which as a dispensing chamber is filled already on production of the device. The medium reservoir preferably defines a measured content of fentanyl, a pharmaceutically acceptable salt thereof, or derivative thereof, to be discharged upon a single activation.

In accordance with certain embodiments of the invention, a reservoir, or a space thereof receiving the medium is preferably an elongated shape preferably having a wall thickness which is constant over the circumference and length of the reservoir body. The reservoir body may be formed simply by a section of a cylindrical hollow of a plastics, steel, such as stainless steel, transparent material, such as glass, or the like so that its production is very simple.

Preferably an actuator body is provided on a unit of the device, which is movable relative to the orifice for activating discharge. This body, in the course of the actuating movement, opens a closure of a chamber, e.g. by puncturing. The space within this chamber may directly adjoin the medium in the reservoir, accommodate the opening body or the reservoir at least in part and configured as a pressure space which prior to being opened is at an elevated pressure. The opening body may be formed directly by the reservoir.

Preferably during a part of the actuating travel following the starting position an elevated pressure is built up. In a subsequent portion of the actuating movement continuing in the same direction, the medium is relieved of the pressure at one of the sides and communicated to the medium orifice on this side. As such, due to the pressure acting on the side, the medium is pushed from the reservoir and through the orifice.

Typically as the liquid formulation leaves the orifice, the liquid droplets follow a trajectory which is influenced by the orifice shape of the device. In certain embodiments, the droplet size, spray geometry, and the spray pattern are dependent on the design of the pump and/or the properties of the formulation. In certain embodiments, the orientation of the actuator, pump design, and the properties of the formulation will influence the spray symmetry and the shape.

In certain embodiments, the device of the present invention further includes a stopper. Preferably the stopper comprises a material which precludes or substantially precludes the absorption of the fentanyl, pharmaceutically acceptable salt thereof, or derivative thereof. A suitable stopper for use in accordance with the device of the present invention is, for example, a stopper marketed by West Pharmaceutical Services, Inc. In certain preferred embodiments, the stopper has the following composition and characteristic: 1) elastomer: bromobutyl and/or chlorobutyl; 2) reinforcement: inert material; and 3) curing system: unconventional.

In certain embodiments, the device further includes a gasket. Preferably the gasket comprises a material which precludes or substantially precludes the absorption of the fentanyl, pharmaceutically acceptable salt thereof, or derivative thereof. A suitable gasket for use in accordance with the device of the present invention is, for example, a stopper marketed by West Pharmaceutical Services, Inc. In certain preferred embodiments, the gasket has the following composition and characteristic: 1) elastomer: bromobutyl and/or chlorobutyl; 2) reinforcement: inert material; and 3) curing system: unconventional.

Droplet size distribution can be determined by utilizing any reliable method known to one of skill in the art. One such method uses laser diffraction devices, such as, for example, the Malvern® (Malvern is a registered trademark of Malvern Instruments Limited) Spraytec® with RT Sizer Software. A Malvern® Mastersizer® (Mastersizer is a registered trademark of Malvern Instruments Limited) S, by Malvern® Instruments Limited (U.K.), device may also be used to determine size distribution. A Malvern® Mastersizer® S is a modular particle size analyzer offering measurement versatility. It can measure spray droplet size as well as wet and dry samples. Particles from sub-micron to a few millimeters may be measured with the Malvern® Mastersizer® S.

Further, automated actuation stations for comparative in vitro bioequivalence tests or other testing to decrease the variability associated with manual actuation may also be used when determining the droplet size distribution. Any such automated actuation stations known to one of skill may be applicable in practicing the present invention. An example of one such device is the MightyRunt Actuation Station by Innova Systems, Inc. In a preferred embodiment, a MightyRunt is equipped with an exhaust fan attachment. In a further embodiment, the MightyRunt is further equipped with a Mettler Toledo® (Mettler Toledo is a registered trademark of Mettler-Toledo AG) balance Model AT201.

Other Active Agents

Although the invention described herein has been described with respect to fentanyl, a pharmaceutically acceptable salt thereof, or derivative thereof, it is contemplated that other active pharmaceutical agents, particularly those suitable for sublingual administration, may be used in accordance with the present invention. For example, in certain embodiments, other opioid analgesics which are suitable for sublingual administration may be used in place of the fentanyl, pharmaceutically acceptable salt thereof, or derivative thereof. Certain opioid analgesics for use in accordance with the present invention include, for example and without limitation, alfentanil, sufentanil, buprenorphine, butorphanol, codeine, hydrocodone, hydromorphone, levorphanol, meperidine, methadone, morphine, nalbuphine, oxycodone, oxymorphone, propoxyphene, tramadol, and the like.

In certain embodiments the active compound is an analgesic, opioid antagonist, anti-migraine agent, anti-emetic agent, anti-epileptic agent, anti-hypertensive agent, anesthetic agent, cannabinoid, cannabinoid antagonist, inverse agonist of cannabinoid, endocannabinoid, enkephalin, analogues or derivatives thereof, or mixtures thereof.

Analgesics useful in the present invention include, but are not limited to, alfentanil, buprenorphine, butorphanol, codeine, fenpipramide, hydrocodone, hydromorphone, levorphanol, meperidine, methadone, morphine, nalbuphine, oxycodone, oxymorphone, pentazocine, piritramide, propoxyphene, sufentanil, tilidine, tramadol, analogues or derivatives thereof, or mixtures thereof.

Opioid antagonists useful in the present invention include, but are not limited to, naloxone, naltrexone, nalmefene, analogues or derivatives thereof, or mixtures thereof.

Anti-migraine agents useful in the present invention include, but are not limited to, almotriptan, eletriptan, frovatriptan, naratriptan, rizatriptan, sumatriptan, zolmitriptan, ergot alkaloids, proxibarbal, lisuride, methysergide, clonidine, pizotifene, analogues or derivatives thereof, and mixtures thereof.

Anti-emetic agents useful in the present invention include, but are not limited to bromopride, domperidone, granisetron, ondansetron, tropisetron, metoclopramide, pyridoxine, scopolamine, thiethylperazine, analogues or derivatives thereof, or mixtures thereof.

Anti-epileptic agents useful in the present invention include, but are not limited to barbiturates, carbamazepine, ethosuximide, mesuximide, phenyloin, primidone, sultiam, valproic acid, vigabatrine, analogues or derivatives thereof, or mixtures thereof.

Anti-hypertensive agents useful in the present invention include, but are not limited to diltiazem, clonidine, nifedipine, verapamil, isosorbide-5-mononitrate, organic nitrates, agents used in treatment of heart disorders, analogues or derivatives thereof, or mixtures thereof.

Anesthetics useful in the present invention include, but are not limited to benzocaine, bupivacaine, dibucaine, etidocaine, levobupivacaine, lidocaine, mepivacaine, oxybuprocaine, piperocaine, prilocalne; procaine, proparacaine, ropivacaine, tetracaine, xylocalne, desflurane, enflurane, isoflurane, sevoflurane, benzonatate, dyclonine, ketamine, phenol, propofol, analogues or derivatives thereof, or mixtures thereof.

Cannabinoids useful in the present invention include, but are not limited to delta-8-tetrahydrocannabinol, delta-9-tetrahydrocannabinol, cannabidol, olivetol, cannabinol, cannabigerol, nabilone, delta-9-tetrahydro cannabinotic acid, the non-psychotropic cannabinoid 3-dimethylnepty 11 carboxylic acid homologine 8, delta-8-tetrahydrocannabinol, pharmaceutically acceptable salts thereof, complexes thereof, derivatives thereof, or mixtures thereof. A particularly preferred cannabinoid is delta-9-tetrahydrocannabinol, also known as dronabinol.

Further, active agents having a narrow therapeutic index or range (e.g., wherein small variances in blood levels of the drug causes changes in the effectiveness or toxicity of that drug) could be particularly suitable for use in accordance with the present invention. Such active agents include for example and without limitation, digoxin, levothyroxine, aminoglycosides (e.g., gentamycin, tobramycin), antiarrythimics (e.g., procainamide, quinidine), theophylline, antineoplastics, busulfan, methotrexate, 6-MP, carboplatinum, antidepressants (e.g., lithium), anticonvulsants (e.g., phenyloin, carbamazepine, valproate sodium, valproic acid), antipsychotics, anticoagulants (e.g., warfarin), cyclosporine, and the like.

The present invention will now be more fully described with reference to the accompanying examples. It should be understood, however, that the following description is illustrative only and should not be taken in any way as a restriction on the generality of the invention specified above.

DETAILED DESCRIPTION OF PREFERRED EMBODIMENTS

Example 1

In Example 1, a fentanyl sublingual formulation was prepared having a concentration of 0.5 mg/ml. The formulation is listed in Table 1 below:

TABLE 1

| Ingredient | Percent |
|---|---|
| Concentration of Fentanyl Base | percent to make 0.5 mg/ml |
| Ethanol % (v) | 20 |
| Propylene glycol % (v) | 5 |
| DI Water % (v) | QS |

Example 2

In Example 2, a fentanyl sublingual formulation was prepared having a concentration of 0.5 mg/ml. The formulation is listed in Table 2 below:

TABLE 2

| Ingredient | Percent |
|---|---|
| Concentration of Fentanyl Base* | percent to make 0.5 mg/ml |
| Ethanol % (v) | 20 |
| Propylene glycol % (v) | 5 |
| DI Water % (v) | QS |

Contains fentanyl citrate equivalent to 0.5 mg/ml of fentanyl base

Example 3

In Example 3, a fentanyl sublingual formulation was prepared having a concentration of 0.5 mg/ml. The formulation is listed in Table 3 below:

TABLE 3

| Ingredient | Percent |
|---|---|
| Concentration of Fentanyl Base | percent to make 0.5 mg/ml |
| Ethanol % (v) | 20 |
| Propylene glycol % (v) | 5 |
| DI Water % (v) | QS |
| Mannitol % (wt) | 0.3 |
| Tween 80 % (wt) | 0.2 |

Example 4

In Example 4, a fentanyl sublingual formulation was prepared having a concentration of 0.5 mg/ml. The formulation is listed in Table 4 below:

TABLE 4

| Ingredient | Percent |
|---|---|
| Concentration of Fentanyl Base | percent to make 0.5 mg/ml |
| Ethanol % (v) | 20 |
| Propylene glycol % (v) | 5 |
| Buffer % (v) | QS |
| Triacetin % (wt) | 0.5 |

Example 5

In Example 5, a fentanyl sublingual formulation was prepared having a concentration of 0.5 mg/ml. The formulation is listed in Table 5 below:

TABLE 5

| Ingredient | Percent |
|---|---|
| Concentration of Fentanyl Base | percent to make 0.5 mg/ml |
| Ethanol % (v) | QS |
| Propylene glycol % (v) | 5 |
| Miglyol % (v) | 50% |

Preparation of Formulations

Examples 1-5

1. Calculated amount of Fentanyl base or Fentanyl citrate was weighed in a tared glass container.
2. Calculated amount of alcohol was added to the container and mixed to dissolve fentanyl.

3. Propylene glycol was weighed and added to the fentanyl solution.
4. Water or Buffer or Miglyol® (Miglyol is a registered trademark of Cremer Oleo GmbH & Co. KG Limited Liability Partnership) was weighed, added to the fentanyl solution and mixed for 2 mm.
5. Inactive ingredients (Mannitol, Triacetin, or TW80) were added at the end and mixed well.
6. The final solution was vortexed for 3 min. After mixing, the formulations were stored in refrigerator for further studies.

Example 6

In Example 6, three rabbits weighing 2-3 kg were used to study the bioavailability of sublingual administration of Examples 1-5 in comparison to the IV injection of the formulation as a reference. Rabbits were first anesthetized by Isoflurane gas as needed to keep the rabbits immobilized for approximately 15-20 min.

For each formulation, study rabbits received a single dose of 0.1 ml (equivalent to 50 µg of fentanyl base) by sublingual and IV administration. For the sublingual studies, the dose of liquid formulation was administered underneath the tongue using a spray bottle. Blood samples (1 ml per sample) were obtained through a catheter installed inside the ear vein.

Blood samples were collected at zero time baselines and at 5, 10, 20, 45, 60 and 120 min after the single dose. Samples were immediately cooled and plasma was separated by centrifugation within 2-3 hrs of blood collection. Samples were stored at −20° C. until assayed. After recovering from anesthesia, animals were returned to their cages. These animals were rested in cages for at least 5-7 days before they could be reused for further testing.

Plasma Collection & Separation

Blood was collected from rabbits in 3 ml tubes containing 7.5% EDTA and centrifuged at 3,000 RPM for 15 min to remove blood cells and other insoluble material. The plasma was decanted into a silanized tube and kept frozen at −20° C. until assay.

Plasma Extraction

For each plasma sample (0.5 ml), 100 µl of Sufentanil (IS) and 100 µL 5M NaOH (for protein denaturation) were added. The Fentanyl was extracted with 1 ml of 1-chlorobutane by vortex mixing for 15 min. After centrifuging at 12000 RPM for 5 min and freeze-drying for 10 min (to break up any emulsion), the upper organic layer was decanted and evaporated to dryness using a gentle stream of nitrogen. The extraction residue was reconstituted with 100 µl methanol followed by vortex mixing for 5 min and sonicating for 3 min, then a 3 µl volume was injected into the GC-MS system.

Results and Discussion

Plasma Concentration Vs. Time Profiles

Plasma concentration-time profiles of Fentanyl in rabbits following IV and sublingual administration of 0.1 ml (equivalent to 50 µg of fentanyl base) are given in the following tables (Tables 6A-10B).

Tables 6A and 6B provide the plasma concentration-time profiles for Example 1.

TABLE 6A (Example 1 intravenous)

| TIME (min) | R1 (ng/ml) | R2 (ng/ml) | R3 (ng/ml) | GRAND AVG | STD DEV |
|---|---|---|---|---|---|
| 5 | | 785.8012 | 839.9696 | 812.885396 | 38.302813 |
| 10 | | 507.7546 | 715.6065 | 611.680527 | 146.97351 |
| 20 | 737.3449 | 423.5903 | 667.9939 | 609.643027 | 164.81539 |
| 45 | 701.5631 | 482.215 | 382.5801 | 522.119422 | 163.19256 |
| 60 | 562.501 | 554.8479 | 475.4686 | 530.939148 | 48.191101 |
| 90 | 207.5541 | 492.4037 | 429.1217 | 376.359829 | 149.57498 |
| 120 | 214.0297 | | 196.9675 | 205.4986 | 12.064797 |

TABLE 6B (Example 1 sublingual)

| TIME (min) | R1 (ng/ml) | R2 (ng/ml) | R3 (ng/ml) | GRAND AVG | STD DEV |
|---|---|---|---|---|---|
| 5 | | 412.1095 | 370.7992 | 391.454361 | 29.210825 |
| 10 | 205.5274 | 279.3298 | 755.3469 | 413.401352 | 52.186202 |
| 20 | 539.2677 | 627.0507 | 712.6511 | 626.323191 | 86.693973 |
| 45 | | 618.9493 | 387.7606 | 503.35497 | 163.47506 |
| 60 | 349.3563 | 218.14 | 498.3773 | 355.291188 | 140.2129 |
| 90 | 245.8519 | 249.5091 | 231.7688 | 242.376606 | 9.3668848 |
| 120 | 214.1339 | 162.9939 | 199.6146 | 192.247465 | 26.353936 |

In Tables 7A and 7B are the plasma concentration-time profiles for Example 2.

TABLE 7A (Example 2 intravenous)

| TIME (min) | R1 (ng/ml) | R2 (ng/ml) | R3 (ng/ml) | GRAND AVG | STD DEV |
|---|---|---|---|---|---|
| 5 | 671.5152 | 788.2252 | | 729.870183 | 58.35497 |
| 10 | 379.1866 | 617.5517 | 1102 | 699.579446 | 300.73378 |
| 20 | 603.9696 | 407.5375 | | 505.75355 | 98.216024 |
| 45 | 380.9878 | | 292.998 | 336.992901 | 43.994929 |
| 60 | 140.7566 | 266.3611 | 388.5314 | 265.216362 | 101.1569 |
| 90 | 81.06491 | 254.4848 | 334.8012 | 223.450304 | 105.88636 |
| 120 | 95.34888 | 278.7789 | 232.4037 | 202.177147 | 77.875432 |

TABLE 7B (Example 2 sublingual)

| TIME (min) | R1 (ng/ml) | R2 (ng/ml) | R3 (ng/ml) | GRAND AVG | STD DEV |
|---|---|---|---|---|---|
| 5 | 350.2297 | 106.9249 | 337.6856 | 264.946755 | 136.99455 |
| 10 | 373.5822 | 115.1643 | 486.0254 | 324.923935 | 190.15835 |
| 20 | 285.5994 | 294.5517 | 518.5091 | 366.220081 | 131.96212 |
| 45 | 302.7099 | 52.78093 | 359.9483 | 238.479716 | 163.34652 |
| 60 | 118.3915 | 43.02434 | 314.9564 | 158.790737 | 140.39528 |
| 90 | 81.06491 | 43.39148 | | 62.2281947 | 26.639136 |
| 120 | 95.34888 | 35.34888 | 30.68154 | 53.7931034 | 36.063946 |

In Tables 8A and 8B are the plasma concentration-time profiles for Example 3.

TABLE 8A (Example 3 intravenous)

| TIME (min) | R1 (ng/ml) | R2 (ng/ml) | R3 (ng/ml) | GRAND AVG | STD DEV |
|---|---|---|---|---|---|
| 5 | 903.4949 | 1000.205 | 882.0649 | 928.588235 | 51.390778 |
| 10 | 814.3834 | 557.9432 | 484.5233 | 618.949966 | 141.40552 |
| 20 |  | 348.8641 | 309.1785 | 329.021298 | 19.842799 |
| 45 | 120.2677 | 169.7972 | 211.0669 | 167.043949 | 37.119701 |
| 60 | 160.3347 | 121.5882 | 128.9087 | 136.943881 | 16.807631 |
| 90 | 89.85598 | 85.70081 | 92.71197 | 89.4229209 | 2.8786265 |
| 120 |  |  |  |  |  |

TABLE 8B (Example 3 sublingual)

| TIME (min) | R1 (ng/ml) | R2 (ng/ml) | R3 (ng/ml) | GRAND AVG | STD DEV |
|---|---|---|---|---|---|
| 5 |  | 127.3124 | 269.1927 | 198.252535 | 100.32454 |
| 10 | 304.6288 | 589.1684 | 310.5953 | 401.464165 | 162.58397 |
| 20 | 349.3611 | 689.7999 | 281.5365 | 440.232477 | 218.77603 |
| 45 | 288.0639 | 418.1555 | 195.9391 | 300.719518 | 111.64744 |
| 60 | 173.0345 | 255.9016 |  | 214.45 | 74.967507 |
| 90 | 224.432 | 87.7931 | 228.6156 | 180.280257 | 80.123534 |
| 120 | 96.5284 | 145.1907 |  | 120.859533 | 34.409422 |

In Tables 9A and 9B are the plasma concentration-time profiles for Example 4.

TABLE 9A

Example 4 intravenous)

| TIME (min) | R1 (ng/ml) | R2 (ng/ml) | R3 (ng/ml) | GRAND AVG | STD DEV |
|---|---|---|---|---|---|
| 5 | 740.3759 | 732.5855 | 717.8438 | 730.268425 | 11.443374 |
| 10 | 666.2644 | 671.4571 | 627.0568 | 654.926076 | 24.274753 |
| 20 | 713.355 | 592.5 | 638.7444 | 648.199797 | 60.979784 |
| 45 | 575.2667 | 557.7789 | 482.8316 | 538.625761 | 49.103907 |
| 60 | 409.8756 | 596.6278 | 548.1217 | 518.208362 | 96.903054 |
| 90 | 455.8567 | 484.928 | 430.5538 | 457.112801 | 27.208875 |
| 120 | 385.2982 |  | 452.6998 | 418.998986 | 47.660144 |

TABLE 9B (Example 4 sublingual)

| TIME (min) | R1 (ng/ml) | R2 (ng/ml) | R3 (ng/ml) | GRAND AVG | STD DEV |
|---|---|---|---|---|---|
| 5 | 250.8854 | 481.6146 | 459.2779 | 397.259297 | 127.25455 |
| 10 | 478.074 | 577.9594 | 614.8479 | 556.960446 | 70.76361 |
| 20 | 587.8195 | 465.9229 | 518.4341 | 524.058824 | 61.142626 |
| 45 | 538.3245 | 499.217 | 449.574 | 495.705206 | 44.479353 |
| 60 | 367.4361 | 452.9817 | 442.7566 | 421.058147 | 46.718636 |
| 90 | 309.5538 | 571.0487 | 202.8722 | 361.158215 | 189.43533 |
| 120 | 205.6531 | 195.7282 | 427.1927 | 276.191346 | 130.86513 |

In Tables 10A and 10B are the plasma concentration-time profiles for Example 5.

TABLE 10A (Example 5 intravenous)

| TIME (min) | R1 (ng/ml) | R2 (ng/ml) | R3 (ng/ml) | GRAND AVG | STD DEV |
|---|---|---|---|---|---|
| 5 | 928.5193 | 1247.247 | 1123.335 | 1099.70047 | 160.67311 |
| 10 | 920.1521 | 1100.3 | 1103.844 | 1041.43205 | 105.04643 |
| 20 | 876.3793 | 966.998 | 972.8114 | 938.729547 | 54.075067 |
| 45 | 765.9696 | 938.3834 | 947.0609 | 883.804598 | 102.14032 |
| 60 | 645.6045 | 892.6836 | 482.2799 | 673.52265 | 206.62129 |
| 90 | 157.9533 | 418.6034 | 343.0811 | 306.545977 | 134.1109 |
| 120 | 58.43813 | 30.68154 | 30.68154 | 39.933739 | 16.025276 |

TABLE 10B (Example 5 sublingual)

| TIME (min) | R1 (ng/ml) | R2 (ng/ml) | R3 (ng/ml) | GRAND AVG | STD DEV |
|---|---|---|---|---|---|
| 5 | 140.7911 | 176.7338 | 127.357 | 148.293949 | 25.529127 |
| 10 | 239.712 | 191.2956 | 210.8458 | 213.951149 | 24.357082 |
| 20 | 409.5335 | 580.6095 | 540.5842 | 510.242394 | 89.483087 |
| 45 | 351.3955 | 500.9315 | 314.7343 | 389.020453 | 98.636103 |
| 60 | 364.9493 | 439.2885 | 280.645 | 361.62762 | 79.373899 |
| 90 | 245.2698 | 403.4255 | 30.68154 | 226.458925 | 187.08258 |
| 120 | 30.68154 | 119.7079 | 215.6552 | 122.014875 | 92.508392 |

Pharmacokinetic Parameters

The pharmacokinetic parameters Peak plasma concentration (Cmax), Time to reach Cmax(Tmax), Half-life ($t_{1/2}$), Area under the curve (AUC), and Total body clearance (CL) obtained after sublingual or IV drug administrations are tabulated in the following tables (Tables 11-15). Also, plasma concentration-time curves after administering IV and sublingual doses of Fentanyl are shown in FIGS. 1-10.

TABLE 11

| | (Example 1 intravenous and sublingual) | | | | | |
|---|---|---|---|---|---|---|
| ROUTE OF ADMINISTRATION | AUC (min*ng/ml) | $T_{1/2}$ (min) | TMAX (min) | CMAX (ng/ml) | VD (ml) | Cl (ml/min) |
| IV | 71772.86 | 43.8141 | 0 | 812.8854 | 50.7843 | 0.6966 |
| SL | 59684.34 | 55.704 | 20 | 626.3232 | | |

TABLE 12

| | (Example 2 intravenous and sublingual) | | | | | |
|---|---|---|---|---|---|---|
| ROUTE OF ADMINISTRATION | AUC (min*ng/ml) | $T_{1/2}$ (min) | TMAX (min) | CMAX (ng/ml) | VD (ml) | Cl (ml/min) |
| IV | 86790.18 | 153.2372 | 0 | 729.8702 | 181.8356 | 0.9218 |
| SL | 23759.14 | 33.1477 | 20 | 366.2201 | | |

TABLE 13

| | (Example 3 intravenous and sublingual) | | | | | |
|---|---|---|---|---|---|---|
| ROUTE OF ADMINISTRATION | AUC (min*ng/ml) | $T_{1/2}$ (min) | TMAX (min) | CMAX (ng/ml) | VD (ml) | Cl (ml/min) |
| IV | 32707.76 | 49.7523 | 0 | 928.5882 | 78.4776 | 1.5287 |
| SL | 40623.13 | 57.6038 | 20 | 440.2325 | | |

TABLE 14

| | (Example 4 intravenous and sublingual) | | | | | |
|---|---|---|---|---|---|---|
| ROUTE OF ADMINISTRATION | AUC (min * ng/ml) | $T_{1/2}$ (min) | TMAX (min) | CMAX (ng/ml) | VD (ml) | Cl (ml/min) |
| IV | 185485.6 | 200.3556 | 0 | 730.2684 | 77.036 | 0.2696 |
| SL | 86916.91 | 93.4018 | 10 | 556.9604 | | |

TABLE 15

| | (Example 5 intravenous and sublingual) | | | | | |
|---|---|---|---|---|---|---|
| ROUTE OF ADMINISTRATION | AUC (min * ng/ml) | $T_{1/2}$ (min) | TMAX (min) | CMAX (ng/ml) | VD (ml) | Cl (ml/min) |
| IV | 76250.66 | 17.0944 | 0 | 1099.7005 | 27.3544 | 0.6557 |
| SL | 42554.59 | 38.2788 | 20 | 510.2424 | | |

The maximum concentrations were reached in about 20 minutes for all formulations after sublingual administration. There was considerable inter-individual variability by both routes of administration. Measurable plasma concentration after sublingual administration was demonstrable after 120 min in most formulation testing. In conclusion, sublingual fentanyl administration showed good absorption profile compared to IV.

Example 7

In Example 7, a study was conducted to determine the pharmacokinetics of a formulation prepared in accordance with Example 1 after increasing sublingual dose administration in healthy volunteers under fasting conditions. The study was also conducted to determine the safety and tolerability of a fentanyl sublingual spray prepared in accordance with Example 1 in humans.

The study was a single center, single dose, single-blinded, sequential ascending dose and repeated design in healthy male subjects. The following treatments were to be administered under fasting conditions:

Treatment A (Test 1): One Fentanyl 1 mg/ml sublingual spray (1×100 µg dose)
Treatment B (Test 2): One Fentanyl 4 mg/ml sublingual spray (1×400 µg dose)
Treatment C (Test 2): Two Fentanyl 4 mg/ml sublingual spray (1×800 µg dose)
Treatment D (Placebo-Test 1): One Placebo 1 mg/ml sublingual spray (1×100 µg dose)

Treatment E (Placebo-Test 2): One Placebo 4 mg/ml sublingual spray (1×400 µg dose)
Treatment F (Placebo-Test 2): Two Placebo 4 mg/ml sublingual spray (1×800 µg dose)

The products were to be administered to nine (9) healthy male volunteers according to the following design in Table 16 below:

TABLE 16

|  | Period 1 | Period 2 | Period 3 |
|---|---|---|---|
| Sequence 1 (n = 6) | 100 µg | 400 µg | 800 µg |
| Sequence 2 (n = 3) | Placebo | Placebo | Placebo |

In each period, subjects were to arrive at the clinical site at least 10 hours before dosing. After a supervised overnight fast, a single oral dose of the assigned formulation was to be orally administered in the morning. Subjects were allowed to leave the clinical site after the 24-hour blood draw. The wash-out period was to be of at least 14 days; the duration of this study was expected to be approximately 5-6 weeks. As per protocol, each sequential dose was to be separated by a wash-out of at least 14 days, which corresponds to more than 10 time the expected half life of the moiety to be measured.

However, during the study periods 1 and 2 were separated by a wash-out of 15 days and periods of 2 and 3 were separated by a wash-out of 13 days. As fentanyl's expected half life is reported to be approximately 6.4 hours, it is judged that these wash-out deviations should not affect the conclusion of the study. Furthermore, no carry-over was observed at the beginning of the second and third periods.

Pharmacokinetic Assessments

Blood samples for pharmacokinetic measurements were collected prior to and up to 24 hours (serial samplings) after each drug administration. The drug concentrations produced by the administration of the studied formulations were used to derive the pharmacokinetic parameters listed in Tables 17 and 18 below.

Figure 12:
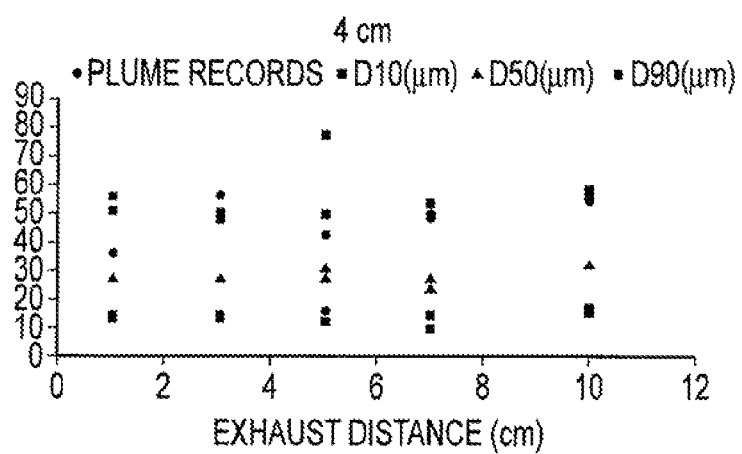
FIG. 12 depicts a graphical summary of Dv10, Dv50, and Dv90 values versus placement at 4 cm device to laser beam for exhaust results.
Figure 13:
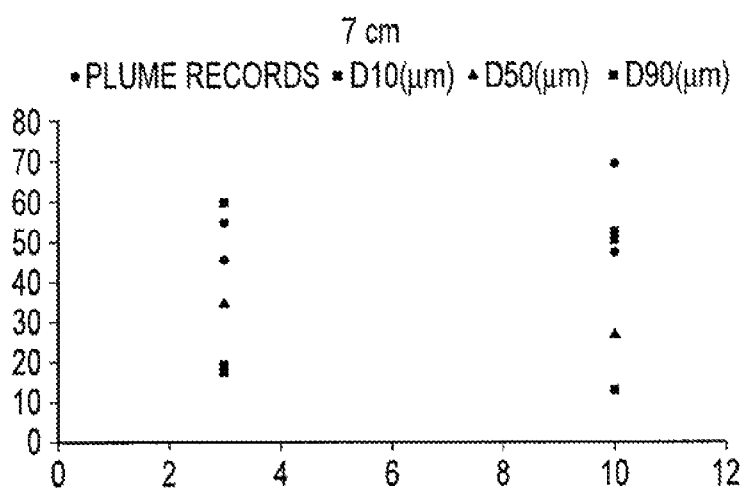
FIG. 13 depicts a graphical summary of Dv10, Dv50, and Dv90 values versus placement at 7 cm device to laser beam for exhaust results.
Figure 14:
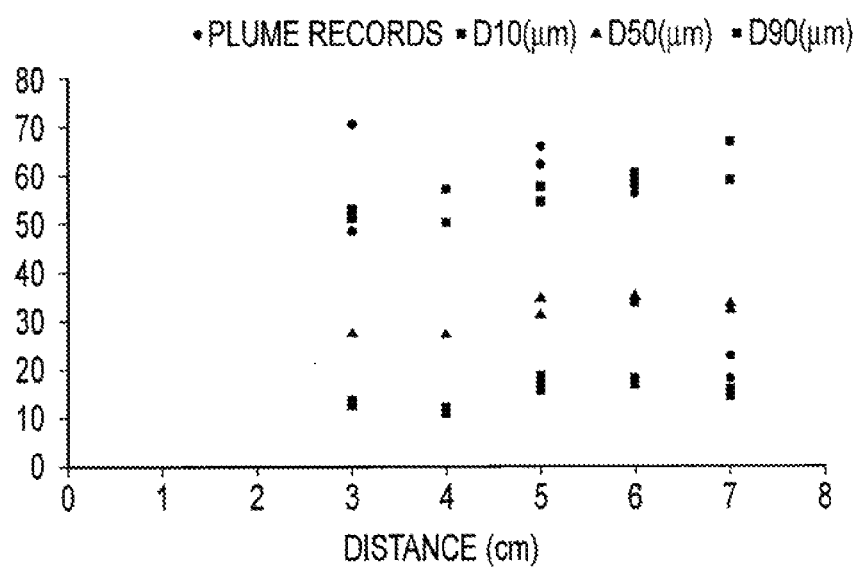
FIG. 14 depicts a graphical summary of device to laser beam placement results for Dv10, Dv50, and Dv90 values versus distance to device to laser beam.

Six (6) subjects were included in the statistical analysis. A summary of the non-normalized pharmacokinetic parameters is presented in Table 17 and a summary of the normalized pharmacokinetic parameters is presented in Table 18. The mean measured plasma concentrations versus time profile, produced by the administration of the Test products, is depicted in FIG. 11, whereas the ln-transformed mean concentrations versus time profile is presented in FIG. 12.

The pharmacokinetic parameters of interest for this study were $C_{max}$, $AUC_\infty$, $AUC_T$, $AUC_{T/\infty}$, $K_{el}$, $T_{max}$, $T_{1/2el}$, Cl/F and $V_z/F$.

TABLE 17

Pharmacokinetic Parameters
Fentanyl (n = 6)
Non-normalized Data

| PARAMETER | TEST 1 (100 µg) n = 6 | | TEST 2 (400 µg) n = 6 | | TEST 2 (800 µg) N = 2 | |
|---|---|---|---|---|---|---|
|  | MEAN | C.V. (%) | MEAN | C.V. (%) | MEAN | C.V. (%) |
| $C_{max}$ (pg/ml) | 172.0 | 27.1 | 708.0 | 50.2 | 1270.4 | 37.7 |
| ln ($C_{max}$) (pg/ml) | 5.1207 | 4.8 | 6.4509 | 8.2 | 7.1102 | 5.4 |
| $T_{max}$ (hours) | 0.50 | 29.7 | 0.50 | 61.3 | 0.75 | 0.0 |
| $AUC_T$ (pg · h/ml) | 472.6 | 66.2 | 3556.1 | 63.0 | 5417.3 | 30.6 |
| ln ($AUC_T$) (pg · h/ml) | 6.0271 | 8.6 | 8.0208 | 7.5 | 8.5734 | 3.6 |
| $AUC_\infty$ (pg · h/ml) | 817.9 | 36.1 | 4242.6 | 57.6 | 5726.8 | 28.8 |
| ln ($AUC_\infty$) (pg · h/ml) | 6.6607 | 4.8 | 8.2303 | 6.4 | 8.6317 | 3.4 |
| $AUC_{T/\infty}$ (%) | 54.90 | 28.7 | 81.48 | 10.6 | 94.35 | 1.8 |
| $K_{el}$ (hour$^{-1}$) | 0.2008 | 27.4 | 0.1593 | 44.9 | 0.1782 | 0.9 |
| $T_{1/2\,el}$ (hours) | 3.70 | 30.4 | 5.20 | 45.8 | 3.89 | 0.9 |
| Cl/F (ml/h/kg) | 1718.8 | 27.7 | 1532.2 | 49.7 | 1837.3 | 13.1 |
| $V_z/F$ (ml/kg) | 9070.2 | 34.7 | 10470.4 | 47.1 | 10307.7 | 12.2 |

For $T_{max}$, the median is presented and the statistical analysis is based on ranks.

TABLE 18

Data Normalized to the 100 µg dose

| PARAMETER | TEST 1 (100 µg) n = 6 | | TEST 2 (400 µg) n = 6 | | TEST 2 (800 µg) N = 2 | |
|---|---|---|---|---|---|---|
|  | MEAN | C.V. (%) | MEAN | C.V. (%) | MEAN | C.V. (%) |
| $C_{max}$ (pg/ml) | 172.0 | 27.1 | 177.0 | 50.2 | 158.8 | 37.7 |
| ln ($C_{max}$) (pg/ml) | 5.1207 | 4.8 | 5.0646 | 10.4 | 5.0307 | 7.7 |
| $T_{max}$ (hours) | 0.50 | 29.7 | 0.50 | 61.3 | 0.75 | 0.0 |
| $AUC_T$ (pg · h/ml) | 472.6 | 66.2 | 889.0[1] | 63.0 | 677.2 | 30.6 |
| ln ($AUC_T$) (pg · h/ml) | 6.0271 | 8.6 | 6.6346[1] | 9.1 | 6.4940 | 4.8 |
| $AUC_\infty$ (pg · h/ml) | 817.9 | 36.1 | 1060.7 | 57.6 | 715.9 | 28.8 |
| ln ($AUC_\infty$) (pg · h/ml) | 6.6607 | 4.8 | 6.8440 | 7.7 | 6.5523 | 4.5 |
| $AUC_{T/\infty}$ (%) | 54.90 | 28.7 | 81.48[2] | 10.6 | 94.35[2] | 1.8 |
| $K_{el}$ (hour$^{-1}$) | 0.2008 | 27.4 | 0.1593 | 44.9 | 0.1782 | 0.9 |
| $T_{1/2el}$ (hours) | 3.70 | 30.4 | 5.20 | 45.8 | 3.89 | 0.9 |
| Cl/F (ml/h/kg) | 1718.8 | 27.7 | 1532.2 | 49.7 | 1837.3 | 13.1 |
| $V_z/F$ (ml/kg) | 9070.2 | 34.7 | 10470.4 | 47.1 | 10307.7 | 12.2 |

TABLE 18-continued

| | Data Normalized to the 100 µg dose | | | | | |
|---|---|---|---|---|---|---|
| | TEST 1 (100 µg) n = 6 | | TEST 2 (400 µg) n = 6 | | TEST 2 (800 µg) N = 2 | |
| PARAMETER | MEAN | C.V. (%) | MEAN | C.V. (%) | MEAN | C.V. (%) |

For $T_{max}$, the median is presented and the statistical analysis is based on ranks.
[1]Different than Test - 1 (p < 0.05)
[2]Different than Test - 1 (p < 0.01)
N.S. = Not Significant (p > 0.05)
Definition of the Pharmacokinetic Parameters
$C_{max}$: Maximum plasma concentration (ng/ml).
$T_{max}$: Time of maximum measured plasma concentration; if it occurs at more than one time point, $T_{max}$ is defined as the first time point with this value (hour).
$C_{LQC}$: Last quantifiable concentration (ng/ml).
$T_{LQC}$: Time of last quantifiable plasma concentration (hour).
$AUC_T$: Cumulative Area Under the plasma concentration time Curve calculated from 0 to $T_{LQC}$ using the Trapezoidal method (ng · h/ml), and calculated according the following equation:

$$AUC_T = \sum_{2}^{N_{TLQC}} \left[\left(\frac{C_{n-1}+C_n}{2}\right) \times (T_n - T_{n-1})\right]$$

Where $N_{TLQC}$ is the number of the sample related to the $T_{LQC}$.
$AUC_\infty$: Extrapolated Area Under the plasma concentration time Curve to infinity (ng · h/ml).

$$AUC_\infty = AUC_T + \left(\frac{C_{LQC}}{K_{el}}\right)$$

$AUC_{T/\infty}$: Relative percentage of $AUC_T$ with respect to $AUC_\infty$ (%).

$$AUC_{T/\infty} = \left(\frac{AUC_T}{AUC_\infty}\right) \times 100$$

$T_{LIN}$: Time point where log-linear elimination begins (hour).
$K_{el}$: Apparent mean elimination rate constant estimated by a non-linear least-squares regression analysis; a minimum of three values are required at the end of the concentration-time curve (hour$^{-1}$).
$T_{1/2el}$: Half-life of elimination (hour).

$$T_{1/2el} = \frac{\ln(2)}{K_{el}}$$

Cl/F: Apparent clearance (ml/h/kg)

$$Cl/F = \frac{Dose^*}{AUC_\infty}$$

$V_Z/F$: Apparent volume of distribution (ml/kg)

$$V_Z/F = \frac{Dose^*}{K_{el} \bullet AUC_\infty}$$

*Dose expressed per weight (kg)

As noted in Table 11, the parameters for which a statistically significant difference was observed between the 100 µg dose and the normalized 400 µg dose was $AUC_T$, $\ln(AUC_T)$ and $AUC_{T/\infty}$ and the parameter for which a statistically significant difference was observed between the 100 µg dose and the normalized 800 µg dose was $AUC_{T/\infty}$. No statistically significant differences were observed for any of the other pharmacokinetic parameters under study.

The mean $C_{max}$ value of the 100 µg dose was 172.0 pg/ml while for the 400 µg dose, it was 708.0 pg/ml and for the 800 µg dose, it was 1270.4 pg/ml. Once normalized to the 100 µg dose, the mean $C_{max}$ value of the 400 µg dose was 177.0 pg/ml and for the 800 µg dose, it was 158.8 pg/ml.

The median $T_{max}$ was 0.50 hour for the 100 µg dose and the 400 µg dose, and 0.75 hour for the 800 µg dose.

The mean $AUC_T$ value of the 100 µg dose was 472.6 pg·h/ml while for the 400 µg dose, it was 3556.1 pg·h/ml and for the 800 µg dose, it was 5417.3 pg·h/ml. Once normalized to the 100 µg dose, the mean $AUC_T$ value of the 400 µg dose was 889.0 pg·h/ml and for the 800 µg dose, it was 677.2 pg·h/ml.

The mean $AUC_\infty$ value of the 100 µg dose was 817.9 pg·h/ml while for the 400 µg dose, it was 4242.6 pg·h/ml and for the 800 µg dose, it was 5726.8 pg·h/ml. Once normalized to the 100 µg dose, the mean $AUC_\infty$ value of the 400 µg dose was 1060.7 pg·h/ml and for the 800 µg dose, it was 715.9 pg·h/ml.

The $AUC_{T/\infty}$ ratio was approximately 55% for the 100 µg dose, 81% for the 400 µg dose and 94% for the 800 µg dose.

The mean $K_{el}$ was 0.2008 hour$^{-1}$ for the 100 µg dose, 0.1593 hour$^{-1}$ for the 400 µg dose and 0.1782 hour$^{-1}$ for the 800 µg dose, while the mean $T_{1/2el}$ value was 3.70 hours, 5.20 hours and 3.89 hours following the same order.

The mean Cl/F was 1718.8 ml/h/kg for the 100 µg dose, 1532.2 ml/h/kg for the 400 µg dose and 1837.3 ml/h/kg for the 800 µg dose, while the mean $V_Z/F$ was 9070.2 ml/kg for the 100 µg dose, was 10470.4 ml/kg for the 400 µg dose and was 10307.7 ml/kg for the 800 µg dose.

The intra-subject variation was 36.79%, 37.05% and 28.88% for $C_{max}$, $AUC_T$, and $AUC_\infty$, respectively.

Safety Evaluation

The safety parameters included the occurrence of adverse effects, measurements of vital signs, respiratory rate, oxygen saturation of blood by finger pulse oximetry, ECG and clinical laboratory parameters.

All adverse events were spontaneously reported by the volunteer, observed by the Clinical Investigator (or delegates) or elicited by general questioning by the clinical staff. Adverse events were also reported upon completion of the form "Taste of Medication Questionnaire to Subject", which was filled right after dosing. For the purposes of the study, the period of observation for each individual subject extended from the time the subject gave informed consent to within 7 days following the last drug administration.

Safety Results:

All nine subjects experienced a total of one-hundred-twenty-seven (127) adverse events during the study. No serious adverse events were recorded in this study. Twenty adverse events (8 different types) were reported after the single dose administration of the Test 1 (A) product, fifty-six adverse events (26 different types) were reported after the single dose administration of the Test 2 (B) product, twenty-two adverse events (19 different types) were reported after the single dose administration of the Test 2 (C) product, ten adverse events (8 different types) were reported after the single dose administration of the Placebo-Test 1 (D) product, eleven adverse events (9 different types) were reported after the single dose administration of the Placebo-Test 2 (E) product and twelve adverse events (8 different types) were reported after the single dose administration of the Placebo-Test 2 (F) product. Two (2) adverse events associated with post-study laboratory test results were imputed to three formulations.

Six subjects (100%) reported adverse events after the administration of the Test 1 (A) formulation, six subjects (100%) reported adverse events after the administration of the Test 2 (13) formulation, two subjects (100%) reported adverse events after the administration of the Test 2 (C) formulation, three subjects (100%) reported adverse events after the administration of the Placebo-Test 1 (D) formulation, three subjects (100%) reported adverse events after the administration of the Placebo-Test 2 (E) formulation and three subjects (100%) reported adverse events after the administration of the Placebo-Test 2 (F) formulation. The adverse events by system Organ Class are listed in Table 19.

The events abdominal distension, abdominal pain, abdominal pain upper, anxiety, depressed mood, diarrhea, disturbance in attention, dizziness (10 episodes out of 11), dry mouth, dry skin, dysgeusia, headache, fatigue (6 episodes out of 7), feeling cold, feeling drunk, feeling hot, feeling of relaxation, hot flush, hyperhidrosis, hypoaesthesia oral, hypoaesthesia, nasal congestion, nausea, oral discomfort, pallor, paresthesia oral, pruritus, sensation of heaviness, somnolence, speech disorder, tongue coated and vomiting were assessed to be possibly related to the drugs. The other events cough, dizziness (1 episode out of 11), fatigue (1 episode out of 7), musculoskeletal pain, rhinorrhoea and throat irritation were assessed to be not related to the study drugs. The other event nasopharyngitis was assessed to be unlikely related to the study drugs.

TABLE 19

Summary of Adverse Events by System Organ Class

| Parameter | Period 1 | | Period 2 | | Period 3 | |
|---|---|---|---|---|---|---|
| | Fentanyl 100 μg | Placebo | Fentanyl 400 μg | Placebo | Fentanyl 800 μg | Placebo |
| Number of subjects exposed | 6 | 3 | 6 | 3 | 2 | 3 |
| Number of subjects reporting at least one adverse event | 6 | 3 | 6 | 3 | 2 | 3 |
| Total number of withdrawals | 0 | 0 | 4 | 0 | 0 | 0 |
| Withdrawals due to adverse event (not related to tested drug) | 0 | 0 | 1 | 0 | 0 | 0 |
| Withdrawals due to adverse event (related to tested drug) | 0 | 0 | 2 | 0 | 0 | 0 |
| Total number of adverse events* | 20 | 10 | 56 | 11 | 22 | 12 |
| Adverse events at least possibly drug related* | 18 | 8 | 53 | 11 | 22 | 12 |

| Nature of adverse events | Number of subjects | % of subjects exposed | Number of subjects | % of subjects exposed | Number of subjects | % of subjects exposed | Number of subjects | % of subjects exposed | Number of subjects | % of subjects exposed | Number of subjects | % of subjects exposed |
|---|---|---|---|---|---|---|---|---|---|---|---|---|
| Gastrointestinal disorders | | | | | | | | | | | | |
| Abdominal distension | 0 | 0 | 0 | 0 | 1 | 17 | 0 | 0 | 0 | 0 | 0 | 0 |
| Abdominal pain | 0 | 0 | 0 | 0 | 0 | 0 | 1 | 33 | 0 | 0 | 1 | 33 |
| Abdominal pain upper | 0 | 0 | 0 | 0 | 1 | 17 | 0 | 0 | 0 | 0 | 0 | 0 |
| Diarrhoea | 0 | 0 | 0 | 0 | 0 | 0 | 1 | 33 | 0 | 0 | 1 | 33 |
| Dry mouth | 0 | 0 | 0 | 0 | 0 | 0 | 0 | 0 | 1 | 50 | 0 | 0 |
| Dysgeusia | 6 | 100 | 3 | 100 | 6 | 100 | 3 | 100 | 2 | 100 | 3 | 100 |
| Hypoaesthesia oral | 4 | 67 | 1 | 33 | 3 | 50 | 1 | 33 | 1 | 50 | 0 | 0 |
| Nausea | 0 | 0 | 0 | 0 | 4 | 67 | 0 | 0 | 1 | 50 | 0 | 0 |
| Oral discomfort | 1 | 17 | 0 | 0 | 1 | 17 | 1 | 33 | 1 | 50 | 0 | 0 |
| Tongue coated | 0 | 0 | 0 | 0 | 1 | 17 | 0 | 0 | 0 | 0 | 0 | 0 |
| Vomiting | 0 | 0 | 0 | 0 | 1 | 17 | 0 | 0 | 1 | 50 | 0 | 0 |
| General disorders and administration site conditions | | | | | | | | | | | | |
| Fatigue | 3 | 50 | 1 | 33 | 2 | 33 | 0 | 0 | 1 | 50 | 0 | 0 |
| Feeling cold | 0 | 0 | 0 | 0 | 1 | 17 | 0 | 0 | 1 | 50 | 0 | 0 |
| Feeling drunk | 0 | 0 | 0 | 0 | 6 | 100 | 0 | 0 | 0 | 0 | 0 | 0 |
| Feeling hot | 0 | 0 | 0 | 0 | 1 | 17 | 0 | 0 | 1 | 50 | 0 | 0 |
| Feeling of relaxation | 3 | 50 | 0 | 0 | 1 | 17 | 0 | 0 | 0 | 0 | 0 | 0 |
| Hyperhidrosis | 0 | 0 | 0 | 0 | 0 | 0 | 0 | 0 | 1 | 50 | 0 | 0 |
| Investigations* | | | | | | | | | | | | |
| Alanine aminotransferase increased | 0 | 0 | 1 | 33 | 0 | 0 | 1 | 33 | 0 | 0 | 1 | 33 |
| Aspartate aminotransferase increased | 0 | 0 | 1 | 33 | 0 | 0 | 1 | 33 | 0 | 0 | 1 | 33 |

TABLE 19-continued

Summary of Adverse Events by System Organ Class

| Parameter | Period 1 | | Period 2 | | Period 3 | |
| --- | --- | --- | --- | --- | --- | --- |
| | Fentanyl 100 µg | Placebo | Fentanyl 400 µg | Placebo | Fentanyl 800 µg | Placebo |
| Musculoskeletal and connective tissue disorders | | | | | | |
| Sensation of heaviness | 0 0 | 0 0 | 1 17 | 0 0 | 0 0 | 0 0 |
| Musculoskeletal pain | 0 0 | 0 0 | 1 17 | 0 0 | 0 0 | 0 0 |
| Nervous system disorders | | | | | | |
| Dizziness | 0 0 | 0 0 | 6 100 | 0 0 | 2 100 | 0 0 |
| Disturbance in attention | 0 0 | 0 0 | 2 33 | 0 0 | 1 50 | 0 0 |
| Headache | 0 0 | 0 0 | 1 17 | 0 0 | 0 0 | 1 33 |
| Hypoaesthesia | 0 0 | 0 0 | 4 67 | 0 0 | 1 50 | 0 0 |
| Paresthesia oral | 0 0 | 1 33 | 3 50 | 1 33 | 0 0 | 3 100 |
| Somnolence | 0 0 | 1 33 | 1 17 | 0 0 | 2 100 | 1 33 |
| Speech disorder | 0 0 | 0 0 | 0 0 | 0 0 | 1 50 | 0 0 |
| Psychiatric disorders | | | | | | |
| Anxiety | 0 0 | 0 0 | 0 0 | 1 33 | 0 0 | 0 0 |
| Depressed mood | 0 0 | 0 0 | 1 17 | 0 0 | 0 0 | 0 0 |
| Respiratory, thoracic and mediastinal disorders | | | | | | |
| Cough | 1 17 | 0 0 | 0 0 | 0 0 | 0 0 | 0 0 |
| Nasal congestion | 1 17 | 0 0 | 1 17 | 0 0 | 0 0 | 0 0 |
| Nasopharyngitis | 0 0 | 1 33 | 0 0 | 0 0 | 0 0 | 0 0 |
| Rhinorrhoea | 1 17 | 0 0 | 0 0 | 0 0 | 0 0 | 0 0 |
| Throat irritation | 0 0 | 0 0 | 1 17 | 0 0 | 0 0 | 0 0 |
| Skin and subcutaneous tissue disorders | | | | | | |
| Dry skin | 0 0 | 0 0 | 0 0 | 0 0 | 1 50 | 0 0 |
| Pallor | 0 0 | 0 0 | 1 17 | 0 0 | 1 50 | 0 0 |
| Pruritus | 0 0 | 0 0 | 0 0 | 0 0 | 1 50 | 0 0 |
| Vascular disorders | | | | | | |
| Hot flush | 0 0 | 0 0 | 3 50 | 0 0 | 1 50 | 0 0 |

*= Two (2) adverse events were associated with post-study laboratory test results and have been assigned to each period.

Conclusions

The pharmacokinetic parameters were well defined for the three doses (100 µg, 400 µg and 800 µg) administered in this study. $C_{max}$ and $AUC_\infty$ seem to be proportional, $AUC_T$ is consistent with dose-proportionality between the 400 µg and 800 µg. Furthermore, the two formulations of fentanyl (1 mg/ml and 4 mg/ml sublingual spray in doses of 100 µg, 400 µg and 800 µg) administered during the study were well tolerated in most of the subjects. No subject participating in the trial reported serious adverse events during the course of this study.

Examples 8-12

In-Vitro Permeation Experiments

The permeation characteristics of fentanyl formulations were studied using EpiOral tissues (ORL-100). MatTek Corp's EpiOral is used as model for screening sublingual drug absorption of pharmaceutical formulations. MatTek's EpiOral tissue consists of normal, human-derived epithelial cells. The cells have been cultured to form multilayered, highly differentiated models of the human buccal (EpiOral) phenotypes. The EpiOral tissue model exhibits in vivo-like morphological and growth characteristics which are uniform and highly reproducible. Morphologically, the tissue model closely parallels native human tissue, thus providing a useful in-vitro means to assess in-vivo permeability of pharmaceutical formulations across sublingual mucosa.

The EpiOral tissues, grown on cell culture inserts with Teflon® (Teflon is a registered trademark of E.I. Du Pont De Nemours and Company) backing membrane, were shipped by MatTek Corp on Monday for delivery on Tuesday morning. All the tissues were used in the permeability experiments within 72 hours of shipment. The inserts containing the tissues were rinsed with distilled water before the start of permeation experiments. The tissue area for the ORL-100 is 0.6 cm2.

The receiver compartment (wells) received 0.3 ml of phosphate citrate buffer of pH 6.6 (receiver solution). The donor compartments (tissue inserts) were placed in the wells and filled with 0.5 ml of drug solution (donor solution).

The inserts were moved from well to well containing fresh receiver fluid at predetermined intervals (2, 5, 7, 9, 11, 13, 15, 30, 45, 60, 90, and 120 min). After permeation studies both donor and receiver fluids were collected in vials for analysis by HPLC. The receiver and donor solution concentrations and the flux over each permeation time interval were determined.

Example 8

In Example 8, the permeation of fentanyl base was compared to the permeation of fentanyl citrate. The formulations and percent permeated in 2 hours is listed in the table below:

TABLE 20

| EXAMPLE # * | | CONC. OF FENTANYL BASE | ALCOHOL % (V) | PG % (V) | MIGLYOL ® % (V) | % PERMEATED IN 2 HOURS |
|---|---|---|---|---|---|---|
| Fentanyl Base | 8-a(b) | 1 mg/ml | 20 | 5 | — | 17.33 |
| Fentanyl Base | 8-b(w) | 1 mg/ml | 20 | 5 | — | 17.18 |
| Fentanyl Citrate | 8-c(b) | 0.646 mg/ml | 20 | 5 | — | 1.81 |
| Fentanyl Base | 8-d | 1 mg/ml | 20 | 5 | 79.3 | 1.64 |

(b)—buffer,
(w)—water

Example 9

In Example 9, Effect of Alcohol on the Permeation of Fentanyl Base Formulations was tested. The formulations and percent permeated in 2 hours are listed in the Table below:

TABLE 21

| EXAMPLE #* | CONC. OF FENTANYL BASE | ALCOHOL % (V) | PG % (V) | % PERMEATED IN 2 HOURS |
|---|---|---|---|---|
| 9-a (w) (Control) | 1 mg/ml | 20 | 5 | 17.18 |
| 9-b (w) | 1 mg/ml | 28 | 5 | 13.45 |
| 9-c (w) | 1 mg/ml | 40 | 5 | 10.95 |
| 9-c (w) | 1 mg/ml | 50 | 5 | 9.18 |

(b)—buffer,
(w)—water

Example 10

In Example 10, the effects of PG (propylene glycol) on Fentanyl Formulations was tested. The formulations and percent permeated in 2 hours are listed in the table below:

TABLE 22

| EXAMPLE #* | CONC. OF FENTANYL BASE | ALCOHOL % (V) | PG % (V) | % PERMEATED IN 2 HOURS |
|---|---|---|---|---|
| 10-a (w) (Control) | 1 mg/ml | 20 | 5 | 17.18 |
| 10-b (w) | 1 mg/ml | 20 | 25 | 14.518 |

(b)—buffer,
(w)—water

Example 11

In Example 11, the effect of pH on Fentanyl Formulations was tested. The formulations and percent permeated in 2 hours are listed in the table below. As indicated in the table, the permeation of fentanyl across buccal tissue was dependent on the pH of the formulation. Because fentanyl has pKa value (7.3 and 8.4) within the pH range studied, its degree of ionization changed as the pH of the formulation was altered. The results in the table below indicate that that formulations adjusted to pH between 8 and 9 were showing better permeability and physical stability.

TABLE 23

| EXAMPLE #* | CONC. OF FENTANYL BASE | BUFFER PH | ALCOHOL % (V) | PG % (V) | % PERMEATED IN 2 HOURS |
|---|---|---|---|---|---|
| 11-a (w) (Control) | 2 mg/ml | Water | 30 | 5 | 17.83 |
| 11-b (b) | 2 mg/ml | 5.5 | 30 | 4 | 5.33 |
| 11-c (b) | 2 mg/ml | 6.6 | 29 | 4 | 10.62 |
| 11-d (b) | 2 mg/ml | 8.6 | 29 | 4 | 13.48 |
| 11-e (b) | 2 mg/ml | 9.6 | 29 | 4 | 11.8 |

(b)—buffer,
(w)—water

Example 12

In Example 12, several ingredients including hydroxypropyl beta cyclodextrin (HPBCD), mannitol, polyvinyl pyrrolidone (PVP), propylene carbonate (PC), sodium glycocholate (SG), sodium lauryl sulphate (SLS), triacetin, triethyl citrate and Tween® 80 (Tween is a registered trademark of Uniqema Americas LLC; TW 80) were added to the formulations either individually or in combination and studied for their effect on permeability and solution stability. Table 24 to 36 summarizes the formulations and permeation results of buffered and water formulations containing the above excipients.

TABLE 24

Results of the effects of Buffer and Water on Fentanyl Formulations.

| EXAMPLE #* | CONC. OF FENTANYL BASE | BUFFER OR WATER | ALCOHOL % (V) | PG % (V) | INACTIVE INGREDIENTS | | | % PERMEATED IN 2 HOUR |
| | | | | | Mannitol % (wt) | Triacetin % (wt) | TW80 % (wt) | |
|---|---|---|---|---|---|---|---|---|
| 12-a(b) (Control) | 1 mg/ml | B | 20 | 5 | — | — | — | 17.33 |
| 12-b(w) (Control) | 1 mg/ml | W | 20 | 5 | — | — | — | 17.18 |
| 12-c(b) | 1 mg/ml | B | 20 | 5 | 0.1 | 0.15 | — | 16.14 |
| 12-d(w) | 1 mg/ml | W | 20 | 5 | 0.1 | 0.15 | — | 12.10 |

TABLE 24-continued

Results of the effects of Buffer and Water on Fentanyl Formulations.

| EXAMPLE #* | CONC. OF FENTANYL BASE | BUFFER OR WATER | ALCOHOL % (V) | PG % (V) | Mannitol % (wt) | Triacetin % (wt) | TW80 % (wt) | % PERMEATED IN 2 HOUR |
|---|---|---|---|---|---|---|---|---|
| 12-e(b) | 1 mg/ml | B | 20 | 5 | 0.3 | — | 0.2 | 16.02 |
| 12-f(w) | 1 mg/ml | W | 20 | 5 | 0.3 | — | 0.2 | 12.35 |
| 12-g(b) | 1 mg/ml | B | 20 | 5 | 0.15 | 0.3 | 0.1 | 16.43 |
| 12-h(w) | 1 mg/ml | W | 20 | 5 | 0.15 | 0.3 | 0.1 | 9.76 |
| 12-i(b) | 1 mg/ml | B | 20 | 5 | 0.2 | — | 0.2 | 18.74 |
| 12-j(w) |  | W | 20 | 5 | 0.2 | — | 0.2 | 13.19 |
| 12-k(b) | 1 mg/ml | B | 20 | 5 | — | — | 0.3 | 14.73 |
| 12-l(w) | 1 mg/ml | W | 20 | 5 | — | — | 0.3 | 13.76 |

(b)—buffer,
(w)—water

The results in Table 24 indicate that all the buffered formulations had similar permeability characteristics as that of control formulations except the buffered formulation containing 0.3% Tween® 80 which showed lower permeability. All water formulations exhibited lower permeability than buffered formulations.

TABLE 25

Effect of HPBCD on Fentanyl Formulations

| EXAMPLE #* | CONC. OF FENTANYL BASE | ALCOHOL % (V) | PG % (V) | HPBCD (MOLECULAR RATIO TO API) | % PERMEATED IN 2 HOURS |
|---|---|---|---|---|---|
| 12-m (w) (Control) | 1 mg/ml | 20 | 5 | — | 17.18 |
| 12-n (w) | 1 mg/ml | 20 | 5 | 1:1 (0.413%) | 14.28 |
| 12-o (w) | 1 mg/ml | 20 | 5 | 1:2 (0.826%) | 13.50 |

(b)—buffer,
(w)—water

TABLE 26

Effect of Mannitol on Fentanyl Formulations

| EXAMPLE #* | CONC. OF FENTANYL BASE | ALCOHOL % (V) | PG % (V) | MANNITOL % (WT) | % PERMEATED IN 2 HOURS |
|---|---|---|---|---|---|
| 12-p (b) (Control) | 1 mg/ml | 20 | 5 | — | 17.33 |
| 12-q (b) | 1 mg/ml | 20 | 5 | 0.3 | 17.71 |
| 12-r (b) | 1 mg/ml | 20 | 5 | 0.4 | 16.86 |
| 12-s (b) | 1 mg/ml | 20 | 5 | 0.5 | 15.41 |
| 12-t (b) | 1 mg/ml | 20 | 5 | 0.8 | 14.81 |

(b)—buffer,
(w)—water

TABLE 27

Effect of Polyvinyl Pyrrolidone (PVP) on Fentanyl Formulations

| EXAMPLE #* | CONC. OF FENTANYL BASE | ALCOHOL % (V) | PG % (V) | PVP % (WT) | % PERMEATED IN 2 HOURS |
|---|---|---|---|---|---|
| 12-u (w) (Control) | 1 mg/ml | 20 | 5 | — | 17.18 |
| 12-v (w) | 1 mg/ml | 20 | 5 | 0.1 | 16.73 |
| 12-w (w) | 1 mg/ml | 20 | 5 | 0.5 | 14.68 |
| 12-x (w) | 1 mg/ml | 20 | 5 | 1 | 14.52 |
| 12-y (w) | 1 mg/ml | 25 | 5 | 3 | 10.75 |

(b)—buffer,
(w)—water

TABLE 28

Effect of Propylene Carbonate (PC) on Fentanyl Formulations

| EXAMPLE #* | CONC. OF FENTANYL BASE | ALCOHOL % (V) | PG % (V) | PC % (WT) | % PERMEATED IN 2 HOURS |
|---|---|---|---|---|---|
| 12-z (w) (Control) | 1 mg/ml | 20 | 5 | — | 17.18 |
| 12-aa (w) | 1 mg/ml | 20 | 5 | 1 | 14.39 |
| 12-bb (w) | 1 mg/ml | 20 | 5 | 1.5 | 14.43 |

(b)—buffer,
(w)—water

TABLE 29

Effect of Sodium Glycocholate (SG) on Fentanyl Formulations

| EXAMPLE #* | CONC. OF FENTANYL BASE | ALCOHOL % (V) | PG % (V) | SG % (WT) | % PERMEATED IN 2 HOURS |
|---|---|---|---|---|---|
| 12-cc (w) (Control) | 1 mg/ml | 20 | 5 | — | 17.18 |
| 12-dd (w) | 1 mg/ml | 20 | 5 | 0.5 | 18.30 |
| 12-ee (w) | 1 mg/ml | 20 | 5 | 1 | 19.78 |

(b)—buffer,
(w)—water

TABLE 30

Effect of Triacetin on Fentanyl Formulations

| EXAMPLE #* | CONC. OF FENTANYL BASE | ALCOHOL % (V) | PG % (V) | TRIACETIN % (WT) | % PERMEATED IN 2 HOURS |
|---|---|---|---|---|---|
| 12-ff (b) (Control) | 1 mg/ml | 20 | 5 | — | 17.33 |
| 12-gg (b) | 1 mg/ml | 20 | 5 | 0.5 | 17.71 |
| 12-hh (b) | 1 mg/ml | 20 | 5 | 2 | 14.56 |

(b)—buffer,
(w)—water

TABLE 31

Effect of Triethyl Citrate on Fentanyl Formulations

| EXAMPLE #* | CONC. OF FENTANYL BASE | ALCOHOL % (V) | PG % (V) | TRIETHYL CITRATE % (WT) | % PERMEATED IN 2 HOURS |
|---|---|---|---|---|---|
| 12-ii (w) (Control) | 1 mg/ml | 20 | 5 | — | 17.18 |
| 12-jj (b) | 1 mg/ml | 20 | 5 | 0.5 | 15.81 |
| 12-kk (b) | 1 mg/ml | 20 | 5 | 2 | 10.02 |

(b)—buffer,
(w)—water

TABLE 32

Effect of Tween 80 (TW 80) on Fentanyl Formulations

| EXAMPLE #* | CONC. OF FENTANYL BASE | ALCOHOL % (V) | PG % (V) | TW80 % (WT) | % PERMEATED IN 2 HOURS |
|---|---|---|---|---|---|
| 12-ll(b) (Control) | 1 mg/ml | 20 | 5 | — | 17.33 |
| 12-mm(b) | 1 mg/ml | 20 | 5 | 0.3 | 14.73 |
| 12-nn(b) | 1 mg/ml | 20 | 5 | 0.6 | 13.72 |

(b)—buffer,
(w)—water

TABLE 33

Effect of Labrasol & SLS on Fentanyl Formulations

| EXAMPLE #* | CONC. OF FENTANYL BASE | ALCOHOL % (V) | PG % (V) | LABRASOL % (WT) | SLS % (WT) | % PERMEATED IN 2 HOURS |
|---|---|---|---|---|---|---|
| 12-oo(w) (Control) | 1 mg/ml | 20 | 5 | — | — | 17.18 |
| 12-pp(w) | 1 mg/ml | 20 | 5 | 6.5 | — | 8.25 |
| 12-qq(w) | 1 mg/ml | 20 | 5 | 3.0 | 0.5 | 9.31 |
| 12-rr(w) | 1 mg/ml | 20 | 5 | 6.5 | 0.5 | 8.63 |

(b)—buffer,
(w)—water

TABLE 34

Effect of Mannitol & Triacetin on Fentanyl Formulations

| EXAMPLE #* | CONC. OF FENTANYL BASE | ALCOHOL % (V) | PG % (V) | MANNITOL % (WT) | TRIACETIN % (WT) | % PERMEATED IN 2 HOURS |
|---|---|---|---|---|---|---|
| 12-ss(b) (Control) | 1 mg/ml | 20 | 5 | — | — | 17.33 |
| 12-tt(b) | 1 mg/ml | 20 | 5 | 0.1 | 0.15 | 16.14 |
| 12-uu(b) | 1 mg/ml | 20 | 5 | 0.15 | 0.4 | 18.33 |
| 12-vv(b) | 1 mg/ml | 20 | 5 | 0.15 | 0.5 | 17.14 |
| 12-ww(b) | 1 mg/ml | 20 | 5 | 0.2 | 0.3 | 16.73 |
| 12-xx(b) | 1 mg/ml | 20 | 5 | 0.25 | 0.5 | 16.31 |
| 12-yy(b) | 1 mg/ml | 20 | 5 | 0.3 | 0.2 | 17.70 |
| 12-zz(b) | 1 mg/ml | 20 | 5 | 0.4 | 0.2 | 16.88 |

(b)—buffer,
(w)—water

TABLE 35

Effect of Mannitol & TW 80 on Fentanyl Formulations

| EXAMPLE #* | CONC. OF FENTANYL BASE | ALCOHOL % (V) | PG % (V) | MANNITOL % (WT) | TW80 % (WT) | % PERMEATED IN 2 HOURS |
|---|---|---|---|---|---|---|
| 12-aaa(b) (Control) | 1 mg/ml | 20 | 5 | — | — | 17.33 |
| 12-bbb(b) | 1 mg/ml | 20 | 5 | 0.2 | 0.2 | 18.74 |
| 12-ccc(b) | 1 mg/ml | 20 | 5 | 0.3 | 0.1 | 16.53 |
| 12-ddd(b) | 1 mg/ml | 20 | 5 | 0.3 | 0.2 | 16.02 |

(b)—buffer,
(w)—water

TABLE 36

Effect of Triacetin & TW 80 on Fentanyl Formulations

| EXAMPLE #* | CONC. OF FENTANYL BASE | ALCOHOL % (V) | PG % (V) | TW 80 % (WT) | TRIACETIN % (WT) | % PERMEATED IN 2 HOURS |
|---|---|---|---|---|---|---|
| 12-eee(b) (Control) | 1 mg/ml | 20 | 5 | — | — | 17.33 |
| 12-fff(b) | 1 mg/ml | 20 | 5 | 0.1 | 0.2 | 16.99 |
| 12-ggg(b) | 1 mg/ml | 20 | 5 | 0.1 | 0.3 | 16.63 |

(b)—buffer,
(w)—water

The results indicate that addition of individual excipients including HPBCD (Table 25), PVP (Table 27), PC (Table 28), Triethyl citrate (Table 31) and Tween® 80 (Table 32) to the formulation decreased the permeability of fentanyl across MatTek buccal membranes irrespective of excipient concentration. As shown in Table 26 and Table 30, formulations containing 0.3% Mannitol and 0.5% Triacetin showed similar permeability characterisitics as that of control formulation but the permeability decreased as the concentrations of these individual excipients were increased in the formulations. Stability studies indicated that a minimum of 0.45% and 0.5% mannitol concentration should be added to buffer and water formulations, respectively, to keep them stable. In case of Triacetin, formulations containing 0.5% or higher concentrations of triacetin were found to be stable.

Permeation of fentanyl from formulations containing SG was greater than that of control formulations (Table 29). Also, we observed that fentanyl permeation increased with the increase of SG concentration in the formulation.

The results of fentanyl permeation across MatTek-buccal tissues from formulations containing combination of excipients are shown in Tables 33-36. Addition of Labrasol® (Labrasol is a registered trademark of Gattefosse SAS) to the formulation improved the stability but decreased fentanyl permeation across MatTek buccal tissues. Similar results were observed with formulations containing Labrasol® and SLS. Among all the formulations containing combination of excipients, two formulations, Example 12-uu (0.15% mannitol, 0.4% triacetin) and Example 12-bbb (0.2% mannitol, 0.2% TW80), showed higher permeability compared to control formulation. We observed that the presence of mannitol in triacetin formulations did not show any improvement in the permeation. Hence, the formulation containing 0.5% triacetin (Table 30) was selected for further studies. Though the formulation, Example 12-bbb, showed good permeability mannitol concentration was increased to 0.3% to improve the stability of the product.

Both fentanyl citrate and fentanyl base formulations were stable at all temperatures studied. The data from in-vitro tissue permeation studies, as shown in Table 3, showed that permeation of fentanyl from fentanyl base formulations was about 10-fold higher than from fentanyl citrate formulations. Water and buffer formulations did not show any significant difference in fentanyl base permeation across buccal tissue. Our studies also showed that fentanyl base formulation containing Miglyol® had very low permeability. Among the excipients, triacetin at 0.5% and mannitol at 0.3% in combination with 0.2% TW 80 showed good permeability and stability.

The transport of fentanyl across buccal tissues was dependent on ethyl alcohol (ethanol) and propylene glycol (PG) concentrations in the formulation. Ethanol is used as a cosolvent to solubilize fentanyl base in aqueous based formulations. In this investigation, we observed that formulations (with 1 mg/ml of fentanyl base) containing less than 20% of ethanol were precipitating at refrigerated conditions. Also, we observed that permeation of fentanyl across buccal tissue was indirectly proportional to ethanol concentrations in the formulations (Table 21). Similar results were observed with PG (Table 22). PG was helpful in increasing the solubility of fentanyl base in aqueous solution and also in enhancing the permeation of the fentanyl base across buccal tissues. Formulations containing more than 5% PG did not show significant improvement in the permeation of fentanyl, however, the solution viscosities increased proportionally with PG concentrations. The formulations containing more than 5% PG did not show good spray characteristics.

Example 13

In Example 13, a formulation having the following ingredients in Table 37 was tested. The formulation did not include fentanyl.

TABLE 37

| Ingredient | |
|---|---|
| Dehydrated Alcohol % (v/v) | 30% |
| Propylene glycol % (v/v) | 5% |
| Peppermint Oil % (v/v) | 0.2% |
| Borate buffer (pH 9) | QS |
| Hydroxy Propyl Beta Cyclodextrin (HPBCD) | 1:2 |

The formulation was sprayed using a 0.10 ml multidose nasal spray pump by Pfeiffer® of America, Princeton, N.J. (Pfeiffer is a registered trademark of Ing. Erich Pfeiffer GmbH) and the droplets were measured using a Malvern® Mastersizer® S device, by Malvern® Instruments Ltd. A single depression of the sublingual spray pump generated a plume which was then analyzed for spray particles. The sample size for the dose volume, spray pattern, and droplet size distribution was 25 sprays.

Droplet Volume

In the droplet volume evaluation, 25 spray samples were evaluated using 5 different stroke numbers for each spray sample the following results were measured:
Overall mean=100.4 μl
Maximum single actual value=103.2 μl
Lowest single actual value=95.3 μl
Standard deviation=1.1
Range=7.9
Coefficient of variation=1.1%

Spray Pattern

In the spray pattern evaluation, 25 spray samples were evaluated using a manual actuation at 30 mm from the target. The formulation was dyed with methylene blue and the following spray pattern results were measured:
Small diameter [mm]
min: 35.4
mean: 50.6
max: 62
s: 7.00
largest diameter [mm]
min: 40
mean: 56.9
max: 67
s: 6.01
spray angle
min: 64°
mean: 83.3°
max: 94°
s: 7.03
ratio (largest/smallest diameter)
min: 1.04
mean: 1.13
max: 1.33
s: 0.073

Droplet Size Distribution

In the droplet size distribution evaluation, 25 spray samples were evaluated using a manual actuation at 30 mm from the target. The following droplet size distribution results were measured:
Percentage share of droplet diameters at 10 μm [%]
min: 0.65
mean: 1.66
max: 2.70
s: 0.527
10% of the droplet diameters are smaller than the indicated value [μm]
min: 15
mean: 18.2
max: 23
s: 1.91
50% of the droplet diameters are smaller than the indicated value [μm]
min: 35
mean: 44.7
max: 65
s: 7.52
90% of the droplet diameters are smaller than the indicated value [μm]
min: 96
mean: 154.4
max: 349
s: 64.42

Example 14

In Example 14, a formulation having the following ingredients in Table 38 was tested. The formulation did not include fentanyl.

TABLE 38

| Ingredient | |
| --- | --- |
| Dehydrated Alcohol % (v/v) | 30% |
| Propylene glycol % (v/v) | 5% |
| Peppermint Oil % (v/v) | 0.2% |
| Borate buffer (pH 9) | QS |
| Hydroxy Propyl Beta Cyclodextrin (HPBCD) | 1:2 |
| Hydroxy Propyl Cellulose (HPC EP) % (v/v) | 1% |

The formulation was sprayed using a 0.10 ml multidose nasal spray pump by Pfeiffer® of America, Princeton, N.J. and the droplets were measured using a Malvern® Mastersizer® S device, by Malvern® Instruments Ltd. A single depression of the sublingual spray pump generated a plume which was then analyzed for spray particles. The sample size for the dose volume, spray pattern, and droplet size distribution was 25 sprays.

Droplet Volume

In the droplet volume evaluation, 25 spray samples were evaluated using 5 different stroke numbers the following results were measured:
Overall mean value=101.5 µl
Maximum single actual value=103.7 µl
Lowest single actual value=96.1 µl
Standard deviation=1.3
Range=7.6
Coefficient of variation=1.2%

Spray Pattern

In the spray pattern evaluation, 25 spray samples were evaluated using a manual actuation at 30 mm from the target. The formulation was dyed with methylene blue and the following spray pattern results were measured:
Small diameter [mm]
min: 29
mean: 34.0
max: 46
s: 3.47
largest diameter
min: 35
mean: 40.8
max: 55
s: 4.13
spray angle
min: 58°
mean: 63.8°
max: 80°
s: 4.65
ratio (largest/smallest diameter)
min: 1.08
mean: 1.20
max: 1.50
s: 0.092

Droplet Size Distribution

In the droplet size distribution evaluation, 25 spray samples were evaluated using a manual actuation at 30 mm from the target. The following droplet size results were measured:
Percentage share of droplet diameters at 10 µm [%]
min: 0.24
mean: 0.68
max: 1.28
s: 0.278
10% of the droplet diameters are smaller than the indicated value [µm]
min: 22
mean: 26.7
max: 35
s: 2.95
50% of the droplet diameters are smaller than the indicated value [µm]
min: 61
mean: 83.3
max: 114
s: 11.41
90% of the droplet diameters are smaller than the indicated value [µm]
min: 192
mean: 294.6
max: 440
s: 53.32

Example 15

In Example 15, an assay procedure for fentanyl in 1, 2, 4, 6, and 8 mg/mL fentanyl sublingual spray samples with a working concentration of between 0.1 µg/mL and 5 µg/mL fentanyl in solution was performed. This method was developed and qualified in compliance with GMP requirements. The method was determined to be linear over the range of 0.05 µg/mL to 7.83 µg/mL fentanyl. The fentanyl working standard solution was stable over a seven day period in volumetric glassware and amber HPLC vials at refrigerated and ambient conditions.

The equipment and supplies utilized in this process included an HPLC system equipped with a pump, variable wavelength detector, and autosampler, or equivalent, a Waters Symmetry HPLC column (C18, 4.6×75 mm, 3.5 µm particle size), 0.45 µm, 47 mm nylon filters (Gelman Nylaflo® P/N 66608 or equivalent; Nylaflo is a registered trademark of Membrana Inc.), acetonitrile (HPLC Grade), potassium phosphate monobasic (ACS Grade), phosphoric acid (ACS Grade), deionized water, alcohol (ethanol, absolute), and fentanyl base reference standard.

The solution preparations were prepared as described below and may be scaled as required.

For each liter of phosphate buffer solution (50 mM $KH_2PO_4$ pH 2.8), 6.8 g of potassium phosphate mono basic and 1 liter of water was combined in a suitable vessel and mixed well. The pH of the solution was adjusted to 2.8 with the drop-wise addition of phosphoric acid. The solution was filtered through 0.45 µm nylon. This solution expires after one month.

For each liter of mobile phase (25% ACN, 75% phosphate buffer) solution, 750 mL of phosphate buffer solution was combined with 250 mL of acetonitrile in a suitable vessel and mixed well. The system is degassed by an appropriate method before use if required. This solution expires after one month.

For each liter of stock diluent (95/5, Ethanol/Acetonitrile) solution, 950 mL ethanol and 50 mL acetonitrile was combined in a suitable container and mixed well. This solution expires after one month.

Stock standard I, 40 mg/mL, ("SSI"), was prepared by weighing approximately 10.0 mg of fentanyl reference standard and added to a 250 mL volumetric flask. Approximately 200 mL stock diluent was added and swirled to dissolve the solid material. The mixture was diluted to the desired volume with stock diluent and mixed well.

Stock standard II, 40 µg/mL, ("SSII"), was prepared by weighing approximately 10.0 mg of fentanyl reference standard and add to a 250 mL volumetric flask. Approximately 200 mL of stock diluent was added and swirled to dissolve solid material. The mixture was diluted to the desired volume with stock diluent and mixed well.

Working standard I, 2.4 μg/mL, ("WSI"), was prepared by transferring 3.0 mL of stock standard I to a 50 mL volumetric flask. The mixture was diluted to the desired volume with mobile phase solution and mixed well. This solution expires after seven days.

Working standard II, 2.4 μg/mL, ("WSII") was prepared by transferring 3.0 mL of stock standard II to a 50 mL volumetric flask. The mixture was diluted to the desired volume with mobile phase solution and mixed well. This solution expires after seven days.

The chromatographic conditions for the HPLC procedure are set forth below:
Column: HPLC Column Waters Symmetry C18, 4.6×75 mm, 3.5 μm particle size
UV Detection: 214 nm
Flow Rate: 2.0 mL/minute
Injection Volume: 50 μL
Temperature: Ambient (The temperature may be controlled at 25° C.).
Acquisition Time: 13 minutes
HPLC Procedure After the system suitability is established, a maximum of 12 sample solutions can be injected in between working standards. A typical sequence would be as follows:
2× Mobile Phase (Blank)
2× Working standard II
5× Working standard I
1× Sample (up to 12 injections)
1× Working standard I
1× Sample (up to 12 injections)
1× Working standard I
System Suitability There should be no significant interfering peaks present at the retention time of fentanyl in the mobile phase blank injections. In terms of injection precision, the RSD of fentanyl for five replicate injections of working standard I should not exceed 2.0%. In terms of standard agreement, the agreement between the average peak response for the first five working standard I injections and the two working standard II injections should be between 98 to 102%. The agreement between working standards I and II need only be demonstrated once during the expiry of standards. The tailing factor at 5% peak height for fentanyl in the first working standard I injection should be between 0.8 and 1.5. In terms of standard precision over the run, the RSD of peak area for fentanyl in the working standard I injections over the run (OTR) should not exceed 2.0%.

Calculations are performed as set forth below.
Working standard concentration is calculated as follows:

$$\frac{\text{Mass of standard (mg)}}{250.0 \text{ mL}} * \frac{1000 \text{ μg}}{1 \text{ mg}} * \frac{3.0 \text{ mL}}{50.0 \text{ mL}} * \text{Purity of Standard} =$$

μg/mL Fentanyl

Response Factor ($R_f$) is calculated as follows:

$$\frac{\text{Fentanyl Peak Area}}{\text{Fentanyl Concentration (μg/mL)}} *= R_f$$

Standard Agreement is calculated as follows:

$$\frac{\text{Average } R_f WSII}{\text{Average } R_f WSI} * 100 = \% \text{ Standard Agreement}$$

Example 16

In Example 16 the method for determination of droplet size distribution by laser diffraction for fentanyl sublingual spray using the Spraytec device by Malvern® was performed.

All data generated and described within this report were reviewed for compliance with Good Manufacturing Practices (21 CFR Parts 210 and 211).

The purpose of this project was to develop and validate a droplet size distribution method by laser diffraction for use with fentanyl sublingual spray product and placebo. The first portion of the project performed product evaluations to determine the proper automated actuation parameters to be used with the MightyRunt Actuation Station by Innova Systems, Inc. Using the automated actuation station, development of the droplet size distribution method for the sublingual product included vignetting studies, exhaust placement studies, and device placement studies.

The method validation evaluated intermediate precision between two analysts performing the developed method. All method development and qualification activities were performed using placebo.

Samples were prepared using Pfeiffer® unit dose glass vials, Pfeiffer® unit dose VI stoppers, Pfeiffer® vial holder, and Pfeiffer® unit dose applicator. The instrumentation utilized in the study include a Spraytec with 200 mm lens by Malvern® Instruments, Inc, a MightyRunt Actuation Station by Innova Systems Inc. equipped with an exhaust fan attachment, and a Mettler Toledo® balance Model AT201.

Actuation Parameter Study

Using the Spraytec to track the plume duration and droplet size distribution, the actuation parameters for the MightyRunt Actuation Station (MightyRunt) were optimized to replicate the plume duration, droplet size distribution, and shot weight generated by manual actuation. Dv10 (10% of the droplet diameters are smaller that the indicated value), Dv50 (50% of the droplet diameters are smaller that the indicated value), and Dv90, (90% of the droplet diameters are smaller that the indicated value), results from six devices with manual actuations were compared with the results from the six devices with automated actuations.

Acceptance Criteria

The individual shot weight results for the automated actuations should all fall within the range of 75%-125% of the average shot weight for the manual actuations. The average Dv10, Dv50 and Dv90 results of the automated actuations should be within 75% to 125% of the average Dv10, Dv50 and Dv90 results for the manual actuations.

Statistical analysis shall include performance of a students' t-test on the two sets of droplet size distribution results. The results of the students' t-test should indicate that the manual versus automated sets of data is statistically equivalent.

Method Development

Method development involved a vignetting study and exhaust study utilizing the Spraytec. Actuations were performed using the MightyRunt and previously determined parameters. Vignetting occurs during laser diffraction analysis when the small droplets of a spray plume scatter the laser at an angle too steep to be captured by the range lens. Placement of the device close enough to the range lens to capture all of the scattered light without deposition on the range lens is critical. The vignetting study determined the appropriate range lens for analysis and the appropriate distance from device to range lens.

Exhaust placement affects plume travel. Plume velocity should not be accelerated by the draw of the exhaust and large droplets should not fall while traveling through the laser path. The exhaust study determined the appropriate position behind the plume of the spray to ensure proper plume capture after passing through the laser path. The method included two distances for analysis from the tip of the nozzle to the path of the laser for a more complete characterization of the droplet size distribution.

Method Validation

Validation consisted of determining the precision and ruggedness of the method. A total of 24 devices from a single lot of placebo were used in the validation. One analyst tested 6 actuations at each distance. To demonstrate ruggedness, a second analyst repeated the analyses. Dv10, Dv50, and Dv90 results were compared.

Acceptance Criteria

The individual shot weight results for analyst one should all fall within the range of 75%-125% of the average shot weight for analyst two. The average Dv10, Dv50 and Dv90 results for analyst one should be within 75% to 125% of the average Dv10, Dv50 and Dv90 results for analyst two.

The final experimental procedure is set forth below.

Prior to analysis, the background and scattering profiles were verified as appropriate for analysis.

The sample bottle is inserted into the nozzle holder. Coasters were used to raise the platform for minimal adjustment. The coaster attached to the device holder was placed on top of coasters used for adjustment.

The MightyRunt with bottle and exhaust fan was placed in the appropriate positions for analysis. The MightyRunt was raised with the nozzle centered in front of the laser path with a lab jack. It was ensured that the MightyRunt was level following adjustment. Two bottle-to-laser distances were be evaluated, 7 cm and 4 cm, measured from the pump tip to the center of the laser path. For all analyses, the bottle was placed 14 cm from the range lens support structure to the pump tip.

The exhaust fan was turned on and placed on a lab jack 3 cm behind the laser path, centered behind the device, measured from the center of the laser path to the front edge of the exhaust shield. The exhaust fan had an impaction surface for the droplets to adhere to, i.e. a cheesecloth placed in the path of the droplets. ⅛ sheet of 18×36 inch cheesecloth folded into approximately a 4.5-inch square (4 layers of cheesecloth) is a sufficient impaction surface and will not impede the flow of the fan.

The device was actuated using the MightyRunt station and droplet size distribution was collected for each individual shot at the appropriate distances for analysis.

A report was printed for the entire plume duration and the plume plateau.

Data Reporting

The data for the D10, D50, D90, and Span values for each actuation are reported. The average and precision (% RSD) (percent relative standard deviation) were calculated for the D10, D50, and D90. Note: Span is defined as (D90-D10)/D50. Individual droplet size distribution results (μm) and span values (unitless) were reported to X.XX. All average droplet size distribution results should be reported to X.X μm. All RSD values should be reported to X.X %.

Statistical analysis included performance of a students' t-test on the two sets of droplet size distribution results. The results of the students' t-test should have indicated that the analysts sets of data is statistically equivalent.

Results and Discussion

All spray plumes have three stages. The first stage, development, was characterized by variable droplets and decreasing transmission of the laser. The second stage, stable, was characterized by a stable droplet distribution and transmission. Variable droplets and increasing transmission characterize the final stage, dissipation. All comparisons of droplet size distribution used the stable stage of the plume.

Actuation Parameter Study

During the optimization of the actuation parameters for the MightyRunt, the plumes from manual and automated actuations were measured using the Spraytec. Dv10, Dv50, and Dv90 results were compared to optimize the automated parameters. The type of device that was examined in this study was significantly different from typical nasal sprays. Rather than a spring requiring a consistent force to initiate actuation and deliver the drug, there was an amount of force that was required to break the tabs or actuate the device. This force was not the same amount of force required to deliver the drug from the device once the tabs are broken. Because this device did not contain a spring, the parameters of interest were actuation force, force rise time, and minimum travel distance. The finalized MightyRunt parameters are listed below in Table 39 and the utilized Spraytec settings are listed below in Table 40.

TABLE 39

Mighty Runt Actuation Parameters

| Parameter | Setting |
|---|---|
| Actuation Force | 4.0 kg |
| Force Rise Time | 0.2 sec |
| Hold Time | 1.0 sec |
| Force Fall Time | 1.0 sec |
| Spray Delay | 1 sec |
| Minimum Travel Distance | 10 mm |
| Maximum travel Time | 4.0 sec |
| Trigger Signal Delay | 0.0 sec |
| Stage | Yes |

TABLE 40

Spraytec Settings

| Option | Setting |
|---|---|
| Test Duration | 200 msec |
| Data Acquisition Rate | 1000 Hz |
| Acquisition Duty Cycle | 0% |
| Experimental Trigger | Transmission |
| Transmission Trigger | 98% |
| Range Lens | 200 mm |

The comparison of manual and automated actuations was performed using six devices with manual actuations and six devices with automated actuations. The droplet size distribution and shot weight results are summarized in Table 41 below.

TABLE 41

| Device | D10 (μm) | D50 (μm) | D90 (μm) | Shot Weight (mg) | % Average |
|---|---|---|---|---|---|
| Manual 1 | 19.0 | 44.5 | 76.8 | 89.1 | |
| Manual 2 | 18.1 | 42.7 | 84.9 | 86.9 | |
| Manual 3 | 33.3 | 58.7 | 108.4 | 90.4 | |
| Manual 4 | 20.8 | 44.6 | 81.2 | 87.0 | |
| Manual 5 | 18.3 | 42.7 | 80.7 | 87.8 | |
| Manual 6 | 19.0 | 44.3 | 81.5 | 84.9 | |
| Average | 21.4 | 46.3 | 85.6 | 87.7 | |
| % RSD | 27.5 | 13.3 | 13.4 | 2.2 | |
| Mighty Runt 1 | 17.3 | 37.5 | 65.1 | 83.8 | 96 |
| Mighty Runt 2 | 16.1 | 35.3 | 64.0 | 66.0 | 75 |
| Mighty Runt 3 | 18.8 | 38.9 | 66.2 | 84.2 | 96 |
| Mighty Runt 4 | 15.4 | 37.8 | 77.6 | 85.4 | 97 |
| Mighty Runt 5 | 17.6 | 38.6 | 67.1 | 82.4 | 94 |
| Mighty Runt 6 | 19.4 | 41.9 | 74.8 | 88.0 | 100 |
| Average | 17.4 | 38.3 | 69.1 | 81.6 | |
| % RSD | 8.8 | 5.6 | 8.2 | 9.7 | |
| Overall average | 19.43 | 42.30 | 77.36 | 84.7 | |
| Overall % RSD | 23.7 | 14.3 | 15.7 | 7.5 | |
| Automated Actuation Average as % of Manual Actuation Average | 81 | 83 | 81 | | |
| t-stat | 1.60 | 2.97 | 3.15 | | |
| t-critical | 1.94 | 1.94 | 1.81 | | |
| Result | Same population | Different population | Different population | | |

Acceptance Criteria

Shot weight results for the automated actuations ranged from 75%-100% of the average for manual actuations, meeting the acceptance criteria of 75%-125% of the average shot weight for the manual actuations. The average Dv10 for automated actuations was 81% of the average Dv10 for manual actuations. The average Dv50 for automated actuations was 83% of the average Dv50 for manual actuations. The average Dv90 for automated actuations was 81% of the average Dv90 for manual actuations. Each of these parameters met acceptance criteria of 75%-125% of the average for manual actuations. Students' t-tests, while not necessarily appropriate for the small data sets, indicated that the data sets for manual actuations and automated actuations were equivalent for Dv10, but not for Dv50 or Dv90. It was not possible to accurately replicate the droplet size distribution from manual actuations with the MightyRunt. The force required to reliably break the tabs and actuate the devices produced a distribution with smaller droplets than that of the manual actuations. Less aggressive actuation parameters, which should produce larger droplet sizes, were not sufficient for consistent actuation of the devices. Spraytec method development proceeded with these parameters despite not meeting the acceptance criteria specified in the protocol.

Method Development

Method development involved a vignetting study, device placement study and exhaust placement study utilizing the Spraytec. Actuations were performed using the MightyRunt and the previously qualified parameters. For all tests, the device was placed in front of the laser beam path, the plume traveled through the laser path, and the plume was collected in an exhaust manifold placed behind the laser beam.

The vignetting experiments were performed with the device aligned with the front of the instrument (approximately 10 cm from the beam) and varying distances for the device-to-range lens placement. The results are summarized in Table 42.

TABLE 42

| Distance to Range Lens (cm) | Dv10 (μm) | Dv50 (μm) | Dv90 (μm) |
|---|---|---|---|
| 6 | 17.2 | 38.6 | 65.9 |
| | 16.1 | 36.5 | 63.0 |
| 8 | 18.6 | 41.3 | 71.6 |
| | 21.9 | 44.2 | 84.6 |
| 10 | 16.7 | 38.7 | 80.4 |
| | 16.9 | 39.8 | 68.0 |
| 12 | 22.1 | 46.1 | 89.8 |
| | 17.1 | 37.1 | 65.5 |
| | 15.6 | 35.7 | 62.7 |
| 14 | 17.4 | 42.3 | 72.5 |
| | 16.6 | 36.5 | 64.2 |

A plot of the Dv10, Dv50, Dv90, and plume records values versus placement is set forth in FIG. 11. The data showed no significant trend over the entire range of placements. To minimize the possibility of deposition of droplets on the range lens during testing, the placement of 14 cm (approximately centered between the laser and range lens supports) was chosen and used for all further testing.

To evaluate exhaust placement on the plume during testing, PSD (particle size diameter) data was collected and evaluated at four distances for exhaust-to-laser beam. The data are summarized in Table 43 below.

TABLE 43

| Exhaust Height (cm) | Dv10 (μm) | Dv50 (μm) | Dv90 (μm) |
|---|---|---|---|
| 7 cm Device-to-Laser Beam Placement | | | |
| No exhaust | 14.4 | 28.1 | 51.7 |
| | 13.3 | 28.6 | 54.0 |
| 3 | 19.8 | 37.1 | 60.9 |
| | 18.1 | 36.3 | 61.0 |
| 4 cm Device-to-Laser Beam Placement | | | |
| No exhaust | 17.8 | 35.0 | 57.9 |
| | 18.7 | 36.3 | 60.5 |
| 1 | 14.6 | 29.4 | 51.0 |
| | 12.6 | 28.0 | 56.6 |
| 3 | 15.1 | 30.0 | 52.0 |
| | 13.6 | 27.6 | 49.0 |
| 5 | 14.3 | 32.8 | 79.8 |
| | 13.4 | 28.7 | 51.7 |
| 7 | 11.2 | 25.5 | 55.7 |
| | 15.9 | 30.0 | 50.8 |

A graphical summary of Dv10, Dv50, and Dv90 values versus placement is included in FIG. 12. There were no significant changes in the Dv10, Dv50, Dv90 or plume duration values for plumes collected without exhaust, or with exhaust 1, 3, 5, or 7 cm behind the beam. The exhaust-behind-laser beam placement was chosen to be 3 cm to reduce the chance of deposition outside the fan housing of sprays performed at a device-to-beam distance of 7 cm.

The method was to include two distances for analysis from the tip of the device to the path of the laser for a more complete characterization of the droplet size distribution. Four distances were evaluated, and results are included in Table 44 below.

TABLE 44

| Distance (cm) | Dv10 (μm) | Dv50 (μm) | Dv90 (μm) |
|---|---|---|---|
| 7 | 16.7 | 34.5 | 67.8 |
|   | 15.8 | 33.4 | 60.0 |
| 6 | 17.8 | 35.0 | 57.9 |
|   | 18.7 | 36.3 | 60.5 |
| 5 | 19.1 | 35.5 | 58.5 |
|   | 16.9 | 32.4 | 55.1 |
| 4 | 11.8 | 27.8 | 57.5 |
|   | 13.0 | 28.1 | 50.3 |
| 3 | 14.4 | 28.1 | 51.7 |
|   | 13.3 | 28.6 | 54.0 |

A graphical summary of Dv10, Dv50, and Dv90 values versus placement are included in FIG. 3. There was no observable trend in the data from various heights. While there is no guidance document for sublingual sprays, the FDA Guidance Document "Bioequivalence and Bioavailability Studies for Nasal Aerosols and Nasal Sprays for Local Action", specifies two distances from 3-7 cm. The larger pair of distances (4 cm and 7 cm) from the beam was chosen in order to characterize a more fully developed plume.

Method Validation

An analyst tested six devices at both the 4 cm and 7 cm distances. A second analyst repeated the analyses at both distances with the next actuations after priming from each device on a second day. Validation results are summarized in Tables 45 and 46 below where the Dv10, Dv50, and Dv90 results were compared.

TABLE 45

Validation PSD Results at 4 cm Device-to-Laser Beam Placement

| Device | Dv10 (μm) | Dv50 (μm) | Dv90 (μm) | Shot Weight (mg) | % Average |
|---|---|---|---|---|---|
| Analyst 1 | | | | | |
| 1 | 18.9 | 31.2 | 52.3 | 60.4 | 76 |
| 2 | 16.4 | 30.8 | 52.6 | 78.8 | 100 |
| 3 | 17.2 | 29.8 | 51.3 | 65.0 | 82 |
| 4 | 18.3 | 31.6 | 54.2 | 80.1 | 101 |
| 5 | 13.5 | 28.5 | 51.7 | 81.6 | 103 |
| 6 | 15.0 | 30.1 | 52.3 | 77.2 | 98 |
| Average | 16.5 | 30.3 | 52.4 | 73.9 | |
| % RSD | 12.3 | 3.7 | 1.9 | 12.0 | |
| Analyst 2 | | | | | |
| 1 | 14.2 | 28.8 | 57.5 | 76.8 | |
| 2 | 11.3 | 26.8 | 54.9 | 76.9 | |
| 3 | 11.8 | 27.2 | 52.2 | 79.9 | |
| 4 | 15.4 | 29.2 | 52.6 | 80.0 | |
| 5 | 12.3 | 27.8 | 60.2 | 76.9 | |
| 6 | 11.8 | 26.8 | 52.2 | 84.5 | |
| Average | 12.8 | 27.8 | 54.9 | 79.2 | |
| % RSD | 12.8 | 3.7 | 6.0 | 3.8 | |
| Overall Average | 14.7 | 29.0 | 53.7 | 76.5 | |
| Overall % RSD | 17.9 | 5.8 | 5.0 | 9.0 | |
| Analyst 1 Average as % of Analyst 2 | 129 | 109 | 95 | | |
| t-stat | 3.50 | 4.20 | −1.80 | | |
| t-critical | 1.81 | 1.81 | 1.81 | | |
| Result | Different Population | Different Population | Same Population | | |

TABLE 46

Validation PSD Results at 7 cm Device-to-Laser Beam Placement

| File | Dv10 (μm) | Dv50 (μm) | Dv90 (μm) | Shot Weight (mg) | % Average |
|---|---|---|---|---|---|
| Analyst 1-7 cm | | | | | |
| a009 | 23.3 | 37.0 | 58.8 | 80.1 | 104 |
| a010 | 16.1 | 34.0 | 57.3 | 76.9 | 99 |
| a011 | 16.0 | 34.9 | 59.7 | 79.0 | 102 |
| a012 | 17.6 | 34.0 | 57.1 | 80.7 | 104 |
| a013 | 20.0 | 35.5 | 58.0 | 82.3 | 106 |
| a014 | 19.6 | 36.1 | 57.2 | 80.6 | 104 |
| Average | 18.8 | 35.3 | 58.0 | 79.9 | |
| % RSD | 14.8 | 3.4 | 1.8 | 2.3 | |
| Analyst 2-7 cm | | | | | |
| b009 | 11.8 | 28.7 | 55.0 | 72.6 | |
| b010 | 17.0 | 33.9 | 61.7 | 79.8 | |
| b011 | 15.3 | 31.8 | 55.8 | 74.8 | |
| b012 | 13.8 | 31.1 | 54.6 | 79.7 | |
| b013 | 13.3 | 30.7 | 55.1 | 80.8 | |
| b015 | 16.6 | 32.8 | 56.7 | 76.3 | |
| Average | 14.6 | 31.5 | 56.5 | 77.3 | |
| % RSD | 13.8 | 5.8 | 4.7 | 4.2 | |
| Overall Average | 16.7 | 33.4 | 57.2 | 78.6 | |
| Overall % RSD | 18.9 | 7.3 | 3.6 | 3.6 | |
| Analyst 1 Average as % of Analyst 2 Average | 128 | 112 | 103 | | |
| t-stat | 2.93 | 4.25 | 1.32 | | |
| t-critical | 1.81 | 1.83 | 1.81 | | |
| Result | Different Population | Different Population | Same Population | | |

Acceptance Criteria

Analyst 1 shot weight results ranged from 76%-103% of analyst 2 average for the 4 cm distance, and 99%-106% for the 7 cm distance, meeting the acceptance criteria of 75%-125%. The average Dv10 for Analyst 1 was 129% of Analyst 2 for the 4 cm distance and 128% for the 7 cm distance. The average Dv50 for Analyst 1 was 109% of Analyst 2 for the 4 cm distance and 112% for the 7 cm distance. The average Dv90 Analyst 1 was 95% of Analyst 2 for the 4 cm distance and 103% for the 7 cm distance. While Dv10 did not meet acceptance criteria of 75%-125%, this is a measurement of the smallest droplets in the plume and a higher variability is not unexpected. Results for Dv50 and Dv90 met acceptance criteria of 75-125%. Students' t-tests, while not necessarily appropriate for the small data sets, indicated that the data sets for Analyst 1 and Analyst 2 were equivalent for Dv90 at both distances, but not for Dv10 or Dv50 at either distance.

Conclusion

A method for the droplet size distribution analysis by laser diffraction for use with fentanyl sublingual spray was developed and subsequently qualified. Acceptance criteria based on statistical analysis with students' t-test were deemed inappropriate for the small data sets. Method validation acceptance criteria for agreement of Analysts 1 and 2 were determined to be too narrow for the high variability associated with measurement of the smallest droplets in the plume (Dv10). While these criteria were not met, the method was deemed acceptable for use. The method is suitable for use within the operating parameters specified herein.

Example 17

In Example 17, a study was performed to determine the respirable dose less than 9 μm for fentanyl in 1, 2, 4, 6, and 8 mg/mL fentanyl sublingual spray samples with a working concentration of between 0.1 μg/mL and 5 μg/mL fentanyl in solution. The method used was qualified in compliance with GMP requirements. The sample solutions were determined to be stable over a seven-day period in volumetric glassware and amber HPLC vials at refrigerated and ambient conditions.

The HPLC process was consistent with the process described in Example 15 above. The materials and supplies utilized in the study included acetonitrile (HPLC Grade), potassium phosphate monobasic (ACS Grade), phosphoric acid (ACS Grade), deionized water, alcohol (ethanol, absolute), Short Stack Andersen Cascade Impactor set-up consisting of a 5-liter expansion chamber, induction port, stages 0, 1, 2, and after filter, a vacuum source, in-line flow meter (Sierra Top-Track or equivalent), VWR® (VWR is a registered trademark of VWR International, Inc.) Sterile sampling bags, glass fiber filter, 8.1 cm, external calibrated flow meter (Dry-Cal Flow Meter or equivalent), and a pneumatic actuator (Innova Systems Mighty Runt or equivalent).

Solution Preparation

Solution preparations were prepared according to the methods described in Example 15 above and may be scaled as required.

The extraction solution was 50:50 (95/5, Ethanol/Acetonitrile:Water). For every liter of prepared solution, 475 mL ethanol, 25 mL acetonitrile and 500 mL of water was combined in a suitable container and mixed well. This solution expires after one month.

The phosphate buffer solution was prepared in a concentration of 50 mM $KH_2PO_4$ with a pH 2.8. For every liter of prepared solution, 6.8 g potassium phosphate mono basic and 1 liter of water is combined in a suitable vessel and mixed well. The pH of the solution was adjusted to pH 2.8 with the drop-wise addition of phosphoric acid. The solution was filtered through 0.45 μm nylon. This solution expires after one month.

The impactor set-up will consist of a 5-liter expansion chamber, induction port, stages 0, 1, 2, and filter prepared according to the following procedure.

The filter stage was placed onto the impactor base.

An 8.1 cm glass fiber filter was placed into the after filter stage and secured with a clean rubber o-ring.

A solid plate was placed on top of the filter stage and then stage 2 was placed in position.

A plate with center hole cutout was placed on top of stage 2 and then stage 1 was placed in position.

A plate with center hole cutout was placed on top of stage 1 and then stage 0 was in position.

The cone was placed in position and the impactor was secured with the hold down clamps.

The induction port was affixed to the cone and the 5 L expansion chamber was placed on top of the induction port.

Testing Set-Up

The testing instrumentation was set up by placing an in-line flow meter between the vacuum source and cascade impactor with appropriate tubing. A leak test was performed on the impactor. A flow through the impactor was started by opening the vacuum source and the flow was adjusted to approximately 28.3 L/min. A hand was placed over the spray actuation port on the expansion chamber. The flow rate as indicated on the in-line meter was expected to fall to zero. If a flow was still registered, the condition of the impactor a-rings was checked, and the test repeated. To set the flow rate, the expansion chamber was removed from the induction port and an external calibrated flow meter was attached to the induction port and the flow was started. The flow was adjusted to 28.3±1 L/min with the external calibrated meter and the measurement displayed on the in-line flow meter was recorded for using during the testing procedure.

Testing Procedure

Two devices were actuated for the 1 mg/mL product strength for each assay result. One device was actuated for the 2, 4, 6, and 8 mg/mL product strength. With the expansion chamber in place, the vacuum was started and the flow adjusted to the measurement obtained in during the testing set-up.

The pre-actuated weight of the device in grams to a minimum of 4 decimal places was recorded. The device was positioned so that the spray would travel directly toward the wall opposite the actuation port. The sublingual spray device was actuated into the expansion chamber with the automated pneumatic actuator method parameters listed in Table 47.

TABLE 47

| Parameter | Setting |
| --- | --- |
| Actuation Force (kg) | 5.0 |
| Force Rise Time (s) | 0.1 |
| Hold Time (s) | 1.0 |
| Force Fall Time (s) | 1.0 |
| Spray Delays (s) | 1 |
| Minimum Travel Distance (mm) | 10.0 |
| Maximum Travel Time (s) | 4.0 |
| Trigger Signal Delay (s) | 0.0 |
| Stage | Yes |

The post actuated weight of the device in grams is recorded to a minimum of 4 decimal places.

Extraction Procedure

Extraction was accomplished by breaking down the impactor set-up and extracting each component by the following procedures:

The plates and the filter were each extracted separately in bags with 10.0 mL of extraction solution. The sample was extracted by hand shaking and kneading for at least one minute. 6.0 mL of the extracted sample was transferred to a 10 mL volumetric flask and diluted to volume with phosphate buffer solution and mixed well. This is the sample solution. This solution expires after seven days.

The expansion chamber is inverted and place in a holder. The induction port and cone is inserted into the expansion chamber ground glass joint. Approximately 40 mL of extraction solution is rinsed through the cone and induction port into the expansion chamber. The solution is swirled in the expansion chamber in an effort to extract the entire interior surface. The solution is decanted into a 200 mL volumetric flask. The rinse is repeated two additional times for a total rinse volume of approximately 120 mL. The flask is brought to volume with phosphate buffer solution and mixed well. This is the sample solution. This solution expires after seven days.

Assay

The sample solutions are assayed as per the procedure set forth in Example 15 above. Calculations are performed as follows.

$$\text{Response Factor } (Rf) = \frac{\text{Fentanyl Peak Area}}{\text{Fentanyl Concentration}(\mu g/mL)}$$

The fentanyl in the plate and filter samples were determined according to the following calculation:

$$\text{The amount of fentanyl in } \mu g = \frac{A_{samp} * D_f}{WSI\ R_f OTR}$$

$A_{samp}$=Area of fentanyl in sample preparation
$D_f$=Dilution factor of fentanyl sample solution preparation (10.0 mL×10.0 ml/6.0 mL)
WSI $R_f$OTR=Working standard I response factor over the run The fentanyl in the cone, induction port and expansion chamber is determined according to the following calculation:

$$\text{Amount of fentanyl in } \mu g = \frac{A_{samp} * V_{samp}}{WSI\ R_f OTR}$$

$A_{samp}$=Area of fentanyl in sample preparation
$V_{samp}$=Volume of fentanyl in sample solution preparation (200 mL)
WSI $R_f$OTR=Working standard I response factor over the run The respirable dose for 2, 4, 6, and 8 mg/mL is calculated as follows:
Respirable dose in μg=
Sum of the Drug Mass in Particle Size Fraction Less Than 9 μm (μg)
The respirable dose for 1 mg/mL is calculated as follows:

$$\text{Respirable dose } (\mu g) = \frac{\text{Sum of the drug mass in particle size fraction less than 9 } \mu g\ (\mu g)}{2(\text{number of actuations})}$$

The respirable fraction is calculated as follows:

$$\text{Percent (\%) Respirable fraction} = \frac{\text{Drug mass in particle size fraction less than 9 } \mu m\ (\mu g)(\text{respirable dose})}{\text{Total Drug Mass } (\mu g)} \times 100$$

The particle size cutoff diameters for reporting is set forth in Table 48 below.

TABLE 48

| Impactor Component | Particle Size Grouping |
|---|---|
| Expansion Chamber, Induction Port, and Cone | ≥9 μm |
| Plate 0 | |
| Plate 1 | 9 μm > X ≥ 5.8 μm |
| Plate 2 | <5.8 μm |
| F | |

The results for the fentanyl sample assay results in pg, the respirable dose in the particle size fraction less than 9 μm (as per Table 48) in μg, and the percent respirable dose less than 9 μm in percent to one decimal place were reported.

The Certificate of Analysis for the determination of the respirable 1 mg/mL dose set forth in Table 49 below.

TABLE 49

Determination of Respirable Dose, 1 mg/mL Fentanyl

| Test | Method | Specification |
|---|---|---|
| Assay of Fentanyl in sublingual spray samples | Described in Example 17 | Report Results |
| Determination of respirable dose in fentanyl sublingual spray by cascade impaction | | Report Results |

| CI Run | Sample | Fentanyl (μg/ dose) | Particle Size groupings | Groupings percent | Average Shot weight (mg) | Total Mass <9 μm (μg) | Respirable dose <9 μm (μg) |
|---|---|---|---|---|---|---|---|
| 1 | Globe | 76.5694 | ≥9 μm | 96.4 | 85.4 | 2.9 | 3.6 |
| | Plate 0 | 0.5479 | | | | | |
| | Plate 1 | 0.6228 | 9 μm > X ≥ 5.8 μm | 0.8 | | | |
| | Plate 2 | 0.4746 | <5.8 μm | 2.9 | | | |
| | Filter | 1.8149 | | | | | |
| 2 | Globe | 78.6941 | ≥9 μm | 96.6 | 84.0 | 2.8 | 3.4 |
| | Plate 0 | 0.6746 | | | | | |
| | Plate 1 | 0.6217 | 9 μm > X ≥ 5.8 μm | 0.8 | | | |
| | Plate 2 | 0.5000 | <5.8 μm | 2.6 | | | |
| | Filter | 1.6740 | | | | | |
| 3 | Globe | 78.0529 | ≥9 μm | 97.1 | 85.3 | 2.3 | 2.9 |
| | Plate 0 | 0.5082 | | | | | |

TABLE 49-continued

| Determination of Respirable Dose, 1 mg/mL Fentanyl | | | |
|---|---|---|---|
| Plate 1 | 0.5429 | 9 μm > X ≥ 5.8 μm | 0.7 |
| Plate 2 | 0.4185 | <5.8 μm | 2.2 |
| Filter | 1.3596 | | |
| | | Average percent respirable dose | 3.3 |

Example 18

Fentanyl SL Spray Formulations

In Example 18, formulations 18A-18E were prepared in accordance with the procedures set forth in the above examples. The formulations are set forth in Table 50 below.

TABLE 50

| | Quantity % w/w | | | | |
|---|---|---|---|---|---|
| Component | Formulation 18A | Formulation 18B | Formulation 18C | Formulation 18D | Formulation 18E |
| Fentanyl base | 0.111 (1 mg/mL) | 0.222 (2 mg/mL) | 0.4444 (4 mg/mL) | 0.6667 (6 mg/mL) | 0.8889 (8 mg/mL) |
| Dehydrated alcohol | 55.00 | 55.00 | 55.00 | 55.00 | 55.00 |
| Propylene glycol | 5.00 | 5.00 | 5.00 | 5.00 | 5.00 |
| L-Menthol | 0.05 | 0.05 | 0.05 | 0.05 | 0.05 |
| Xylitol | 3.00 | 3.00 | 3.00 | 3.00 | 3.00 |
| Purified water | 36.839 | 36.728 | 36.5006 | 36.2833 | 36.0611 |
| TOTAL | 100 | 100 | 100 | 100 | 100 |

Example 19

Clinical Study

A Phase I, single-dose, open-label, randomized, three-period, three-treatment crossover study was conducted to compare the rate of absorption and bioavailability of Fentanyl Sublingual Spray 400 mcg to Actiq® 400 mcg and to Fentanyl Citrate Injection (IV) 100 mcg.

Subjects received each of the treatments below in randomized fashion during the three treatment periods, separated by a washout period of at least 7 days:
    Treatment A: Fentanyl Sublingual Spray (Formulation 18C of Example 18)
        Dose=1×400 mcg sublingual spray
        Insys Therapeutics, Inc.
    Treatment B: Actiq®
        Dose=1×400 mcg oral transmucosal unit
        Cephalon
    Treatment C: Fentanyl Citrate Injection
        Dose=1×100 mcg IV
        Hospira, Inc Blood samples (1×6 mL) were collected in vacutainer tubes containing EDTA as a preservative from the subjects at 0 (pre-dose) and at 5, 10, 20, 30, and 40 minutes after dosing and at 1.0, 1.25, 1.5, 2.0, 4.0, 6.0, 8.0, 10.0, 12.0, 16.0, 24.0, and 36.0 hours after dosing. The plasma samples were then analyzed for fentanyl using a validated liquid chromatography tandem mass spectrometry (LC-MS-MS) procedure. The method was validated for a range of 0.0250 to 5.00 ng/mL for fentanyl, based on the analysis of 0.500 mL of EDTA human plasma.

Data from 21 subjects who completed the study was subjected to pharmacokinetic and statistical analyses. Concentration-time data was transferred from Watson LIMS directly to WinNonlin Enterprise Edition (Version 4.0, Pharsight® Corporation; Pharsight is a registered trademark of Tripos L.P.) using the Custom Query Builder option for analysis. Data was analyzed by noncompartmental methods in Win-Nonlin. Concentration-time data that were below the limit of quantification (BLQ) were treated as zero (0.00 ng/mL) in the data summarization and descriptive statistics.

In the pharmacokinetic analysis, BLQ concentrations were treated as zero from time-zero up to the time at which the first quantifiable concentration was observed; embedded and/or terminal BLQ concentrations were treated as "missing".

Pharmacokinetic parameters were then calculated for each formulation using non-compartmental methods. Specifically, the following pharmacokinetic parameters were calculated: peak concentration in plasma ($C_{max}$), time to peak concentration ($T_{max}$), elimination rate constant ($\lambda_z$), terminal half-life ($T_{1/2}$), area under the concentration-time curve from time-zero to the time of the last quantifiable concentration ($AUC_{last}$), and area under the plasma concentration time curve from time-zero extrapolated to infinity ($AUC_{inf}$).

The bioavailability (F) after oral/sublingual administration was also calculated. The bioavailability was calculated by using the following equation:

$$F = \frac{Dose_{IV} * AUC_{extravascular}}{Dose_{extravascular} * AUC_{IV}},$$

where $Dose_{IV}$ and $Dose_{extravascular}$ are the IV and extravascular (sublingual spray and Actiq®) doses, respectively, and $AUC_{IV}$ and $AUC_{extravascular}$ are the areas under the plasma concentration-time profiles after IV and extravascular administration, respectively. Individual $AUC_{last}$ and $AUC_{inf}$ values after each treatment were used for the calculations.

To compare the fentanyl sublingual spray to Actiq®, analysis of variance (ANOVA) and the Schuirmann's two one-sided t-test procedures at the 5% significance level were applied to the log-transformed pharmacokinetic exposure parameters, $C_{max}$, $AUC_{last}$, and $AUC_{inf}$. The 90% confidence intervals for the ratio of the geometric means (Test/Reference) were calculated.

Figure 15:
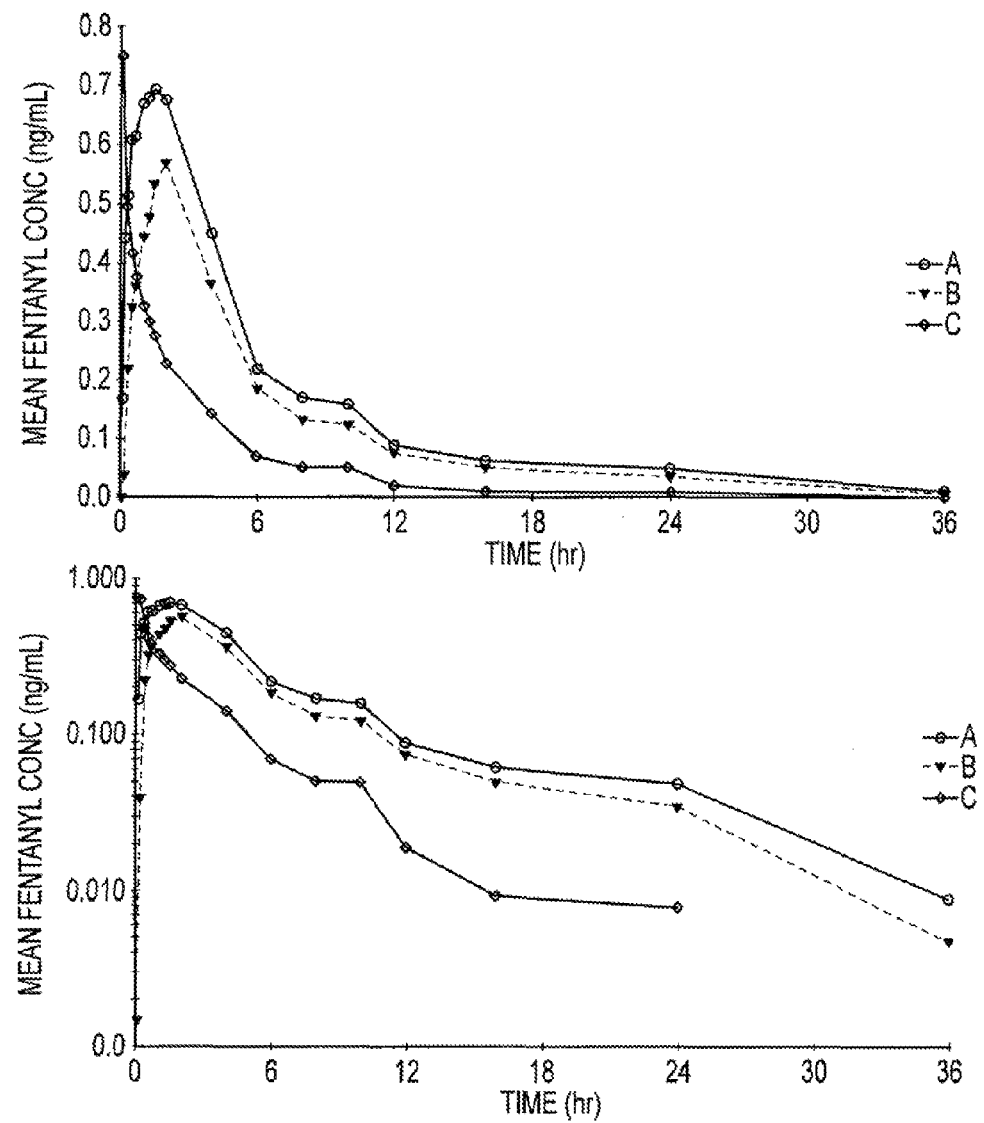
FIG. 15 depicts the mean fentanyl concentration-time profiles after administration of Fentanyl Sublingual Spray 400 mcg (Treatment A), Actiq® 400 mcg (Treatment B) and Fentanyl Citrate Injection 100 mcg (Treatment C) in the clinical study of Example 19.

The mean concentration-time data are shown in Table 51 and FIG. 15 below. Results of the pharmacokinetic and statistical analyses are shown in Table 52 and Table 53 below. The bioavailability estimates are summarized in Table 54 below.

TABLE 51

Fentanyl Concentration-Time Data after Administration of Fentanyl Sublinqual Spray 400 mcg (Treatment A), Actiq ® 400 mcg (Treatment B) and Fentanyl Citrate Injection 100 mcg (Treatment C)

| Time (hr) | n | Treatment A: Fentanyl Sublinqual Spray 400 mcg | | | n | Treatment B: Actiq ® 400 mcg | | | n | Treatment C: Fentanyl Citrate Injection 100 mcg | | |
|---|---|---|---|---|---|---|---|---|---|---|---|---|
| | | Mean (ng/mL) | SD (ng/mL) | CV (%) | | Mean (ng/mL) | SD (ng/mL) | CV (%) | | Mean (ng/mL) | SD (ng/mL) | CV (%) |
| 0.00 | 21 | 0.00 | 0.00 | NC | 21 | 0.00 | 0.00 | NC | 21 | 0.00 | 0.00 | NC |
| 0.08 | 21 | 0.168 | 0.189 | 112.68 | 21 | 0.00146 | 0.00669 | 458.26 | 21 | 0.749 | 0.607 | 81.08 |
| 0.17 | 21 | 0.440 | 0.300 | 68.30 | 21 | 0.0396 | 0.0511 | 129.24 | 21 | 0.730 | 0.240 | 32.84 |
| 0.33 | 21 | 0.513 | 0.242 | 47.24 | 21 | 0.220 | 0.150 | 68.04 | 21 | 0.494 | 0.185 | 37.44 |
| 0.50 | 21 | 0.606 | 0.288 | 47.45 | 21 | 0.324 | 0.112 | 34.56 | 21 | 0.416 | 0.137 | 33.01 |
| 0.67 | 21 | 0.613 | 0.238 | 38.81 | 21 | 0.360 | 0.127 | 35.10 | 21 | 0.376 | 0.108 | 28.64 |
| 1.00 | 21 | 0.670 | 0.264 | 39.32 | 21 | 0.444 | 0.170 | 38.26 | 21 | 0.327 | 0.0773 | 23.61 |
| 1.25 | 21 | 0.679 | 0.204 | 30.11 | 21 | 0.478 | 0.163 | 34.07 | 21 | 0.299 | 0.0689 | 23.04 |
| 1.50 | 21 | 0.694 | 0.203 | 29.19 | 21 | 0.533 | 0.198 | 37.23 | 21 | 0.275 | 0.0607 | 22.05 |
| 2.00 | 21 | 0.674 | 0.182 | 26.98 | 21 | 0.570 | 0.173 | 30.40 | 21 | 0.229 | 0.0475 | 20.74 |
| 4.00 | 21 | 0.449 | 0.126 | 28.05 | 21 | 0.363 | 0.146 | 40.04 | 21 | 0.141 | 0.0339 | 24.00 |
| 6.00 | 21 | 0.218 | 0.0793 | 36.31 | 21 | 0.185 | 0.0713 | 38.57 | 21 | 0.0693 | 0.0167 | 24.16 |
| 8.00 | 21 | 0.170 | 0.0673 | 39.72 | 21 | 0.132 | 0.0519 | 39.43 | 21 | 0.0502 | 0.0157 | 31.19 |
| 10.00 | 21 | 0.159 | 0.0720 | 45.44 | 21 | 0.123 | 0.0609 | 49.39 | 21 | 0.0489 | 0.0209 | 42.68 |
| 12.00 | 21 | 0.0886 | 0.0396 | 44.65 | 21 | 0.0710 | 0.0399 | 56.20 | 21 | 0.0188 | 0.0193 | 102.75 |
| 16.00 | 21 | 0.0614 | 0.0322 | 52.50 | 21 | 0.0497 | 0.0299 | 60.15 | 21 | 0.00877 | 0.0145 | 165.79 |
| 24.00 | 21 | 0.0484 | 0.0357 | 73.79 | 21 | 0.0345 | 0.0319 | 92.44 | 21 | 0.00777 | 0.0171 | 220.03 |
| 36.00 | 21 | 0.00876 | 0.0164 | 187.39 | 21 | 0.00465 | 0.0123 | 263.87 | 21 | 0.00 | 0.00 | NC |

Note:
Plasma samples analyzed using a bioanalytical method with a validated range 0.0250 to 5.00 ng/mL; concentrations below limit of quantification set to zero (0.00 ng/mL) in the data summarization
NC = Not calculated

TABLE 52

Pharmacokinetic Parameters of Fentanyl

| Parameter | n | Treatment A: Fentanyl Sublinqual Spray 400 mcg | | | n | Treatment B: Actiq ® 400 mcg | | | n | Treatment C: Fentanyl Citrate Injection 100 mcg | | |
|---|---|---|---|---|---|---|---|---|---|---|---|---|
| | | Mean | SD | CV % | | Mean | SD | CV % | | Mean | SD | CV % |
| $T_{max}$ (hr) | 21 | 1.28 | 0.60 | 47.18 | 21 | 1.70 | 0.42 | 25.04 | 21 | 0.16 | 0.08 | 50.52 |
| $C_{max}$ (ng/mL) | 21 | 0.813 | 0.252 | 31.01 | 21 | 0.607 | 0.185 | 30.55 | 21 | 0.929 | 0.515 | 55.48 |
| $AUC_{last}$ (hr * ng/mL) | 21 | 4.863 | 1.708 | 35.12 | 21 | 3.677 | 1.440 | 39.17 | 21 | 1.688 | 0.4114 | 24.38 |
| $AUC_{inf}$ (hr * ng/mL) | 16 | 5.761 | 1.916 | 33.26 | 18 | 4.182 | 1.670 | 39.93 | 16 | 1.758 | 0.3822 | 21.74 |
| $AUC_{Extrap}$ (%) | 16 | 10.26 | 5.66 | 55.19 | 18 | 10.64 | 5.68 | 53.38 | 16 | 11.14 | 3.44 | 30.92 |
| $\lambda_2$ (hr$^{-1}$) | 16 | 0.0904 | 0.0571 | 63.16 | 18 | 0.1097 | 0.0532 | 48.51 | 16 | 0.1775 | 0.0662 | 37.30 |
| $T_{1/2}$ (hr) | 16 | 9.98 | 4.41 | 44.14 | 18 | 7.89 | 3.72 | 47.15 | 16 | 4.50 | 1.94 | 43.02 |
| $T_{last}$ (hr) | 21 | 25.15 | 7.17 | 28.50 | 21 | 22.86 | 6.83 | 29.87 | 21 | 13.81 | 5.51 | 39.90 |
| $C_{last}$ (ng/mL) | 21 | 0.0408 | 0.0117 | 28.74 | 21 | 0.0363 | 0.00953 | 26.23 | 21 | 0.0352 | 0.0117 | 33.08 |

TABLE 53

Statistical Analysis of the Log-Transformed Systemic Exposure Parameters of Fentanyl Comparing Fentanyl Sublingual Spray 400 mcg (Treatment A) to Actiq ® 400 mcg (Treatment B)

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 0.7865 | 0.5884 | 133.67 | 119.67 | 149.31 | 0.9527 | 20.85 |
| $\ln(AUC_{last})$ | 4.6392 | 3.4767 | 133.44 | 121.47 | 146.58 | 0.9859 | 17.65 |
| $\ln(AUC_{inf})$ | 5.5080 | 4.0420 | 136.27 | 121.21 | 153.20 | 0.9341 | 17.06 |

[a]Geometric Mean for Treatment A (Test) and Treatment B (Ref) based on Least Squares Mean of log-transformed parameter values
[b]Ratio(%) = Geometric Mean (Test)/Geometric Mean (Ref)
[c]90% Confidence Interval

TABLE 54

Bioavailability of Fentanyl after Administration of Fentanyl Sublingual Spray (Treatment A) and Actiq ® (Treatment B)

| Treatment | n | F(AUC$_{last}$) | | | n | F(AUC$_{inf}$) | | |
|---|---|---|---|---|---|---|---|---|
| | | Mean | SD | CV (%) | | Mean | SD | CV (%) |
| A | 21 | 0.721 | 0.199 | 27.59 | 11 | 0.756 | 0.212 | 28.02 |
| B | 21 | 0.540 | 0.135 | 25.08 | 13 | 0.511 | 0.0973 | 19.05 |

It was concluded that Fentanyl SL intermediates between Actiq® and Fentanyl IV, as to time to reach threshold concentration, and that Fentanyl SL concentrations are about 40% higher than Actiq® (Bioavailbility is 71±16% vs. 52±13% for Actiq®). Terminal half-life is similar in all three treatments (Fentanyl IV has an artifactually different decline beyond 10 hr because concentrations on many subjects fell below assay sensitivity (Assay sensitivity=0.050 ng/mL (50 pg/mL)).

It was further concluded, based on reports of time to onset for Actiq® (30 min) and Fentora (15 min), that threshold concentration of fentanyl is probably ~0.3-4 ng/mL. Fentanyl SL reaches 0.3-0.4 ng/mL 10 minutes post dose, which is 20 minutes sooner than Actiq®.

Example 20

Dose Escalation Clinical Study

Figure 16:
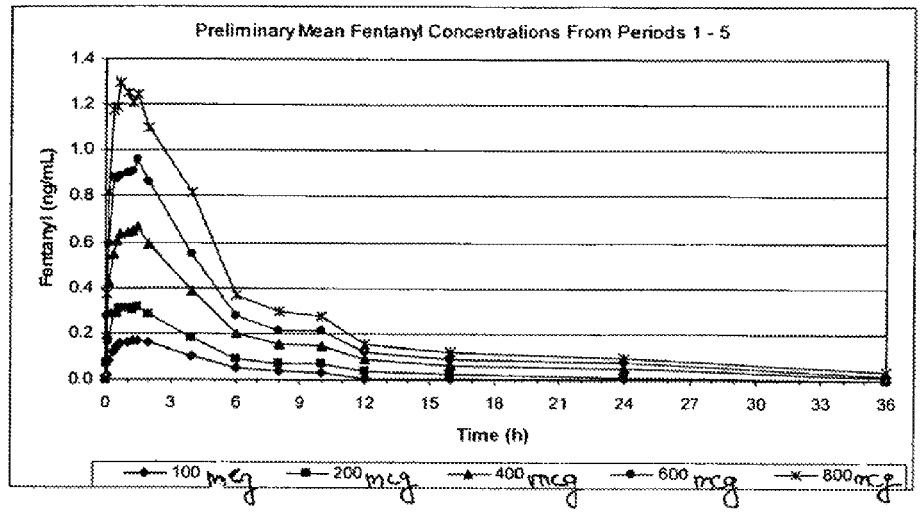
FIG. 16 depicts the preliminary pharmacokinetic data in the dose escalation study of Example 20.
Figure 17:
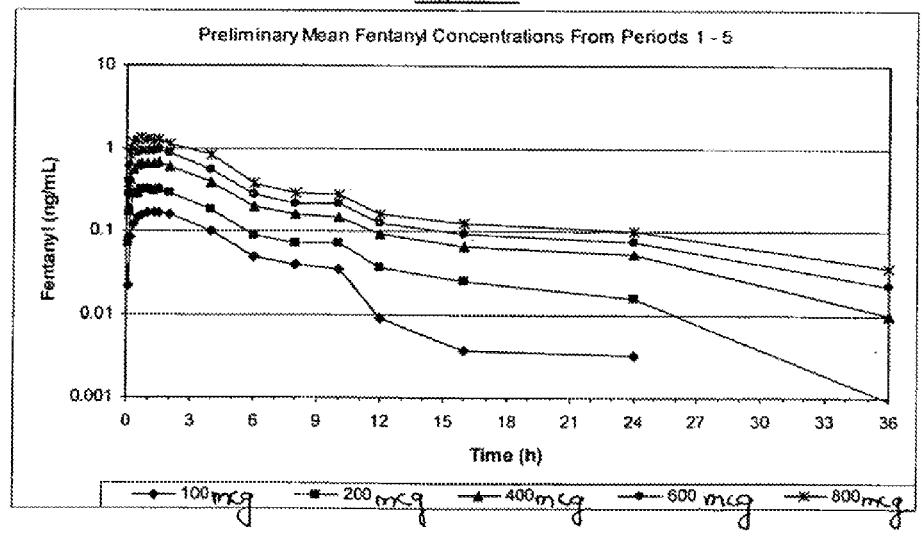
FIG. 17 depicts the preliminary pharmacokinetic data in the dose escalation study of Example 20.
Figure 18:
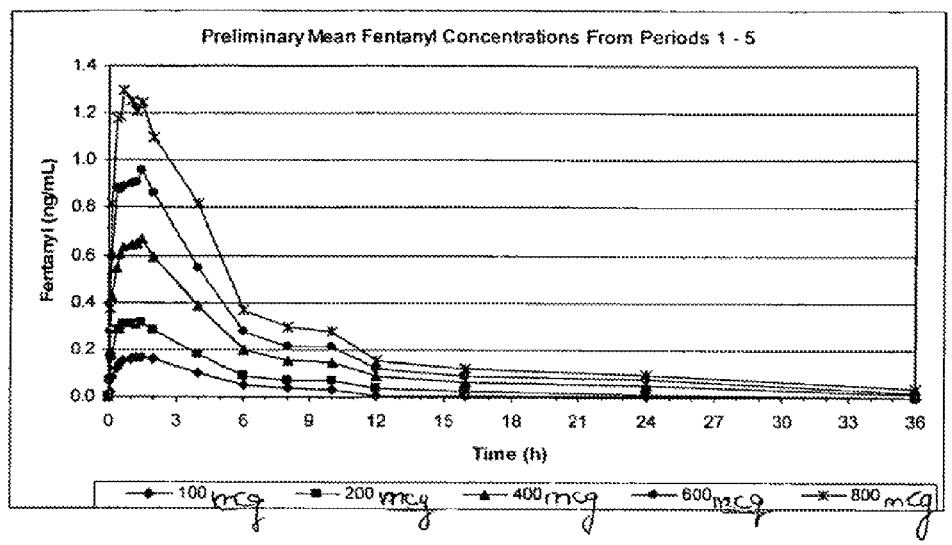
FIG. 18 depicts the preliminary pharmacokinetic data in the dose escalation study of Example 20.

A dose escalation Phase I study on Fentanyl SL has been initiated. Formulation 18A, Formulation 18B, Formulation 18C, Formulation 18D, and Formulation 18E, all of Example 18 were used. Doses of 100 mcg, 200 mcg, 400 mcg, 600 mcg, and 800 mcg were administered to 40, 39, 42, 40, and 42 patients, respectively. The bio-analytical method was performed according to the procedure set forth in Example 19 above. The preliminary pharmacokinetic data is provided in Table 54 below, and is graphically represented in FIG. 16, FIG. 17 and FIG. 18.

TABLE 54

| | N # | Cmax ng/ml | Tmax h | AUC(0-t) ng * h/mL | Dose Adj'ed Cmax (to 100 mg) | Dose Adj'ed AUC (to 100 mg) |
|---|---|---|---|---|---|---|
| 100 mcg | 40 | 0.193 | 1.12 | 0.919 | 0.193 | 0.919 |
| 200 mcg | 39 | 0.379 | 1.04 | 1.94 | 0.189 | 0.971 |
| 400 mcg | 42 | 0.796 | 0.970 | 4.58 | 0.199 | 1.15 |
| 600 mcg | 40 | 1.15 | 0.987 | 6.65 | 0.192 | 1.11 |
| 800 mcg | 42 | 1.56 | 1.06 | 8.93 | 0.195 | 1.12 |

The preliminary data appears to support the conclusion that Fentanyl SL has faster onset (60% $T_{max}$ in 10 minutes) and therefore pain relief than analgesic products currently available commercially (i.e., Actiq®, Fentora®; fentanyl buccal tablet, Fentora is a registered trademark of Fentora Cima Labs Inc., Rapinyl®; fentanyl citrate, Rapinyl is a registered trademark of Endo Pharmaceuticals Inc., BEMA Fentanyl). The preliminary data also indicates that Fentanyl SL stays close to $T_{max}$ for 100 minutes translating to pain relief for a longer time.

Example 21

Pharmacokinetic Profile of Fentanyl Sublingual (SL) Spray

In Example 21, a five-treatment, five-sequence, five-period crossover study of fentanyl SL spray was conducted under fasted conditions in up to 70 healthy subjects. The objectives were to determine the pharmacokinetics of five difference doses (Part A), and to assess the impact of temperature and pH in the oral cavity on the relative bioavailability at a fixed dose (Part B). Healthy subjects had to meet pre-specified eligibility criteria. Plasma samples were obtained at time points of 0, 5, 10, 20, 30, 40 min, 1, 1.25, 1.5, 2, 4, 6, 8, 10, 12, 16, 24 and 36 h post-dose and analyzed for fentanyl using a validated LC-MS-MS procedure.

53 subjects were enrolled in part A. Administration of fentanyl SL spray was dose-proportional over the 100 mcg to 800 mcg dose ranges. Fentanyl concentrations increase rapidly following administration, being above the LLOQ within 5 minutes, reaching 60.6% of the peak plateau by 10 minutes and 86.6% of the peak plateau by 20 minutes post dose. Fentanyl concentrations showed a relatively long plateau about the peak value (>80% of Cmax) that lasted approximately 2 hours.

14 subjects were enrolled in part B. Varying the pH and temp of the oral cavity did not affect the PK profile. No SAEs were noted. AEs were observed in 31 subjects in part A. 46 were probably related to study treatment, and 29 were possibly related. During part B, AEs were observed in 9 subjects. 7 were probably related to study treatment, and 17 were possibly related. AEs were emesis or nausea.

The results of this study support the rationale for assessing efficacy in patients with breakthrough pain. The dose proportionality supports a rationale for predictable dosing favorable for titration.

Example 22

Comparative Bioavailability of Fentanyl Sublingual (SL) Spray, IV Fentanyl Citrate and Actiq In Example 22, a single-dose, open-label, randomized, three-period, three-treatment crossover study with a washout period of at least seven days between study periods was conducted at a phase I contract clinic under good clinical practice guidelines. 40 healthy volunteers were enrolled, having met pre-specified eligibility criteria. Subjects received a single dose of fentanyl SL spray 400 mcg, Actiq 400 mcg lozenge, and fentanyl citrate 100 mcg by IV injection over 5 minutes in 3 separate treatment periods. Plasma samples were obtained at time points of 0, 5, 10, 20, 30, 40 min, 1, 1.25, 1.5, 2, 4, 6, 8, 10, 12, 16, 24 and 36 h post-dose and analyzed for fentanyl using a validated LC-MS-MS procedure.

The results showed that compared to intravenous administration, the median value for absolute bioavailability of fentanyl SL spray was 60.8%; bioavailability of Actiq was 46.6%. The median value for relative bioavailability of Fentanyl SL Spray to that of Actiq was 135%. Systemic absorption of fentanyl SL was more rapid than Actiq. Subjects were monitored for any adverse events. AEs were reported in 15 of the 40 subjects. All of the AEs were mild. Two of the AEs were probably related to the study drug (both were sublingual burning at 400 mcg). Three of the AEs were possibly related to the study treatment (headache, dizziness, and dry throat all reported at 400 mcg).

The results of this study support the rationale for assessing efficacy in patients with breakthrough pain.

Many other variations of the present invention will be apparent to those skilled in the art and are meant to be within the scope of the claims appended hereto, including but not limited to the particular unit dose or bi-dose devices and the particle size range of fentanyl produced, as well as other numerical parameters described in the examples, and any combination thereof.

What is claimed is:

1. A sublingual formulation comprising from about 0.001% to about 15% by weight fentanyl, a free base, or a pharmaceutically acceptable salt thereof, from about 20% to about 60% by weight ethanol, and from about 4% to about 6% by weight propylene glycol, the formulation providing a mean $T_{max}$ of about 1.28+/−0.60 hours when a dose is administered sublingually to humans.

2. A sublingual formulation comprising from about 0.001% to about 15% by weight fentanyl, a free base, or a pharmaceutically acceptable salt thereof, from about 50% to about 60% by weight ethanol, and from about 4% to about 6% by weight propylene glycol, which provides a plasma concentration after administration to humans selected from the group consisting of: about 60% of the mean $C_{max}$ in about 10 minutes, about 86% of the mean $C_{max}$ by about 20 minutes and a combination thereof.

3. The sublingual formulation of claim 1, that when administered to humans provides a plasma concentration that is greater than about 80% of the mean $C_{max}$ for about 2 hours.

4. A sublingual spray formulation comprising 400 mcg dose of fentanyl, a free base, or a pharmaceutically acceptable salt thereof, which provides one or more mean pharmacokinetic values selected from the group consisting of: $AUC_{last}$ 4.863+/−1.70821 hr*ng/mL, $AUC_{inf}$ 5.761+/−1.916 hr*ng/mL, and $AUC_{extrap}$ 10.26+/−5.66%, when administered to humans.

5. A sublingual spray formulation comprising a dose of fentanyl, a free base, or a pharmaceutically acceptable salt thereof, which provides a substantially dose proportional mean $AUC_{last}$ based on a mean $AUC_{last}$ of about 4.863+/−1.70821 hr*ng/mL for a 400 mcg fentanyl dose when administered to humans.

6. A sublingual spray formulation comprising a 400 mcg dose of fentanyl, a free base, or a pharmaceutically acceptable salt thereof, which provides a mean $F(AUC_{last})$ of about 0.721+/−0.199 ng/mL when administered to humans.

* * * * *